United States Patent
Capano et al.

(10) Patent No.: US 12,251,411 B2
(45) Date of Patent: *Mar. 18, 2025

(54) METHODS OF TREATING ENDOMETRIAL CANCER USING HEMP EXTRACT

(71) Applicants: Ecofibre USA Inc., Georgetown, KY (US); The University of Newcastle, Callaghan (AU)

(72) Inventors: Alexandra M. Capano, Philadelphia, PA (US); Pradeep Singh Tanwar, Fletcher (AU); Alex Nance, Georgetown, KY (US)

(73) Assignees: Ecofibre USA Inc., Georgetown, KY (US); The University of Newcastle, Callaghan (AU)

( * ) Notice: Subject to any disclaimer, the term of this patent is extended or adjusted under 35 U.S.C. 154(b) by 0 days.

This patent is subject to a terminal disclaimer.

(21) Appl. No.: 18/467,953

(22) Filed: Sep. 15, 2023

(65) Prior Publication Data

US 2024/0000876 A1 Jan. 4, 2024

Related U.S. Application Data

(63) Continuation of application No. 18/050,021, filed on Oct. 26, 2022, now Pat. No. 11,793,847.

(60) Provisional application No. 63/263,018, filed on Oct. 26, 2021, provisional application No. 63/263,026, filed on Oct. 26, 2021, provisional application No. 63/263,020, filed on Oct. 26, 2021.

(51) Int. Cl.
| | |
|---|---|
| A61K 31/05 | (2006.01) |
| A61K 31/01 | (2006.01) |
| A61K 31/015 | (2006.01) |
| A61K 31/045 | (2006.01) |
| A61K 31/198 | (2006.01) |
| A61K 31/216 | (2006.01) |
| A61K 31/282 | (2006.01) |
| A61K 31/337 | (2006.01) |
| A61K 31/352 | (2006.01) |
| A61K 31/355 | (2006.01) |
| A61K 31/395 | (2006.01) |
| A61K 31/4745 | (2006.01) |
| A61K 31/513 | (2006.01) |
| A61K 31/519 | (2006.01) |
| A61K 31/675 | (2006.01) |
| A61K 31/704 | (2006.01) |
| A61K 31/7048 | (2006.01) |
| A61K 31/7068 | (2006.01) |
| A61K 33/243 | (2019.01) |
| A61K 36/185 | (2006.01) |
| A61K 39/395 | (2006.01) |
| A61P 35/00 | (2006.01) |

(52) U.S. Cl.
CPC ............ *A61K 36/185* (2013.01); *A61K 31/01* (2013.01); *A61K 31/015* (2013.01); *A61K 31/045* (2013.01); *A61K 31/05* (2013.01); *A61K 31/198* (2013.01); *A61K 31/216* (2013.01); *A61K 31/282* (2013.01); *A61K 31/337* (2013.01); *A61K 31/352* (2013.01); *A61K 31/355* (2013.01); *A61K 31/4745* (2013.01); *A61K 31/513* (2013.01); *A61K 31/519* (2013.01); *A61K 31/5545* (2017.08); *A61K 31/675* (2013.01); *A61K 31/704* (2013.01); *A61K 31/7048* (2013.01); *A61K 31/7068* (2013.01); *A61K 33/243* (2019.01); *A61K 39/3955* (2013.01); *A61P 35/00* (2018.01)

(58) Field of Classification Search
CPC .... A61K 36/185; A61K 31/01; A61K 31/015; A61K 31/045; A61K 31/05; A61K 31/198; A61K 31/216; A61K 31/282; A61K 31/337; A61K 31/352; A61K 31/355; A61K 31/4745; A61K 31/513; A61K 31/519; A61K 31/5545; A61K 31/675; A61K 31/704; A61K 31/7048; A61K 31/7068; A61K 33/243; A61K 39/3955; A61K 31/555; A61K 31/658; A61K 45/06; A61K 2300/00; A61P 35/00
See application file for complete search history.

(56) References Cited

U.S. PATENT DOCUMENTS

| | | | |
|---|---|---|---|
| 10,098,867 | B2 | 10/2018 | Javid et al. |
| 11,123,308 | B2 | 9/2021 | Yu et al. |
| 2010/0273895 | A1 | 10/2010 | Stinchcomb et al. |

(Continued)

FOREIGN PATENT DOCUMENTS

| | | |
|---|---|---|
| CN | 108433880 A | 8/2018 |
| CN | 110063953 A | 7/2019 |

(Continued)

OTHER PUBLICATIONS

Boretto, M.; Maenhoudt, N.; Luo, X.; Hennes, Aurelie; Boeckx, B.; Bui, B.; Heremans, R.; Perneel, L.; Kobayashi, H,; Van Zundert, I.; Brems, H. Patient-derived organoids from endometrial disease capture clinical heterogeneity and are amendable to drug screening. Nature Cell Biology, 21, 1041-1051. (Year: 2019).*

(Continued)

*Primary Examiner* — Jessica Worsham
(74) *Attorney, Agent, or Firm* — Vos-IP, LLC

(57) ABSTRACT

A method for treating endometrial cancer comprising: administering to a patient a *cannabis* extract (CE) wherein the *cannabis* extract comprises cannabidiol (CBD) at between 50% and 99% by weight of the CE.

18 Claims, 25 Drawing Sheets

(56) References Cited

U.S. PATENT DOCUMENTS

| | | |
|---|---|---|
| 2011/0086113 A1 | 4/2011 | Velasco Diez et al. |
| 2015/0086653 A1 | 3/2015 | Parolaro et al. |
| 2016/0136128 A1 | 5/2016 | Javid et al. |
| 2019/0282513 A1 | 9/2019 | Yerike |
| 2020/0253919 A1 | 8/2020 | Raz et al. |
| 2020/0408740 A1 | 12/2020 | Ballan et al. |
| 2021/0052512 A1 | 2/2021 | Guy et al. |
| 2021/0068444 A1 | 3/2021 | Alarcon et al. |
| 2021/0069608 A1 | 3/2021 | Galyuk |
| 2021/0085638 A1 | 3/2021 | Hospodor |
| 2021/0128521 A1 | 5/2021 | Palaio |
| 2021/0145764 A1 | 5/2021 | Lephart |
| 2022/0000774 A1 | 1/2022 | Dely |
| 2022/0054429 A1 | 2/2022 | Nathan et al. |
| 2022/0062224 A1 | 3/2022 | Gubler et al. |
| 2022/0193164 A1 | 6/2022 | White |
| 2022/0202765 A1 | 6/2022 | Altman et al. |
| 2022/0248619 A1 | 8/2022 | Kleidon |
| 2022/0253919 A1 | 8/2022 | Denner |
| 2022/0331287 A1 | 10/2022 | Morgan et al. |
| 2023/0015268 A1 | 1/2023 | Altman et al. |
| 2023/0127098 A1 | 4/2023 | Capano et al. |
| 2023/0132189 A1 | 4/2023 | Capano et al. |
| 2023/0248747 A1 | 8/2023 | Altman et al. |
| 2023/0355645 A1 | 11/2023 | Storch et al. |

FOREIGN PATENT DOCUMENTS

| | | |
|---|---|---|
| EP | 3368024 A1 | 9/2018 |
| EP | 3449992 A1 | 3/2019 |
| EP | 3544598 A1 | 10/2019 |
| EP | 3915550 A1 | 12/2021 |
| EP | 3937914 A1 | 1/2022 |
| GB | 2516335 A | 1/2015 |
| RU | 2745687 C1 | 3/2021 |
| WO | WO/2013/165251 A1 | 11/2013 |
| WO | WO/2014/057067 A1 | 4/2014 |
| WO | WO/2016/187679 A1 | 12/2016 |
| WO | WO/2017/072773 A1 | 5/2017 |
| WO | WO/2018/167038 A1 | 9/2018 |
| WO | WO/2019/003163 A2 | 1/2019 |
| WO | WO/2019/034113 A1 | 2/2019 |
| WO | WO/2019/106652 A1 | 6/2019 |
| WO | WO/2019/145552 A1 | 8/2019 |
| WO | WO/2019/195943 A1 | 10/2019 |
| WO | WO/2019/222459 A1 | 11/2019 |
| WO | WO/2020/036655 A9 | 2/2020 |
| WO | WO/2020/163775 A1 | 8/2020 |
| WO | WO/2020/165878 A1 | 8/2020 |
| WO | WO/2020/183455 A1 | 9/2020 |
| WO | WO/2020/194237 A1 | 10/2020 |
| WO | WO/2020/209902 A1 | 10/2020 |
| WO | WO/2021/011790 A1 | 1/2021 |
| WO | WO/2021/016718 A1 | 2/2021 |
| WO | WO/2021/028646 A1 | 2/2021 |
| WO | WO/2021/099792 A1 | 5/2021 |
| WO | WO/2021/130728 A1 | 7/2021 |
| WO | WO/2021/158251 A1 | 8/2021 |
| WO | WO/2021/235977 A1 | 11/2021 |
| WO | WO/2021/240510 A1 | 12/2021 |
| WO | WO/2021/245522 A1 | 12/2021 |
| WO | WO/2022/013854 A1 | 1/2022 |
| WO | WO/2022/016160 A1 | 1/2022 |
| WO | WO/2022/018708 A1 | 1/2022 |
| WO | WO/2022/105952 A1 | 5/2022 |
| WO | WO/2022/118303 A1 | 6/2022 |
| WO | WO/2022/144878 A1 | 7/2022 |
| WO | WO/2022/165349 A1 | 8/2022 |
| WO | WO/2022/165439 A1 | 8/2022 |
| WO | WO/2022/201043 A1 | 9/2022 |
| WO | WO/2022/215071 A1 | 10/2022 |
| WO | WO/2022/225658 A1 | 10/2022 |
| WO | WO/2023/287742 A1 | 1/2023 |
| WO | WO/2023/014818 A2 | 2/2023 |
| WO | WO/2023/062634 A1 | 4/2023 |

OTHER PUBLICATIONS

Midatech Pharma US Inc., Soltamox® Product Label, Revised Apr. 2019.

Olivas-Aguirre, et al., "Tamoxifen Sensitizes Acute Lymphoblastic Leukemia Cells to Cannabidiol by Targeting Cyclophilin-D and Altering Mitochondrial $Ca^2$ Homeostasis", International Journal of Molecular Sciences, vol. 22, No. 16, Aug. 13, 2021, 1-14.

Van Weelden, et al., "Anti-Estrogen Treatment in Endometrial Cancer: A Systematic Review", Frontiers in Oncology, vol. 9, art. 359, May 7, 2019, 1-12.

International Search Report issued in International Application No. PCT/US2022/078698 dated Dec. 14, 2022.

International Search Report issued in International Application No. PCT/US2022/078701 dated Feb. 15, 2023.

International Search Report issued in International Application No. PCT/US2022/078691 dated Jan. 30, 2023.

International Search Report issued in International Application No. PCT/US2022/078693 dated Jan. 30, 2023.

International Search Report issued in International Application No. PCT/US2022/078694 dated Jun. 9, 2023.

Armour, et al., "Self-Management Strategies Amongst Australian Women With Endometriosis: A National Online Survey", BMC Complementary and Alternative Medicine, vol. 19, No. 1, art. 17, Jan. 15, 2019, 1-8.

Escudero-Lara, et al., "Disease-Modifying Effects of Natural $\Delta^9$-Tetrahydrocannabinol in Endometriosis-Associated Pain", eLife, vol. 9, art. e50356, Jan. 14, 2020, https://elifesciences.org/articles/50356.

Fonseca, et al., "Cannabinoid-Induced Cell Death in Endometrial Cancer Cells: Involvement of TRPV1 Receptors in Apoptosis", Journal of Physiology and Biochemistry, vol. 74, No. 2, Feb. 13, 2018, 261-272.

Fraguas-Sánchez, et al., "Enhancing Ovarian Cancer Conventional Chemotherapy Through the Combination With Cannabidiol Loaded Microparticles", European Journal of Pharmaceutics and Biopharmaceutics, vol. 154, Jul. 17, 2020, 246-258.

Go, et al., "Cannabidiol Enhances Cytotoxicity of Anti-Cancer Drugs in Human Head and Neck Squamous Cell Carcinoma", Scientific Reports, vol. 10, No. 1, art. 20622, Nov. 26, 2020, 1-11.

Griffiths, et al., "Cannabidiol Suppresses 3-Dimensional Ovarian Cancer Growth and May Enhance Potency of Classic and Epigenetic Therapies", Gynecologic Oncology, vol. 162, suppl. 1, Abstracts for the 2021 Society of Gynecologic Oncology 52nd Annual Meeting on Women's Cancer, Aug. 18, 2021, S102-S103.

Hazekamp, et al., "Preparative Isolation of Cannabinoids from Cannabis sativa by Centrifugal Partition Chromatography", Journal of Liquid Chromatography & Related Technologies, vol. 27, No. 15, 2004, 2421-2439.

Jaidee, et al., "Kinetics of CBD, Δ9-THC Degradation and Cannabinol Formation in Cannabis Resin at Various Temperature and pH Conditions", Cannabis and Cannabinoid Research, vol. 7, No. 4, Aug. 9, 2022, 1-11.

Jin, et al., "Identification of Chemotypic Markers in Three Chemotype Categories of Cannabis Using Secondary Metabolites Profiled in Inflorescences, Leaves, Stem Bark, and Roots", Frontiers in Plant Science, vol. 12, art. 699530, Jul. 1, 2021, 1-16.

Kenyon, et al., "Report of Objective Clinical Responses of Cancer Patients to Pharmaceutical-Grade Synthetic Cannabidiol", Anticancer Research, vol. 38, No. 10, Oct. 1, 2018, 5831-5835.

Lazarjani, et al., "Processing and Extraction Methods of Medicinal Cannabis: A Narrative Review", Journal of Cannabis Research, vol. 3, art. 32, Jul. 19, 2021, 1-15.

Marinelli, et al., "The Effects of Cannabidiol and Prognostic Role of TRPV2 in Human Endometrial Cancer", International Journal of Molecular Sciences, vol. 21, No. 15, art. 5409, Jul. 29, 2020, 1-22.

Marinotti, et al., "Differentiating Full-Spectrum Hemp Extracts from CBD Isolates: Implications for Policy, Safety and Science", Journal of Dietary Supplements, vol. 17, No. 5, Jun. 16, 2020, 517-526.

(56) References Cited

OTHER PUBLICATIONS

Ökten, et al., "Cannabidiol as a Potential Novel Treatment for Endometriosis by Its Anti-Inflammatory and Anti-Oxidative Effects in an Experimental Rat Model", Human Reproduction, vol. 37, issue supp. 1, Jun. 30, 2022, i111.
Rais, et al., "Phytochemicals in the Treatment of Ovarian Cancer", Frontiers in Bioscience-Elite, vol. 9, No. 1, Jan. 1, 2017, 67-75.
Rush, et al., "Cannabidiol: Assessing Activity in Ovarian and Endometrial Carcinoma Cell Lines", Abstracts for the 2021 Society of Gynecologic Oncology 52nd Annual Meeting on Women's Cancer, Featured Posters 188—Poster Session, vol. 162, suppl. 1, Aug. 1, 2021, https://doi.org/10.1016/S0090-8258(21)00839-8.
Sumanasekera, et al., "Hemp Extract With Specific Anti-Cancer Properties Against Ovarian Cancer", The FASEB Journal Special Issue: Experimental Biology 2021 Meeting Abstracts, vol. 35, No. S1, May 14, 2021, https://doi.org/10.1096/fasebj.2021.35.S1.02877.

\* cited by examiner

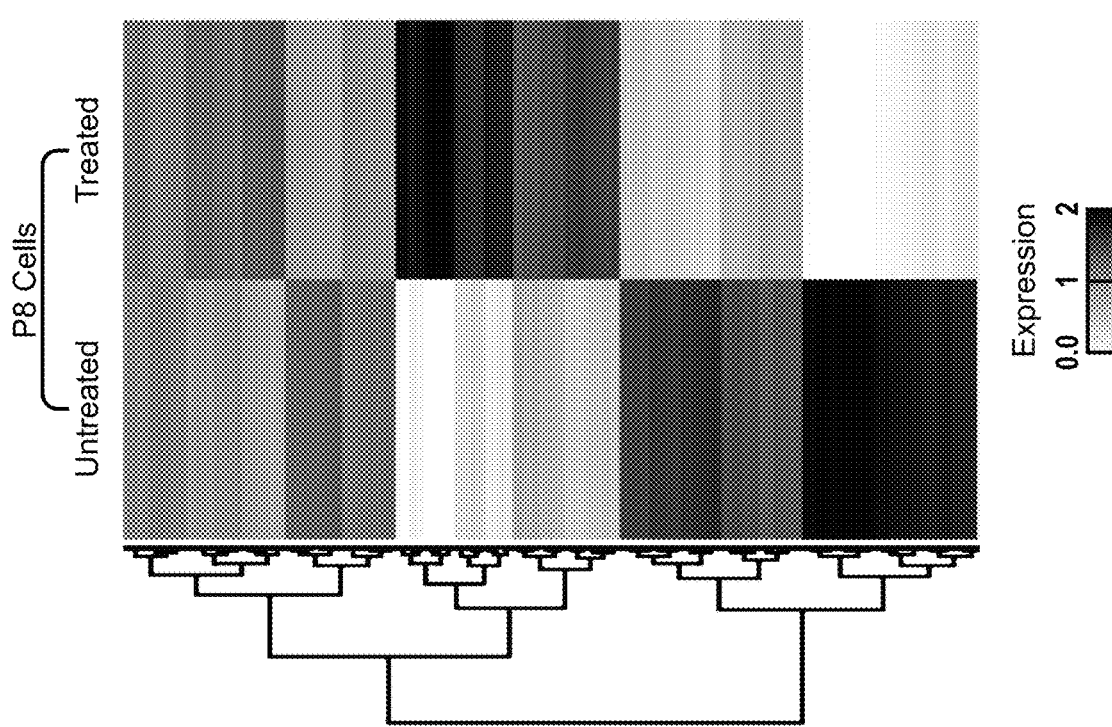
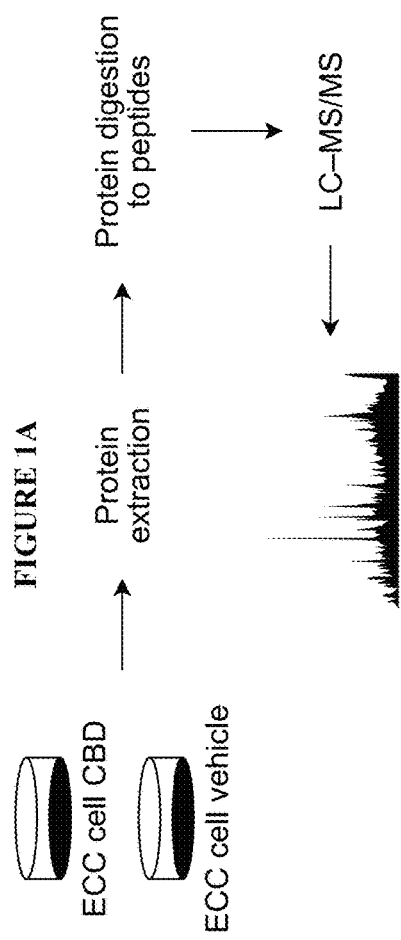
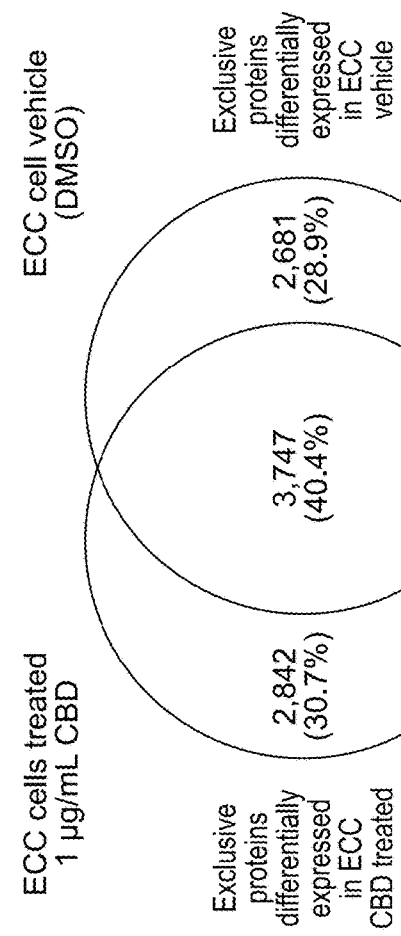

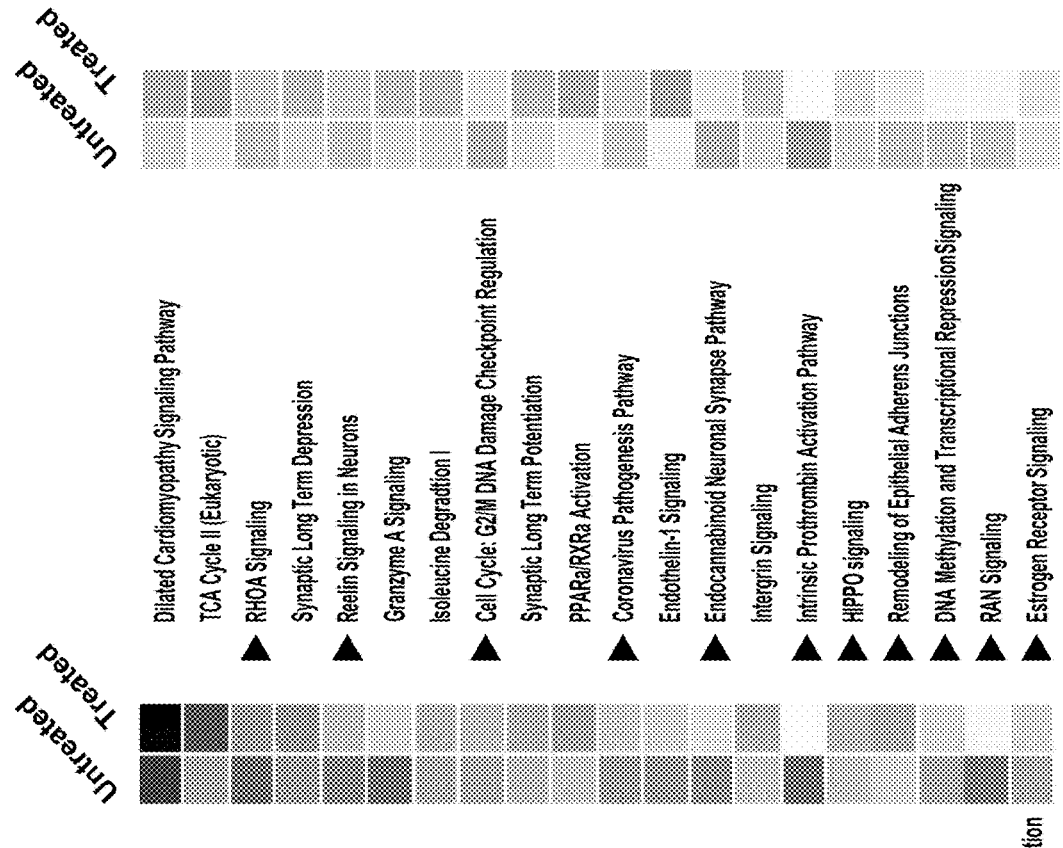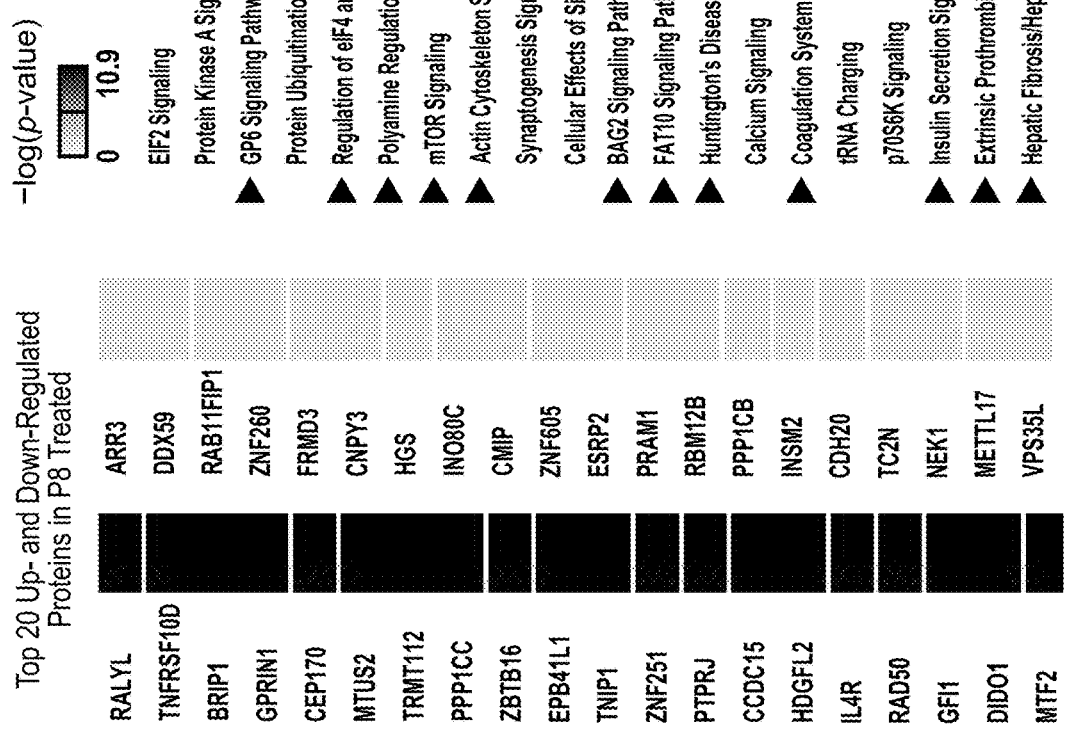

Cannabinoid Receptor 2 Protein Expression in Endometrial Cancer Patient Samples

Endometrial Cancer (Endometrioid Type)

Cannabinoid Receptor 1 Protein Expression in Endometrial Cancer Patient Samples

Endometrial Cancer (Endometrioid Type)

Human Endometrial Cancer Organoids Treated with Different Doses of CBD

High Grade Endometrial Cancer Treated with Different Doses of CBD

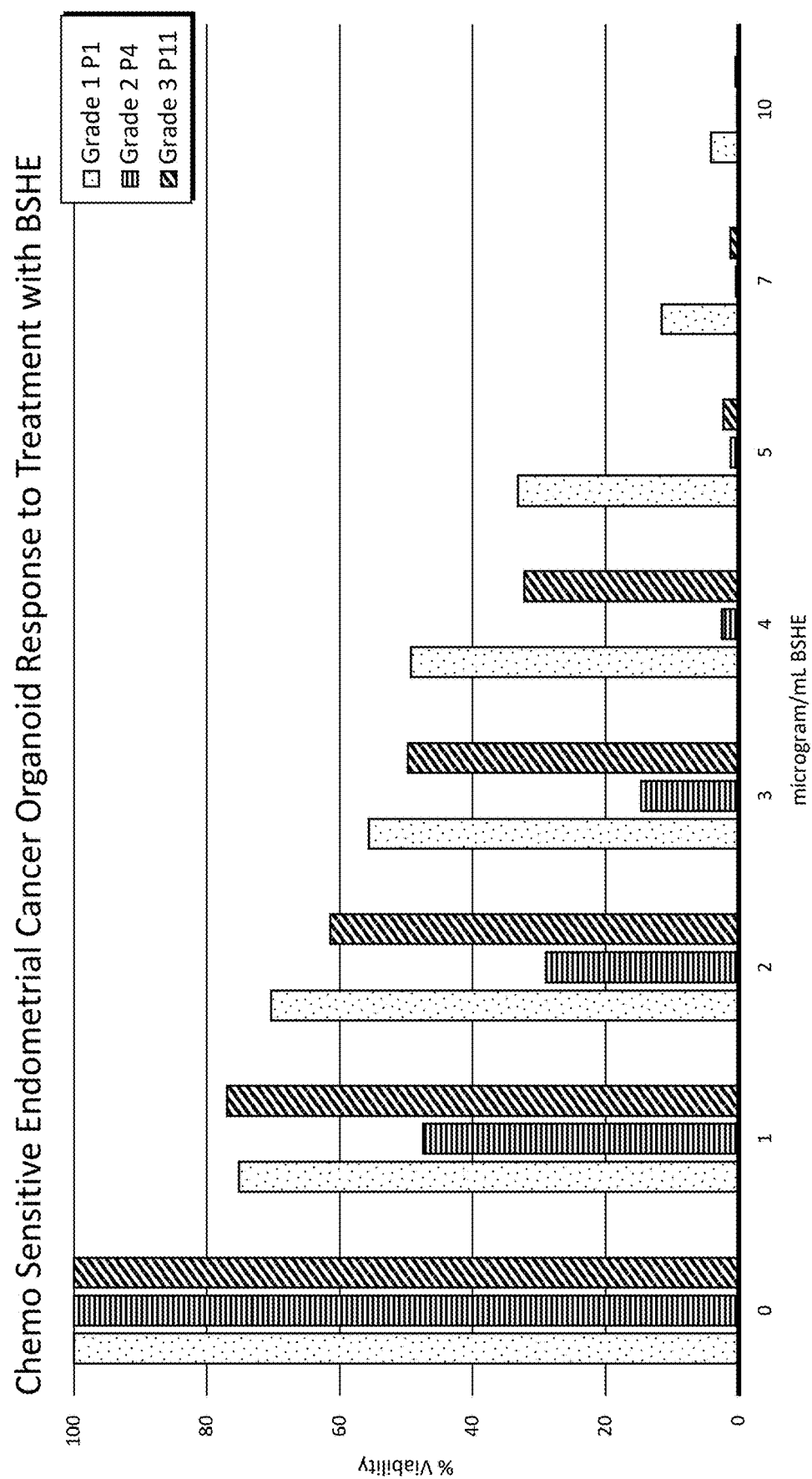

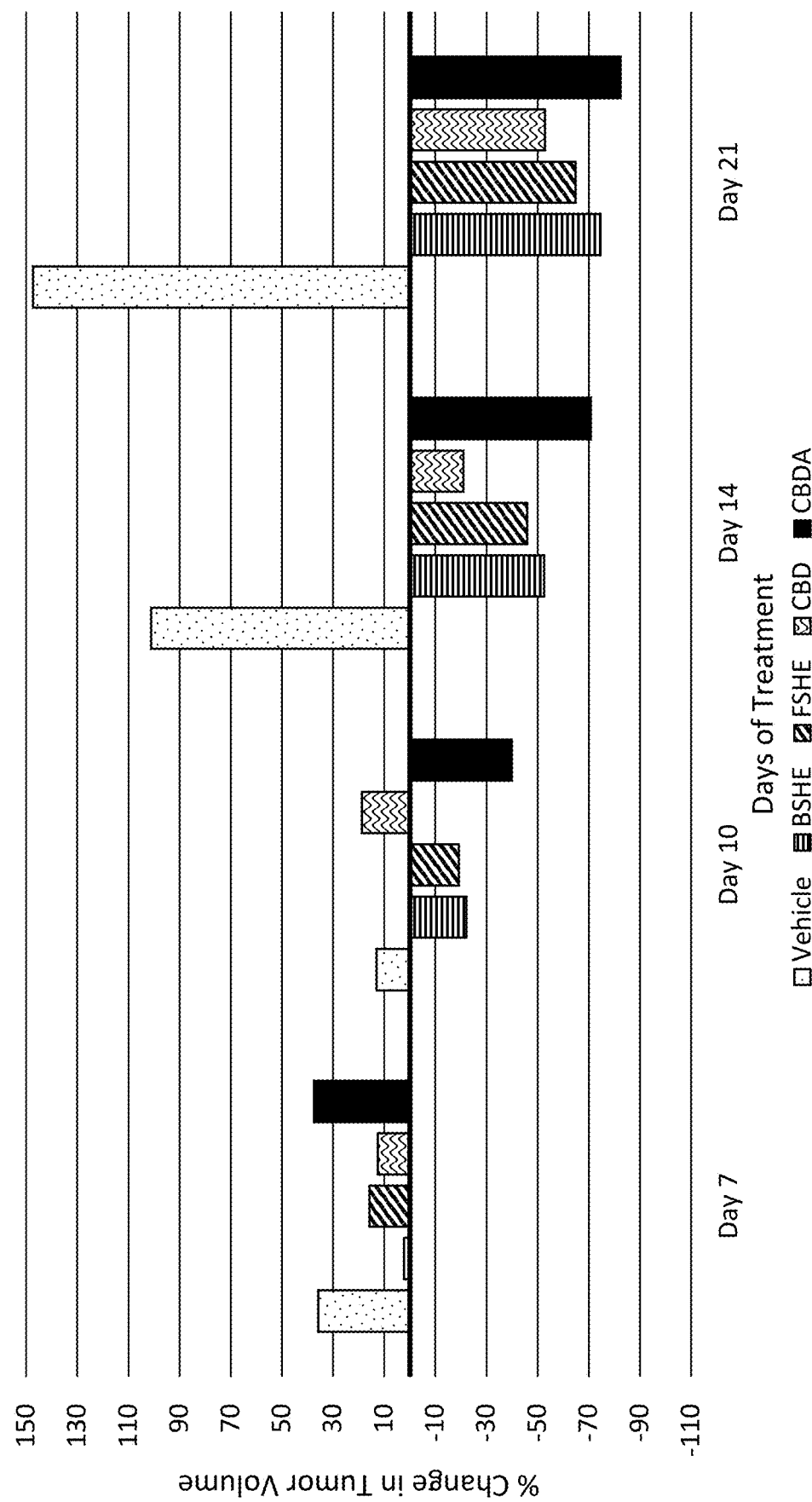

Effects of Paclitaxel and Cannabis Extracts (IC50) + Paclitaxel on Grade 2 Endometrial Cancer Organoids Effects of Paclitaxel and Paclitaxel + Cannabis Extract (IC50) on Grade 3 Endometrial Cancer Tumor Cells

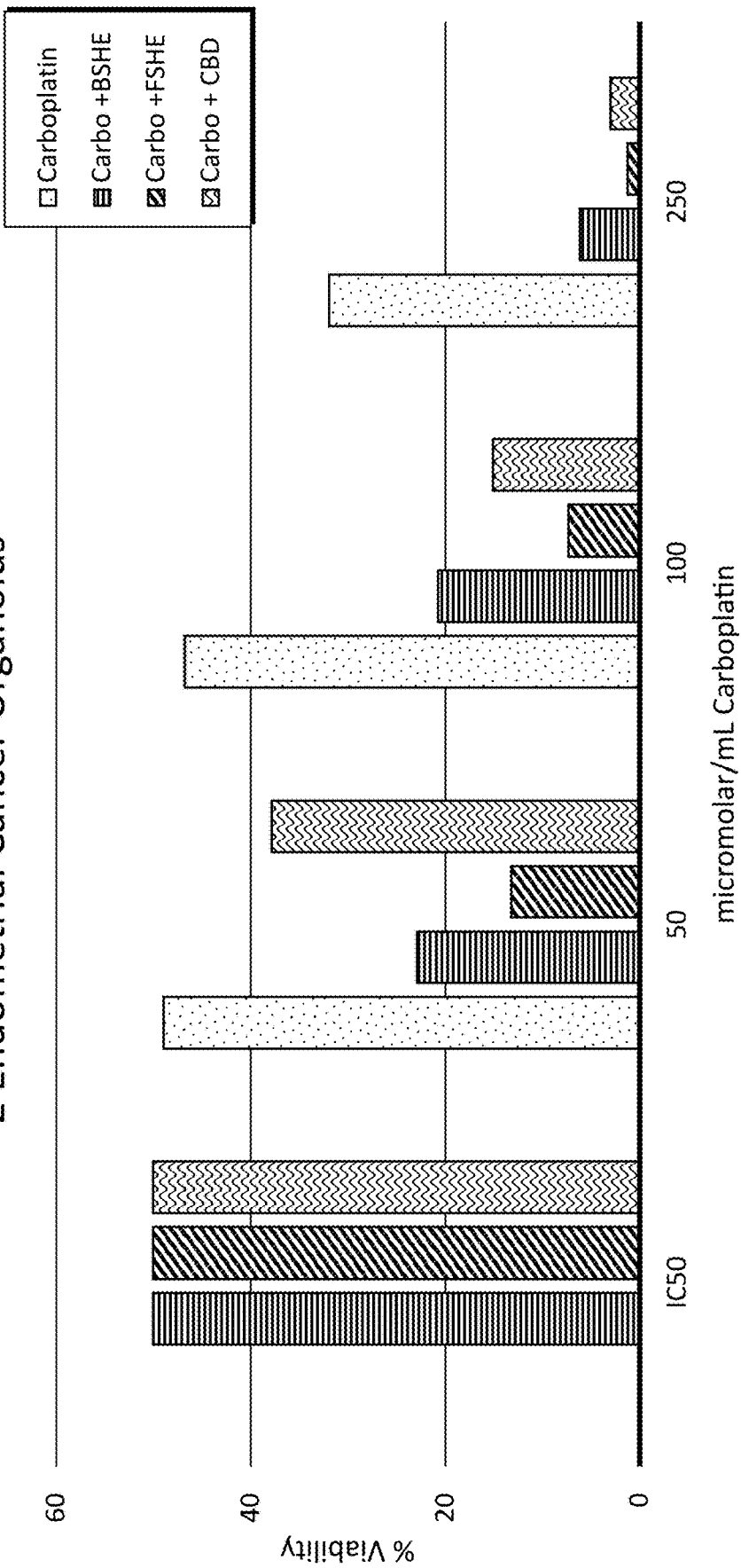

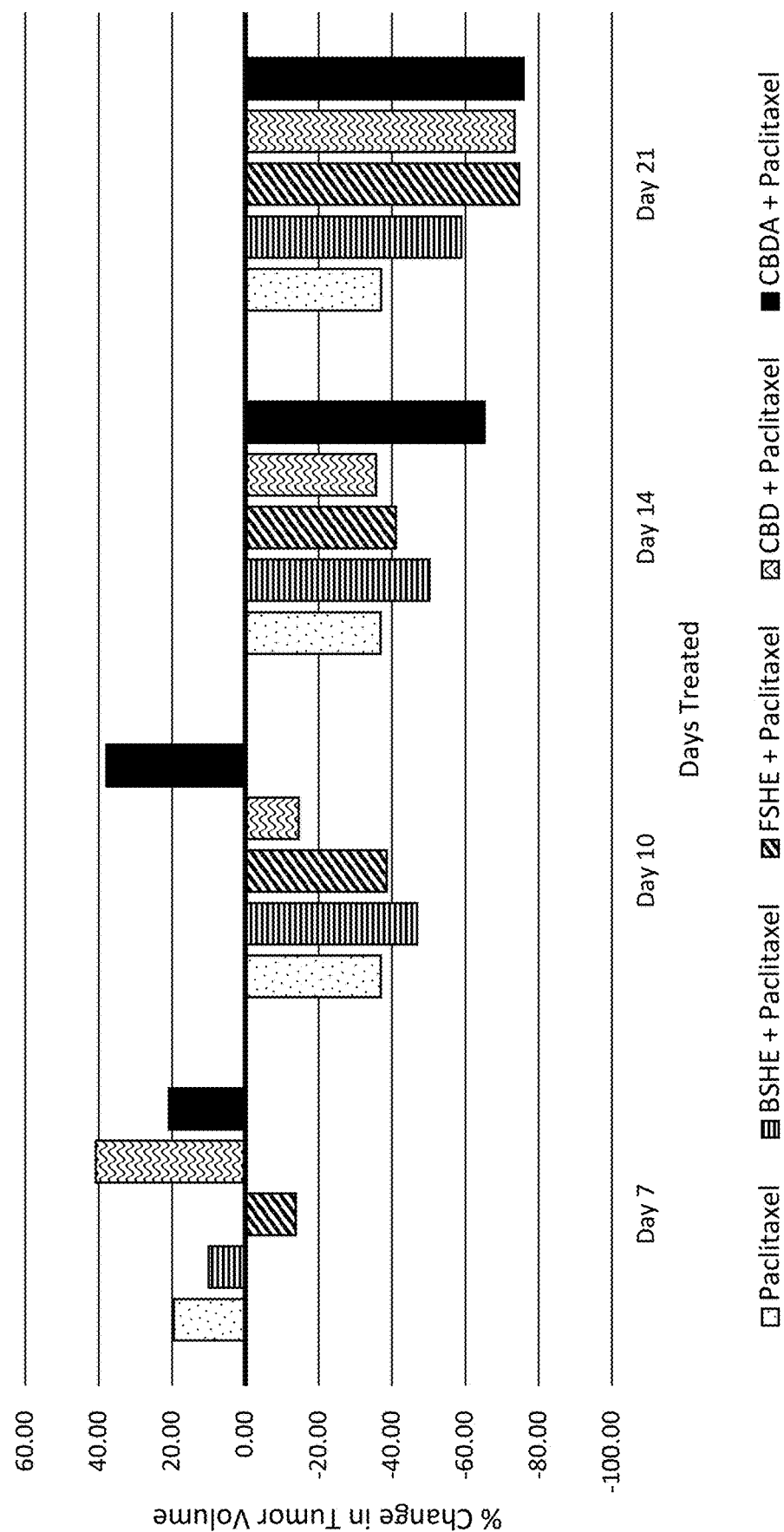

Effects pH and Cannabinoid Extract (10 μg/mL) on Ovarian Cancer Organoid Viability

METHODS OF TREATING ENDOMETRIAL CANCER USING HEMP EXTRACT

CROSS-REFERENCE TO RELATED APPLICATIONS

This application is a continuation of U.S. patent application Ser. No. 18/050,021 filed on Oct. 26, 2022, which claims the benefit of U.S. Provisional Patent Application No. 63/263,018 filed on Oct. 26, 2021, U.S. Provisional Patent Application No. 63/263,026 filed on Oct. 26, 2021, and U.S. Provisional Patent Application No. 63/263,020 filed on Oct. 26, 2021, with the United States Patent and Trademark Office, the contents of which are incorporated herein by reference in their entirety.

FIELD OF THE INVENTION

The inventions disclosed herein are related to compositions and therapeutic treatments of endometrial cancers, through administration of an effective amount of *cannabis* extracts alone or in combination with a chemotherapeutic agent. The *cannabis* extracts comprise one or more cannabinoids, and specifically therapeutic amounts of cannabidiol (CBD) and often include one or more additional cannabinoid, terpene, or other molecules within the *cannabis* extract.

BACKGROUND OF THE INVENTION

Being diagnosed with cancer may feel like being handed a death sentence. Many times it is. And where it is not, the harshness of treatment with chemotherapy and/or radiation may make a patient question the wisdom of undergoing the treatment as opposed to succumbing to the disease. This is especially when the treatment fails and/or does so much damage to the patient's body that it ultimately leads to a death. In fact, a recent inquiry into chemotherapy-related deaths showed that nearly ½ (i.e., 43%) of the patients that died within 30 days of receiving chemotherapy had significant treatment related toxicity. This toxicity was believed to be the cause of death for at least a portion of the patients rather than the cancer itself. In other words, it was believed that about ¼ of the patients in the inquiry died earlier due to treatment than they would have if the cancer were left untreated.

EC is one of the most frequently diagnosed gynecological cancers worldwide, and its prevalence has increased by more than 50% over the last two decades. Endometrial cancer, also called endometrial carcinoma, starts in the cells of the inner lining of the uterus, which is the endometrium. Because there may be few, if any symptoms of EC, or because the symptoms may be masked by a woman's normal reproductive cycle including menopause, some women miss early signs of EC and only discover the disease at its later stages. Other patients, however, present with abnormal uterine bleeding, which may result in an early diagnosis of the disease. Once detected, EC treatment is almost always surgical removal of the cancerous tissue or the entire uterus (i.e., hysterectomy). Many times, patients are advised to have a total or radical hysterectomy and to have their fallopian tubes and ovaries also removed (bilateral salpingo-oophorectomy). Thereafter patients may opt for chemotherapy, radiation therapy, another adjuvant therapy, or combinations thereof. Early detection of EC may prevent the need for chemotherapy or radiation therapy, as the cancer is contained in the uterus. However, EC is quite nefarious and even with early stage diagnosis and tissue/organ removal, a few missed cells can migrate from the uterus allowing for proliferation of the diseased tissues. In this instance, chemotherapy is warranted even though the cancer was found at an early stage and the diseased tissue has been removed. Furthermore, while primary surgical treatment is beneficial in most cases, about 15-20% of patients develop recurrent disease even if no symptoms of advanced metastatic disease are present at the time of EC diagnosis. Specifically, per the International Federal of Gynecology and Obstetrics (FIGO), the chance of recurrence in stage I-II ECs is 10-20% whereas recurrence in stage III-IV ECs is 50-70%.

Accordingly, there is a need for EC treatments that improve the primary treatment, i.e., destroying the EC cells and reducing EC cell loads, which in turn may reduce the chances of metastasis within the body; and reducing tumor size for any unresected tumors. Each of the forgoing having the ultimate goal of extending life expectancy either through EC remission or tumor management, while reducing the secondary effects of treatment, so as to increase quality of life. Any of these outcomes may signify a successful treatment in one or more patients.

Thus, there continues to be a need for EC treatment options, especially treatment options that are less toxic/damaging to healthy cells/tissues than chemotherapy while still being able to eradicate the diseased cells/tissues at least as well as chemotherapy or in combination with chemotherapy.

SUMMARY

In an embodiment, the present invention provides a *cannabis* extract for use in a method of treating endometrial cancer in a patient, wherein said *cannabis* extract comprises cannabidiol (CBD).

In an embodiment, the present invention provides an intravaginal composition for use in a method of treating endometrial cancer in a patient, wherein said intravaginal composition comprises a *cannabis* extract comprising cannabidiol, and a pharmaceutically acceptable excipient.

In an embodiment, the present invention provides a *cannabis* extract for use in a method of treating endometrial cancer in a patient, wherein said *cannabis* extract comprises cannabidiol (CBD) and wherein said method is a method for concurrently treating endometrial cancer and endometriosis, and the method comprises administering the *cannabis* extract to the patient concomitantly via an oral formulation and via an intravaginal formulation. As defined herein, the term "concomitantly" means that the oral formulation and the intravaginal formulation are administered to the patient no more than 72 hours apart, preferably no more than 48 hours apart, and more preferably no more than 24 hours apart, for example no more than 12 hours apart, no more than 6 hours apart, no more than 4 hours, apart, no more than 3 hours apart, no more than 2 hours apart, no more than an hour apart, no more than 30 minutes apart, or simultaneously. Thus, in an embodiment, the present invention provides an oral formulation for use in a method for concurrently treating endometrial cancer and endometriosis, wherein said oral formulation comprises a *cannabis* extract comprising cannabidiol (CBD) and a pharmaceutically acceptable excipient, and said method comprises administration of the oral formulation concomitantly with an intravaginal formulation comprising a *cannabis* extract comprising cannabidiol (CBD) and a pharmaceutically acceptable excipient. In a further embodiment, the present invention provides an intravaginal formulation for use in a method for concurrently treating endometrial cancer and endometriosis, wherein said intravaginal formulation comprises a *cannabis* extract comprising cannabidiol (CBD) and a pharmaceutically acceptable excipient, and said method comprises administration of the intravaginal formulation concomitantly with an oral formulation comprising a *cannabis* extract comprising cannabidiol (CBD) and a pharmaceutically acceptable excipient.

In an embodiment, the present invention provides a *cannabis* extract for use in a method of treating endometrial cancer, wherein said *cannabis* extract comprises cannabidiol (CBD) and wherein said method comprises coadministering to a patient an effective amount of said *cannabis* extract and an effective amount of a chemotherapeutic agent. As defined herein, the term "coadministering" means that the *cannabis* extract and the chemotherapeutic agent are administered to the patient no more than 72 hours apart, preferably no more than 48 hours apart, and more preferably no more than 24 hours apart, for example no more than 12 hours apart, no more than 6 hours apart, no more than 4 hours, apart, no more than 3 hours apart, no more than 2 hours apart, no more than an hour apart, no more than 30 minutes apart, or simultaneously.

In an embodiment, the present invention provides a chemotherapeutic agent for use in a method of treating endometrial cancer, wherein said method comprises coadministering to a patient an effective amount of said chemotherapeutic agent and an effective amount of a *cannabis* extract, wherein said *cannabis* extract comprises cannabidiol (CBD).

In an embodiment, the present invention provides a pharmaceutical composition for use in a method of treating a gynecological cancer, wherein said pharmaceutical composition comprises a *cannabis* extract and an effective amount of CBD.

In an embodiment, the present invention provides the use of a *cannabis* extract comprising cannabidiol (CBD) in the manufacture of a medicament for use in a method of treating endometrial cancer.

In an embodiment, the present invention provides the use of an intravaginal composition comprising a *cannabis* extract comprising cannabidiol, and a pharmaceutically acceptable excipient, in the manufacture of a medicament for use in a method of treating endometrial cancer.

In an embodiment, the present invention provides the use of a *cannabis* extract comprising cannabidiol (CBD) in the manufacture of a medicament for use in a method of treating endometrial cancer, wherein said *cannabis* extract is coadministered with a chemotherapeutic agent.

In an embodiment, the present invention provides the use of a chemotherapeutic agent in the manufacture of a medicament for use in a method of treating endometrial cancer, wherein said chemotherapeutic agent is coadministered with a *cannabis* extract comprising cannabidiol (CBD).

In an embodiment, the present invention provides the use of a pharmaceutical composition comprising a *cannabis* extract and an effective amount of CBD in the manufacture of a medicament for use in a method of treating a gynecological cancer.

A method of treatment of endometrial cancer comprising, administering to a patient via an intravaginal application, an effective amount of a pharmaceutical composition comprising a *cannabis* extract comprising between 1 and 99.9% CBD.

A method of concurrent treatment of endometriosis and endometrial cancer, comprising administering to a patient via an intravaginal application, an effective amount of a pharmaceutical composition comprising a BSHE or FSHE comprising CBD, and administering to said patient an effective amount of a concomitant oral composition comprising a full spectrum hemp extract (FSHE) or a broad spectrum hemp extract (BSHE) comprising cannabidiol (CBD).

The method of any one of the preceding embodiments, wherein the effective dose is sufficient to generate a concentration of at least 10 µg/mL of the BSHE or FSHE at the target tissue. The method, wherein the target tissue is a cancerous tissue of the female reproductive tract.

In a preferred embodiment, a *cannabis* extract for use in a method of treating endometrial cancer in a patient wherein said *cannabis* extract comprises cannabidiol (CBD).

In a further embodiment, the *cannabis* extract for use wherein said *cannabis* extract is selected from a full spectrum hemp extract (FSHE), a broad spectrum hemp extract (BSHE), a CBD isolate, and cannabidiolic acid (CBDA), optionally wherein the BSHE or FSHE comprises (i) from 50% to 90% by weight of CBD and (ii) at least one other cannabinoid selected from $\Delta$-9-tetrahydrocannabinol ($\Delta^9$-THC), tetrahydrocannabinolic acid (THCA), tetrahydrocannabivarin (THCV), $\Delta$-8-tetrahydrocannabinol ($\Delta^8$-THC), cannabichromene (CBC), cannabichromene acid (CBCA), cannabigerol (CBG), cannabigerol acid (CBGA), cannabidiolic acid (CBDA), cannabidivarin (CBDV), cannabinol (CBN), cannabicyclol (CBL), and combinations thereof.

In a further embodiment, the *cannabis* extract for use wherein said *cannabis* extract comprises between 10 mg and 500 mg CBD per dose.

In a further embodiment, the *cannabis* extract for use wherein: (a) the method comprises administration of the *cannabis* extract to the patient via an oral dose, oral mucosal dose, intravaginal dose, or combinations thereof; and/or (b) the method comprises administration of a dose of the *cannabis* extract to the patient at least once every three days, preferably at least once a day, at least twice a day, or at least three times a day; and/or (c) the method comprises administration of an amount of the *cannabis* extract sufficient to generate a concentration of at least 10 µg/mL of the *cannabis* extract at a target tissue in the patient, preferably wherein the target tissue is a cancerous tissue of a female reproductive tract; and/or (d) the method comprises administration of an amount of the *cannabis* extract sufficient to reach an effective therapeutic level as measured through systemic plasma levels of CBD; and/or (e) the method comprises administration of between 20 mg and 500 mg of CBD to the patient per day; and/or (f) the *cannabis* extract is formulated at an acidic pH, preferably at a pH between 3.5 and 6.

In a further embodiment, the *cannabis* extract for use wherein: (a) the endometrial cancer is a grade 1, grade 2 or grade 3 endometrial cancer; and/or (b) the endometrial cancer is a chemoresistant endometrial cancer.

In a further embodiment, the *cannabis* extract for use wherein said *cannabis* extract comprises between 1% and 99.9% CBD and wherein the method comprises administering the *cannabis* extract to the patient via intravaginal administration, preferably wherein: (a) the *cannabis* extract comprises between 60% and 99.9% CBD; and/or (b) the *cannabis* extract is selected from a full spectrum hemp extract (FSHE), a broad spectrum hemp extract (BSHE), and a CBD isolate; and/or (c) the *cannabis* extract comprises CBDA.

In a preferred embodiment, an intravaginal composition for use in a method of treating endometrial cancer in a patient wherein said intravaginal composition comprises a *cannabis* extract and a pharmaceutically acceptable excipient.

In a further embodiment, the intravaginal composition for use wherein the composition comprises (i) an oil or fat as a carrier and/or (ii) at least one terpene, at least one polyphenol, at least one essential fatty acid, at least one phytonutrient, or a combination thereof, optionally wherein the at least one terpene, at least one polyphenol, at least one essential fatty acid, at least one phytonutrient, or combination thereof make up between 1% and 50% by weight of the total weight of the composition, further optionally wherein: the terpene is selected from β-myrcene, β-caryophyllene, linalool, α-pinene, citral, D-limonene, eucalyptol, and combinations thereof; and/or the polyphenol is selected from a catechin, quercetin, cannflavin A/B/C, rutin, chlorogenic acid, and combinations thereof; and/or the essential fatty acid is selected from an omega 3 acid, an omega 6 acid, an omega 9 acid, and combinations thereof; and/or the phytonutrient is selected from a tocopherol, a sterol, carotene, an aliphatic alcohol, a mineral, and combinations thereof.

In a further embodiment, the intravaginal composition for use wherein: (a) the intravaginal composition comprises a dose of between 25 mg and 500 mg *cannabis* extract, and the method comprises administering the composition to the patient via insertion into the vagina; and/or (b) the method comprises administering at least two doses of the intravaginal composition to the patient per day wherein each dose of the intravaginal composition comprises between 10 mg and 250 mg *cannabis* extract; and/or (c) the intravaginal composition has an acidic pH, preferably a pH between 3.5 and 6.

In a further embodiment, the *cannabis* extract for use wherein said method is a method for concurrently treating endometrial cancer and endometriosis and the method comprises administering the *cannabis* extract to the patient concomitantly via an oral formulation and via an intravaginal formulation, preferably wherein the *cannabis* extract is a full spectrum hemp extract (FSHE) or a broad spectrum hemp extract (BSHE).

In a further embodiment, the *cannabis* extract for use wherein said method comprises coadministering to a patient an effective amount of said *cannabis* extract and an effective amount of a chemotherapeutic agent.

In a preferred embodiment, a chemotherapeutic agent for use in a method of treating endometrial cancer wherein said method comprises coadministering to a patient an effective amount of said chemotherapeutic agent and an effective amount of a *cannabis* extract.

In a further embodiment, the *cannabis* extract for use or the chemotherapeutic agent for use wherein: (a) the chemotherapeutic agent is selected from paclitaxel, docetaxel, cisplatin, carboplatin, and combinations thereof; and/or (b) the endometrial cancer is a chemoresistant cancer; and/or (c) the method comprises a first step of determining chemoresistance of a cancerous tissue in a patient and a subsequent step of administering to the patient an effective amount of the *cannabis* extract and an effective amount of the chemotherapeutic agent upon confirmation of chemoresistance; and/or (d) the effective amount of the chemotherapeutic agent is at least 50% less than an indicated dose of the chemotherapeutic agent when administered in the absence of the *cannabis* extract; and/or (e) the method comprises administering the *cannabis* extract to the patient in an amount of between 20 mg and 500 mg per day.

In a preferred embodiment, a pharmaceutical composition for use in a method of treating a gynecological cancer wherein said pharmaceutical composition comprises a *cannabis* extract and an effective amount of CBD.

In a further embodiment, the pharmaceutical composition for use wherein the composition further comprises: (a) a carrier; and/or (b) at least one additional cannabinoid selected from CBDV, THC, CBG, CBN, CBC, CBDA, and combinations thereof; and/or (c) at least one terpene, preferably wherein the terpene is selected from β-myrcene, β-caryophyllene, linalool, α-pinene, citral, D-limonene, eucalyptol, and combinations thereof; and/or (d) at least one polyphenol, preferably wherein the polyphenol is selected from a catechin, quercetin, cannflavin A/B/C, rutin, chlorogenic acid, and combinations thereof; and/or (e) an essential fatty acid, preferably wherein the essential fatty acid is selected from an omega 3 acid, an omega 6 acid, an omega 9 acid, and combinations thereof; and/or (f) a phytonutrient, preferably wherein the phytonutrient is selected from a tocopherol, a sterol, carotene, an aliphatic alcohol, a mineral, and combinations thereof.

In a preferred embodiment, a method for treating endometrial cancer comprising administering to a patient an effective amount of a composition comprising a *cannabis* extract (CE).

The method wherein the CE comprises between 50% and 99.9% cannabidiol (CBD).

In a further embodiment, the method wherein the CE is selected from the group consisting of: a full spectrum hemp extract (FSHE), a broad spectrum hemp extract (BSHE), a CBD isolate, and a cannabidiolic acid (CBDA) isolate.

In a further embodiment, the method wherein the CE is administered via an oral form, oral mucosal form, intravaginal form, nasal mucosal form, rectal form, injectable form, or combinations thereof.

In a further embodiment, the method wherein the effective amount of the *cannabis* extract comprising CBD comprises between 10 mg and 4,250 mg of CBD per day.

In a further embodiment, the method wherein administration of the CE is a dose given at least once a day, at least twice a day, or at least three times a day.

In a further embodiment, the method wherein the endometrial cancer is a grade 1, grade 2, or grade 3 endometrial cancer. In a further embodiment, the method wherein the endometrial cancer is a chemoresistant endometrial cancer.

In a further embodiment, the method wherein the CE comprises CBDA at a concentration of between 0.1% and 10%.

In a further embodiment, the method wherein the CE is a full spectrum hemp extract (FSHE) and/or a broad spectrum hemp extract (BSHE) and wherein each of the BSHE or FSHE comprises 50% to 99% by weight of CBD and at least one other cannabinoid at a concentration of 0.1% to 10% wherein the at least one other cannabinoid is selected from the group consisting of: $\Delta^9$-THC, THCA, THCV, $\Delta^8$-THC, CBC, CBCA, CBG, CBGA, CBDA, CBDV, CBN, CBL, and combinations thereof.

In a further embodiment, the method wherein the CE comprises CBD at a concentration of between 60% and 99% and at least one other cannabinoid at a concentration of 0.1% to 10% wherein the at least one other cannabinoid is selected from the group consisting of: $\Delta^9$-THC, THCA, THCV, $\Delta^8$-THC, CBC, CBCA, CBG, CBGA, CBDA, CBDV, CBN, CBL, and combinations thereof; and wherein the CE comprises a total concentration of cannabinoids of between 65% and 99%.

In a further embodiment, the method wherein the composition comprises at least one additional compound selected from the group consisting of: a terpene, a polyphenol, an essential fatty acid, a phytonutrient, and combinations thereof; and wherein the at least one additional compound makes up between 0.1% and 50% of the total weight of the composition.

In a further embodiment, the method wherein the composition comprises an oil or a fat as a carrier.

In a further embodiment, the method wherein the effective amount of the composition is an amount sufficient to reach an effective therapeutic level of CBD as measured through systemic plasma levels.

In a further embodiment, the method wherein the composition is administered at an acidic pH. In a further embodiment, the method wherein the acidic pH is between 3.5 and 6.

In a preferred embodiment, a method of treatment of endometrial cancer comprising administering to a patient an effective amount of a chemotherapeutic agent and coadministering an effective amount of a *cannabis* extract (CE).

In a further embodiment, the method wherein the chemotherapeutic agent and the CE are administered as one composition or as two different compositions.

In a further embodiment, the method wherein the chemotherapeutic agent is selected from the group consisting of: paclitaxel, carboplatin, doxorubicin, cisplatin, docetaxel, gemcitabine, capecitabine, and combinations thereof.

In a further embodiment, the method wherein the composition comprising the CE is a composition for oral, rectal, intravaginal, oromucosal, or nasal delivery.

In a further embodiment, the method wherein the effective amount of the oral composition is sufficient to reach an effective therapeutic level as measured through systemic plasma levels of CBD.

In a further embodiment, the method wherein the endometrial cancer is a chemoresistant cancer.

In a further embodiment, the method wherein the effective amount of a chemotherapeutic agent is at least 50% less than an indicated individual dose and wherein the CE is administered at between 20 mg and 4,250 mg per day.

In a further embodiment, the method wherein the *cannabis* extract is administered in a composition at an acidic pH. In a further embodiment, the method wherein the acidic pH is between 3.5 and 6.

In a further embodiment, the method comprising a first step of determining chemoresistance of a cancerous tissue from said patient and administering to the patient an effective amount of the CE upon confirmation of chemoresistance.

In a further embodiment, the method wherein the CE comprises a cannabinoid selected from the group consisting of: $\Delta^9$-THC, THCA, THCV, $\Delta^8$-THC, CBC, CBCA, CBG, CBGA, CBDA, CBDV, CBN, CBL, and combinations thereof.

In a further embodiment, the method further comprising at least one terpene. In a further embodiment, the method wherein the terpene is selected from the group consisting of: β-myrcene, β-caryophyllene, linalool, α-pinene, citral, D-limonene, eucalyptol, and combinations thereof.

In a further embodiment, the method further comprising at least one polyphenol. In a further embodiment, the method wherein the polyphenol is selected from the group consisting of: catechins, quercetin, cannflavin A/B/C, rutin, chlorogenic acid, and combinations thereof.

In a further embodiment, the method further comprising an essential fatty acid selected from the group consisting of: an omega 3, an omega 6, an omega 9, and combinations thereof.

In a further embodiment, the method further comprising a phytonutrient. In a further embodiment, the method wherein the phytonutrient is selected from the group consisting of: a tocopherol, a sterol, carotene, an aliphatic alcohol, a mineral, and combinations thereof.

In a further embodiment, the method wherein the CBD is derived from a phytocannabinoid derived from a *cannabis* extract.

In a preferred embodiment, a method of treating endometrial cancer comprising:
  (a) taking a cancerous cell from a patient and forming an organoid from the cancerous cell;
  (b) performing a screen on the organoid to determine a chemotherapeutic drug capable of reducing the percent of viable organoids by 50% with an IC50 dose of the chemotherapeutic drug; and (c) administering to the patient the chemotherapeutic drug with an effective amount of a composition comprising a *cannabis* extract (CE) having between 50% and 99.9% CBD.

In a preferred embodiment, a method of treating endometrial cancer comprising:
  (a) taking an endometrial cell from a patient and forming at least one organoid from the endometrial cell; (b) performing a screen on the at least one organoid to determine a chemotherapeutic drug responsive to the patient's organoid; and (c) administering to the patient the chemotherapeutic drug with an effective amount of a composition comprising a *cannabis* extract (CE) having between 50% and 99.9% CBD.

In a further embodiment, the method wherein the CE is administered to the patient as an oral form, oromucosal form, nasal form, rectal form, intravaginal form, injectable form, or combinations thereof. In a further embodiment, the method wherein the CE is administered oromucosally and intravaginally.

In a preferred embodiment, a composition for use in a method of treating endometrial cancer wherein the composition comprises between 1% and 99% by weight of a *cannabis* extract (CE).

In a further embodiment, the composition wherein the CE of the composition comprises: (a) a full spectrum hemp extract (FSHE), a broad spectrum hemp extract (BSHE), a CBD isolate, a CBDA isolate, or combinations thereof; and/or (b) wherein the composition comprises a carrier at between 1% and 99% by weight of the composition; and/or (c) wherein the composition further comprises one or more excipients at between 1% and 50% by weight of the composition.

In a preferred embodiment, a composition for treatment of endometrial cancer wherein the composition comprises a *cannabis* extract (CE), wherein the CE comprises between 1% and 100% by weight of the composition and all percentages therein.

In a further embodiment, the composition wherein the CE comprises between 10% and 90% by weight, or between 20% and 90% by weight, and preferably between 40% and 80% by weight of the composition.

In a further embodiment, the composition wherein the CE is preferably a full spectrum hemp extract (FSHE), a broad spectrum hemp extract (BSHE), a CBD isolate, or a CBDA isolate. In a further embodiment, the composition wherein the BSHE and/or the FSHE and/or the CBD isolate and/or the CBDA isolate constitute between 50% and 99.9% by weight of the CE.

In a further embodiment, the composition comprising a carrier at between 1% and 99% by weight of the composition. In a further embodiment, the composition further comprising at least one or more additional excipients.

In a further embodiment, the composition wherein the composition is a mucosal composition.

In a further embodiment, the composition comprising between 20 mg and 4,250 mg of CBD.

In a preferred embodiment, a method of treating endometrial cancer comprising administering to a patient an effective amount of a composition. In a further embodiment, the method wherein the effective amount is between 20 mg and 4,250 mg a day of CBD.

BRIEF DESCRIPTION OF THE FIGURES

FIGS. 1A, 1B, 1C, 1D, 1E, 1F, and 1G depict endometrial cancer cells being treated with a *cannabis* extract comprising CBD, with FIG. 1A showing a diagram of the process of capturing the data regarding protein expression, FIG. 1B depicting protein differentiation numbers; FIG. 1C depicting upregulated and down regulated protein expression in the vehicle and with a *cannabis* extract comprising CBD treatment; FIG. 1D depicting the top 20 up and down regulated proteins in treated endometrial cancer cells; and FIG. 1E depicting the *cannabis* extract's effects on signaling and trafficking of various physiological and pathophysiological pathways. FIG. 1F depicts cannabinoid receptor 1 protein expression in an endometrial cancer sample; and FIG. 1G depicts cannabinoid receptor 2 protein expression in an endometrial cancer sample.

FIG. 4A depicts results for grade 1, and FIG. 4B depicts results for grade 2 endometrial cancer organoids.

FIGS. 7A, 7B, 7C, and 7D, depict chemosensitive endometrial cancer patient derived organoids, being tested against four different *cannabis* extracts, namely a broad spectrum hemp extract (BSHE) (FIG. 7A), a full spectrum hemp extract (FSHE) (FIG. 7B), a CBD isolate (FIG. 7C) and CBDA (FIG. 7D).

FIG. 8 depicts a graphical chart of endometrial cancer tumor volumes within mice, wherein the mice were injected with patient derived endometrial cancer cells. The data shows the change in tumor volume from day 7 to day 21 and depicting the therapeutic efficacy of the various *cannabis* extracts on the tumor volumes.

FIG. 9A relates to a grade 2 endometrial cancer, while FIG. 9B relates to a grade 3 endometrial cancer. Each showing dramatically reduced percent viability with a combined treatment instead of individualized treatments.

FIG. 10 depicts a combined therapy treatment tested on patient derived endometrial cancer organoids, wherein the chemotherapy agent is carboplatin and is administered with three different *cannabis* extracts. The results showing drastically reduced viability for combined therapy, as compared to individualized treatment.

FIG. 11 depicts tumor volume data for mice administered paclitaxel and one of four different *cannabis* extracts, which depicts the synergy related to the combined impact of chemotherapy being combined with the *cannabis* extract. By day 21, the combined therapy results in almost double the change in tumor volume as compared to alone.

DETAILED DESCRIPTION OF THE INVENTION

Figure 1G:
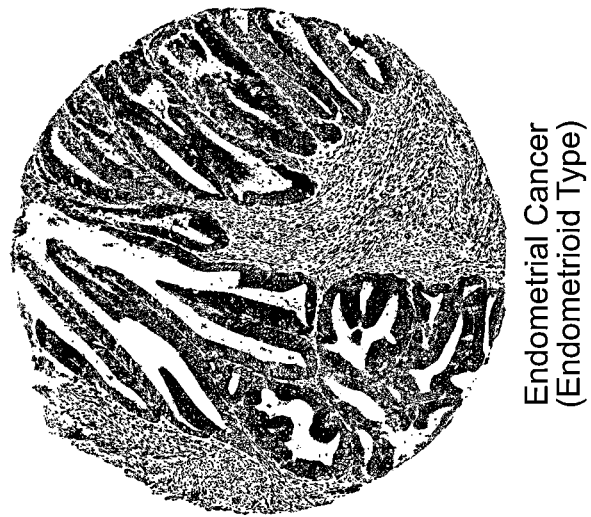

Various embodiments are described more fully hereinafter with reference to the accompanying drawings, which form a part hereof. The embodiments may, however, be embodied in many different forms and should not be construed as limited to the embodiments set forth herein; rather, these embodiments are provided so that this disclosure will be thorough and complete, and will fully convey the scope of the embodiments to those skilled in the art. Among other things, the various embodiments may be therapeutic products, methods of treatment, use of therapeutics in treating the one or more afflictions of endometrial cancer. The following detailed description is, therefore, not to be taken in a limiting sense.

Endometrial Cancer

Most endometrial cancers are categorized as carcinomas, which are cancers that originate in epithelial tissues. Epithelial cells form tissues that line internal and external surfaces of the body. Specialized epithelial cells form glands that secret substances such as sweat, tears, and mucous. Cancers that arise from such glandular tissues are called adenocarcinomas. The most common types of adenocarcinomas are classified as endometrioid cancers. Examples of endometroid cancers include secretory carcinoma, ciliated carcinoma, and villoglandular adenocarcinoma. Another type of epithelial cells are squamous cells. Many people have seen cheek cells, which are a type of squamous epithelial cells. Cancers arising from squamous cells are called squamous cell carcinomas. Some endometrioid cancers include glandular epithelial cells and squamous cells such as adenocarcinoma with squamous differentiation, adenosquamous carcinoma and adenoacanthoma. Other types of endometrial cancers are small cell carcinomas, transitional carcinomas, and serous carcinomas. Less common types of endometrial adenocarcinomas include clear-cell carcinoma, mucinous adenocarcinoma, undifferentiated carcinoma, dedifferentiated carcinoma, and serous adenocarcinoma. The later, less common types of endometrial adenocarcinomas tend to grow and spread faster than most types of endometrial cancers; they often have spread outside the uterus by the time they are diagnosed.

Another type of endometrial cancer is uterine carcinosarcoma or CS. In the past, CS was classified as a sarcoma since it was thought to originate in uterine muscle cells and not epithelial cells. Doctors now believe that CS is an endometrial carcinoma that is so abnormal it no longer looks like the cells it came from—it is poorly differentiated. In fact, although CS starts in the endometrium, it has features of both endometrial carcinoma and sarcoma.

Endometrial cancers can also be characterized by grade and/or stage. Grade is based cancer cell organization such as being organized into glands resembling glands found in a normal, healthy endometrium. In lower-grade cancers, such as grades 1 and 2, more of the cancer cells are organized to form glands. For example, in grade 1 tumors 95% or more of the cancer tissue forms glands and in grade 2 tumors between 50% and 94% of the cancer tissue forms glands. In higher-grade cancers, such as grade 3, the cancer cells are generally disorganized and do not form glands. In fact, in grade 3 tumors less than half of the cancer tissue forms glands. Grade 3 cancers tend to be aggressive growing and spreading fast, and as such have a worse outlook than lower-grade cancers.

Grades 1 and 2 endometrioid cancers are also type 1 endometrial cancers. Type 1 cancers are usually not very aggressive; they do not spread to other tissues quickly. Type 1 endometrial cancers are thought to be caused by excess estrogen and sometimes develop from atypical hyperplasia, an abnormal overgrowth of cells in the endometrium. A small number of endometrial cancers are type 2 endometrial cancer. Type 2 endometrial cancers do not seem to be caused by an excess of estrogen. As compared to type 1 endometrial cancers, type 2 cancers are more likely to grow and spread outside the uterus and they have a poorer outlook. As such, doctors tend to treat type 2 cancers more aggressively than type 1. Examples of type 2 endometrial cancers include all endometrial carcinomas that are not type 1, such as papillary serous carcinoma, clear-cell carcinoma, undifferentiated carcinoma, and grade 3 endometrioid carcinoma. Type 2 endometrial cancers can be poorly differentiated or high-grade and do not look at all like normal endometrium. CS is an example of type 2 endometrial carcinoma. CS tumors are also known as malignant mixed mesodermal tumors or malignant mixed mullerian tumors (MMMTs). They make up about 3% of uterine cancers.

As was mentioned, the first line treatment for EC almost always includes hysterectomy and bilateral salpingo-oophorectomy regardless of grade or stage. In most cases, chemotherapy is recommended after surgery. In view of the significant side effects of chemotherapy, some stage I and II patients may omit or reduce chemotherapy treatment. Chemotherapy, however, is almost always given to stage III and stage IV EC patients. Later stage EC patients are often given several rounds of therapy, with the goal of optimizing the risks and the rewards. The risks include chemotherapy treatment to capture metastatic disease, as endometrial cancer cells have often already migrated from the uterus. Chemotherapy may be viewed as a risk since chemotherapy agents are somewhat indiscriminate in their killing attacking healthy tissues as well as the cancerous tissue. As a result, chemotherapy has significant secondary impacts, including impacts on patient quality and length of life. Indeed, even where the chemotherapy is effective in treating the cancer, the toxic effects of the chemotherapy often prove fatal overtime. Despite these risks, the potential reward is to be cancer-free with a good quality of life.

Chemotherapy is typically given in a cycle, with a drug or combination of drugs given for a period of usually 2-6 weeks. After a rest period, the patient is given another round of treatment. Currently chemotherapies for endometrial cancer treatment including paclitaxel, carboplatin, doxorubicin, cisplatin, docetaxel, gemcitabine, capecitabine, and the combined therapy of carboplatin or cisplatin with paclitaxel, and others. Chemotherapy drugs typically fall into different classes: alkylating agents, antimetabolites, anti-tumor antibiotics, topoisomerase inhibitors, mitotic inhibitors, DNA repair enzyme inhibitors, plant alkaloids, and antineoplastics. The aforementioned therapeutics are classified as follows: paclitaxel and docetaxel are antineoplastic—plant alkaloid; doxorubicin is an antineoplastic—anthracycline antibiotic; carboplatin and cisplatin are platinum-based antineoplastic—alkylating agents; and gemcitabine and capecitabine are antineoplastic, antimetabolites. Frequently, paclitaxel is given in combination with one or more of cisplatin or carboplatin. While over 60% of EC patients initially respond to platinum-based chemotherapy, the majority relapse, becoming "platinum-resistant." Platinum-resistance refers to patients with EC that progresses instead of regressing within six-months of platinum-based therapy. These patients are at the highest risk for disease related mortality even with aggressive treatment and especially if not detected until stage III or IV cancer. At theses stages, EC often metastasizes leading to low survival rates at 2 and 5 years past initial diagnosis and treatment. Because of the risks associated with chemotherapy, including the toxicity to healthy cells as well as the presence of chemoresistant EC, there is a significant need for new therapeutic treatments including ways to reduce or replace chemotherapy.

Efforts have been made to target cell signaling pathways for potential therapeutics. As cancer cells grow uncontrollably, drugs affecting major signaling pathways driving the growth and metastasis of endometrial cancer have been the subject of clinical trials. These trials, however, have reported poor outcomes. It is speculated that the heterogeneous or mixed nature of endometrial cancer is suspected to be one of the key reasons for the failure of targeted therapies. For example, on the molecular level there may be four different subtypes of EC. One subtype includes hypermutated cases with the POLE (e.g., DNA polymerase) gene and 25-30% harboring a microsatellite instability (MSI) phenotype with mismatch repair deficiency (dMMR). Some of these subtypes are treated with PD-1/PD-L1 inhibitors or with immune checkpoint inhibitors, and other molecules such as pembrolizumab or Lenvatinib. These molecules, like first line chemotherapy agents, have high toxicity profiles and thus have significant co-morbidities associated with their use. Furthermore, being targeted, they sometimes miss the heterogeneous nature of the cancer.

Since most EC patients undergo hysterectomy and bi-lateral salpingo-oophorectomy, their EC tissues are available for testing, such as for personalized medicine. For example, resected tumors may be used to determine how tumor growth responds to different chemotherapy drugs. Generally, tumor cells may either respond to chemotherapy (e.g., chemosensitive) or not respond to chemotherapy (e.g., chemoresistant). If the tumor is chemoresistant, then therapeutic treatment may need to be modified if a particular chemotherapy drug was intended for treatment. Additionally or alternatively, upon starting treatment, certain tests may be utilized to confirm the effectiveness of the chemo treatment and at that point, if not before, the patient/cancer can be deemed chemosensitive or chemoresistant. This is an important differentiator as it will impact the efficacy of the treatment where the patient/cancer is deemed to be chemoresistant.

More specifically, with chemoresistance, cancer cells resist the action of a therapeutic agent such that the disease progresses. Chemoresistant disease may still have some clinical response, but not at level that prevents disease progression without resorting to such high doses of chemotherapy to make the treatment unsuitable. Chemosensitive, is therefore the opposite of chemoresistance, where cancer cells are sensitive to the chemotherapy agent, so that the disease is managed or reduced. The characterization of chemosensitive, however, is subject to change; EC may at one point be chemosensitive and become chemoresistant as treatment progresses through a typical on/off cycle for chemotherapy. Indeed, presently, where chemoresistant tumors exist, there are few, if any treatment plans other than palliative care or removal of additional tumors upon identification. Tumor removal, however, becomes nearly impossible when tumors metastasize. Surprisingly, we have found that one or more *cannabis* extracts including CBD effectively act on chemosensitive, chemoresistant, and chemonaive (tumors who have not been contacted with chemotherapy) tumors. The results of which advocate the use of such extracts as an adjunct to chemotherapy, in combination with chemotherapy, and even a superior treatment for EC.

Cannabis Extracts

*Cannabis* extracts have only recently begun detailed study into therapeutic effects for treatment of disease. Two molecules typically found in *cannabis* extracts of highest interest are typically cannabidiol (CBD) and Δ-9 tetrahydrocannabidiol (THC). However, the extracts contain numerous other cannabinoids and to date, scientists have identified at least 144 cannabinoids produced by plants of the genus *cannabis*, including the hemp plant. Hemp is defined in the U.S. as a *cannabis* plant with a $\Delta^9$-THC content of 0.3% or less by dried weight, so it is a political definition and not a scientific definition. The byproducts of hemp plants, including cannabinoids, are federally legal as defined in section 7606 of the 2014 Farm Bill and made permanent in the 2018 Farm Bill. Just a few examples of different cannabinoids include Cannabigerol (CBG), Cannabichromene (CBC), cannabidivarin (CBDV), and Cannabinol (CBN).

*Cannabis* extracts can be derived from one or more *cannabis* plant strains as a source material. Notably, while different strains may produce green material with different proportions of desirable compounds, different growing conditions can impact the precise amounts of each compound even for the same strains. *Cannabis* extracts may include isolates of certain compounds, such as isolated CBD, or may include products that contain a wider variety of cannabinoids and other materials, such as those called a Full spectrum hemp extract (FSHE) and Broad spectrum hemp extract (BSHE), each of which may contain an array of cannabinoids and other phytonutrients such as essential fatty acids, flavonoids, terpenes and essential vitamins and minerals. BSHE is utilized when no detectable $\Delta^9$-tetrahydrocannabinol (THC) is present. FSHE is utilized when some THC remains in the extract. Each of the BSHE and FSHE contain a combination of cannabinoids to offer what is known as the 'entourage effect'—a term created by Ralph Mechoulam to describe the inexplicable synergy that manifests when naturally occurring compounds are consumed in tandem. This effect is thought to be the result of multipathway activation and signaling from various nutrients in the *cannabis* extracts.

The *cannabis* extracts utilized in the present studies are derived primarily from the flower of the plant, the most abundant source of cannabinoids, terpenes, flavonoids, and other bioactive compounds. Other parts of the plant, i.e. the seed or the hurd, may possess some cannabinoids but the most likely source is fall-off from the flower above. *Cannabis* seeds, abundant in other nutrients such as polyunsaturated fatty acids, do not contain cannabinoids at a significant concentration.

A cannabinoid is any one of a diverse class of chemical compounds that influence the endocannabinoid system and elicit responses from cannabinoid receptors (CB1 and CB2 are currently confirmed receptors). These receptors, plus the cannabinoids that activate them, comprise the endocannabinoid system (ECS). There are three primary types of cannabinoids—endocannabinoids, phytocannabinoids, and synthetic cannabinoids. Endocannabinoids also known as endogenous cannabinoids are cannabinoids naturally produced within the body. Phytocannabinoids are cannabinoids produced within plants. Plants that produce cannabinoids include, but are not limited to kava, rosemary, liverwort, electric daisy, *echinacea, cacao, Helichrysum*, pepper trees, black truffles, *cannabis*, as well as a strain of yeast (*Pichia pastoris*). Additionally, certain cannabinoids can be synthesized. Synthetic cannabinoids, however, to date, have shown a greater risk of adverse effects and a lower therapeutic potential, a conclusion shared by multiple systematic reviews comparing safety and tolerability of phytocannabinoids versus synthetic cannabinoids.

While the purpose of cannabinoids in plants remains unclear, the most popular hypothesis suggests they act to protect the plant from insects, bacteria, fungi, ultraviolet radiation, and drying. By contrast, the human body possess an advanced physiological system, known as the endocannabinoid system (ECS). This central regulatory system makes cannabinoids inside the body (endocannabinoids) that foster cellular balance throughout nearly every biological system in the body. The ECS is widely distributed throughout the entirety of human physiology and is comprised of three main parts. These are: (i) cannabinoid receptors (CB1 and CB2); (ii) endogenous cannabinoids (endocannabinoids) and most notably anandamide and 2-AG; and (iii) Enzymes that break down endocannabinoids (FAAH and MAGL). Cannabinoid receptors, found on the surface of cells, are widespread throughout the body and listen to the environment around each cell. They transmit information on current conditions to the cell and thereby jump-start the proper cellular response. Properly functioning cannabinoid receptors have the crucial function of creating homeostasis in the body's cells.

CB1 and CB2 receptors are the predominant receptors in the ECS. CB1 receptors are abundant in the brain and central nervous system, whereas CB2 receptors are sparse in the central nervous system but are common throughout the periphery, primarily on immune cells. Cannabinoid receptors are present in almost every organ and organ system throughout the body. They influence activities in the reproductive system, heart, lungs, brain, blood vessels, GI tract, liver, stomach, and more. Cannabinoids, found in hemp (phytocannabinoids), such as CBD, may influence a wide array of bodily functions. These phytocannabinoids interact with the cannabinoid receptors and modulate their activity—while at the same time boosting levels of endocannabinoids. For example, CBD works with the cannabinoid receptors by inhibiting FAAH (Fatty Acid Amide Hydrolase), an enzyme that breaks down the naturally produced endocannabinoid anandamide, thus prolonging its half-life. Anandamide is partially responsible for regulating human reproduction, among its other implications within the body.

Endocannabinoid receptors are abundant in female reproductive organs and the central nervous system. Their signaling and trafficking influence multiple physiological and pathophysiological functions of female reproduction, including folliculogenesis, oocyte maturation, cytoskeleton rearrangement, endometrial cell motility, endometrial migration & proliferation, decidualization, plasticity, and peripheral innervation. Thus, cannabinoids exert antiproliferative effects on deep infiltrating endometriosis, and increased cannabinoid signaling may reduce proliferation of endometriotic lesions, the etiology of which shares some genetic basis and pathophysiological overlap with ovarian and endometrial cancers. Cannabinoid receptors in the pelvis, ovaries, endometrium, vulva, and the central and peripheral nervous systems influence inflammation, nociception, and arousal at these therapeutic targets. Cannabinoids trigger localized vasodilation and relaxation of pathological smooth muscle contraction and/or spasticity.

Cannabinoid receptors belong to a superfamily of G protein-coupled receptors. They are single polypeptides with seven transmembrane α-helices, and have an extracellular, glycosylated N-terminus and intracellular C-terminus. Both CB1 and CB2 cannabinoid receptors are linked to GI/O proteins. In addition to these receptors, endogenous ligands for these receptors capable of mimicking the pharmacological actions of THC have also been discovered. Such ligands were designated endocannabinoids and included anandamide and 2-arachidonoyl glycerol (2-AG). Anandamide is produced in the brain and peripheral immune tissues such as the spleen.

Unlike THC, which exerts its action by binding to CB1 and CB2, CBD does not readily bind to these receptors and hence has no psychotropic activity. Instead, cannabidiol indirectly stimulates endogenous cannabinoid signaling by suppressing the enzyme that breaks down anandamide (fatty acid amide hydroxylase, "FAAH"). CBD also stimulates the release of 2-AG. Therefore, the mechanisms of action for CBD are complex, varied, and still only partially understood. CBD is an antagonist and a partial allosteric modulator of CB1 receptors. There is evidence that CBD stimulates 5HT1A/2A/3A serotonin receptors, TRPV1-2 vanilloid receptors, and glycine channels. CBD does not bind to either CB1 or CB2 receptors and thus most, if not all, of CBD mechanisms are not directly CB receptor mediated.

Accordingly, CBD may be implicated in signaling pathways in the body. For example, CBD may play a modulatory role with regard to cytokines. Cytokines are signaling proteins synthesized and secreted by immune cells upon stimulation. Accordingly, one of the possible mechanisms of immune control by CBD is by perturbing the balance between cytokines produced by T helper subsets, $T_h1$ and $T_h2$. In certain prior studies, both anti-inflammatory and proinflammatory effects were shown.

During chronic inflammation, IL-6 suppression can decrease tissue injury. Cannabinoids, including CBD and THC have been shown to decrease IL-6, TNFα, GM-CSF, and IFNγ. Accordingly, one or more of CBD or THC may be a necessary component in certain applications when a combined effect is necessary to reduce inflammation and decrease pain. Low doses of THC may be suitable to provide these therapeutic effects in combination with CBD.

CBD is also known to stimulate vanilloid pain receptors (TRPV-1 receptor), which are known to mediate pain perception, inflammation, and body temperature. CBD may also impact certain adenosine receptors, which play a significant role in cardiovascular function and broadly impact anti-inflammatory effects throughout the body as well as regulate and decrease anxiety and depression and increase the sense of well-being.

Uptake of phytocannabinoids within the body is confounded by its physical property. Phytocannabinoids are nearly insoluble in water but are soluble in lipids, alcohol, and nonpolar organic solvents, and can also be suspended in emulsions. These natural cannabinoids are concentrated in a viscous resin that is produced in glandular structures known as trichomes within hemp plants. In addition to cannabinoids, the resin is rich in terpenes, which are largely responsible for the odor of the plants in the *cannabis* family. These materials are also present in additional tissues of the plant, most notably in the flowers and leaves of the plants.

*Cannabis* extracts for therapeutic use in the methods herein, are generated by an extraction process to remove desired materials from the trichomes and other green material from plants within the *cannabis* genus. In the extraction process, a wide variety of cannabinoids have been isolated from the *cannabis* plant, and some have reported 483 identifiable chemical constituents known to exist in the *cannabis* plant, many of which are generated in levels that are below the level of quantitation. However, the *cannabis* extracts utilized herein, preferably utilize *cannabis* strains that having high concentrations of CBD, and the products being generated typically are evaluated based on a CBD content in mg. The *cannabis* extracts further, preferably, comprise certain amounts of array of cannabinoids and other phytonutrients such as essential fatty acids, flavonoids, terpenes and essential vitamins and minerals A representative, non-limiting sample of the *cannabis* extract of the present disclosure comprises concentrations of certain compounds within the following ranges:

TABLE 1

| BSHE | | |
|---|---|---|
| Cannabinoid | mg/g | % |
| $\Delta^8$-THC | ND | 0-1 |
| $\Delta^9$-THC | ND | 0-0.3 |
| $\Delta^9$-THCA | ND | 0-0.3 |
| THCV | ND | ND |
| THCVA | ND | ND |
| CBD | 900 | 70-99 |
| CBDA | ND | 0-2.5 |
| CBC | ND | 0-3.5 |
| CBCA | ND | 0-5.0 |
| CBDV | ND | 0-2.5 |
| CBG | 15 | 0.1-3.5 |
| CBGA | ND | 0-3.5 |
| CBN | 2.0 | 0.01-0.5 |
| Total THC | ND | 0-1.5 |
| Total CBD | 898.49 | 70-99 |
| Total Cannabinoids | 915.63 | 71-99 |
| Sum of additional Cannabinoids | 0 | 0-10 |

TABLE 2

FSHE

| Cannabinoid | mg/g | % |
|---|---|---|
| Δ⁸-THC | ND | 0-3.0 |
| Δ⁹-THC | 25 | 0.3-5.0 |
| Δ⁹-THCA | ND | 0-1.0 |
| CBD | 800 | 65-98 |
| CBC | 19 | 0-3.5 |
| CBDV | 8 | 0-2.5 |
| CBG | 17 | 0.1-3.5 |
| CBN | 1.65 | 0-0.5 |
| Total THC | 25.47 | 0.3-5.0 |
| Total CBD | 799.43 | 65-98 |
| Total Cannabinoids | 869.94 | 65-99.9 |
| Sum of additional Cannabinoids | 0 | 0-10.0 |

Preferably, the formulation has the following fingerprint: A simplified approach to the formulations is that the BSHE includes between 60-95% of a CBD, $\Delta^9$-THC of 0-5%, and additional cannabinoids between 0.1 and 20%. Additional elements include between 0.1 and 20% of various fatty acids and waxes. And, where the BSHE preferably has no detectable $\Delta^9$-THC, a FSHE contrasts that with having detectable $\Delta^9$-THC, usually between 0.01 and 0.3%, though amounts may be higher.

In further preferred embodiments, the additional cannabinoids sum together to comprising between 0.1 and 20% are selected from the group comprising: of $\Delta^9$-THC, THCA, THCV, $\Delta^8$-THC, CBC, CBCA, CBG, CBGA, CBDA, CBDV, CBN, CBL, and combinations thereof. The meaning, therefore, includes one or more of these cannabinoids, but does not exclude additional cannabinoids. In a further preferred embodiment, wherein at least one additional cannabinoid is present in the formulation at between 0.1 and 10%, selected from the group consisting of: $\Delta^8$-THC, $\Delta^9$-THCA, CBDA, CBC, CBDV, CBG, CBGA, CBA, CBN, and combinations thereof.

Given the widespread presence of the ECS in the mammalian body, and particularly in the reproductive system, the effects of a *cannabis* extract (CE) including CBD on endometrial cancer cell protein expression was examined. Proteomics is the large-scale study of proteins, where a proteome is the entire set of proteins produced by the sample under investigation. Proteomes will differ from cell to cell and from time to time. Thus, the comparison of protein expression in untreated cells as compared to treated cells provides insight as to which proteins change expression in the endometrial cancer cells and which proteins remain the same. With this knowledge, additional, targeted research may ensue. Referring to FIG. 1A, endometrial cancer cells (ECC) were either treated with a CE with CBD (1 µg/mL) or left untreated as a control (vehicle). After treatment, proteins were extracted from the test cells and the control cells and digested for analysis by liquid chromatography (LC) tandem mass spectrometry (MS/MS). Referring to FIG. 1B, the Venn diagram shows the results of LC-MS/MS analysis which is that treated cells expressed 2,842 different proteins than untreated cells, untreated cells expressed 2,681 different proteins than treated cells, and treated and untreated both expressed 3,747 common proteins. Clearly, based on protein expression differences, treatment with as little as 1 µg/mL CE with CBD had a clear impact on proteins that were exclusively expressed and proteins that were no longer expressed. FIG. 1C compares the degree to which certain proteins were expressed (or not expressed) in untreated cells and treated cells.

Referring to FIG. 1D, of the thousands of proteins that were differentially expressed with treated and untreated cells, the top 20 upregulated (e.g., in treated cells only) and downregulated (e.g., in untreated cells only), are identified and enumerated. Now referring to FIG. 1E, the effect of treatment with CE with CBD on signaling and trafficking of various physiological and pathophysiological pathways is shown. As one example, proteins associated with Endocannabinoid Neuronal Synapse are shown to be upregulated in untreated cells and downregulated in treated cells. Lastly, referring to FIG. 1F, a tissue sample taken from a patient with endometrial cancer was selectively stained to show CB1 receptor expression. FIG. 1G is a similar tissue sample selectively stained to show CB2 receptor expression.

At about the same time as the above experiments were taking place, the response of organoids derived from endometrial cancers to CE with CBD were also studied. Generally, patients with EC were identified and tumor cells were collected. The EC tumor cells were used to generate patient derived organoids, the method of which is described below in the Methods section. As the name suggests, organoids are miniature structures that emulate organs in all their complexity. They are derived from stem cells collected via biopsies and/or resected healthy tissues or tumors. In culture, they self-organized into three-dimensional tissues that mimic the tissues of the individual patient from which they were derived. That is, organoids have the same genetic instructions as the individual from which they were derived and thus demonstrate identical mutations, proliferation, and disease progression as their human counterpart. Organoids can be made to replicate organs with differentiated cell types or to express selected aspects of identified cells of interest. Unlike traditional cell line models associated with high failure rates in clinical trials, organoids' responses precisely and directly translate to human responses. Organoids are well established and have already transformed medical research in providing breakthroughs in treating cystic fibrosis, pancreatic cancer, diabetes, and other diseases. In a simplified example, imagine organoids as clones of an individual's organ. In essence, it is a living, growing avatar of a distinct patient existing outside the body. The avatar will mimic tumor growth and respond to treatment cancer just as it would inside the body. This personalized replica identifies allows for identification of individualized, targeted treatment in a matter of days. It allows a patient to avoid wasting time and risking toxicity with ineffective therapies.

Figure 2A:
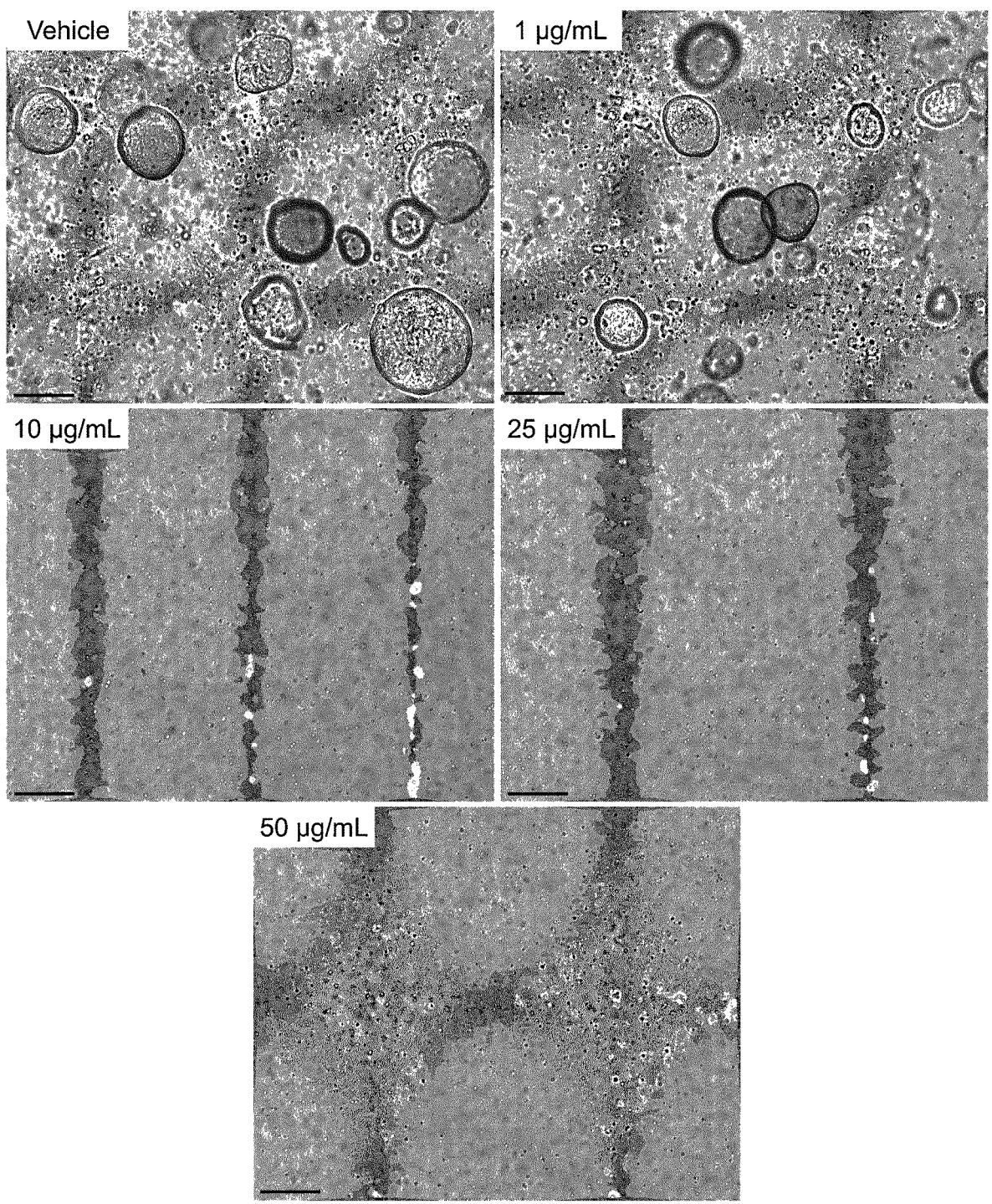
FIGS. 2A and 2B depict endometrial cancer-based organoids treated with a *cannabis* extract, with FIG. 2A depicting cells images treated with varying concentrations of *cannabis* extract as delivered through a BSHE. Notably, FIG. 2B summarizes the results showing a virtual eradication of the endometrial cancer organoids at as low as 10 µg/mL, and all values above.
Figure 2B:
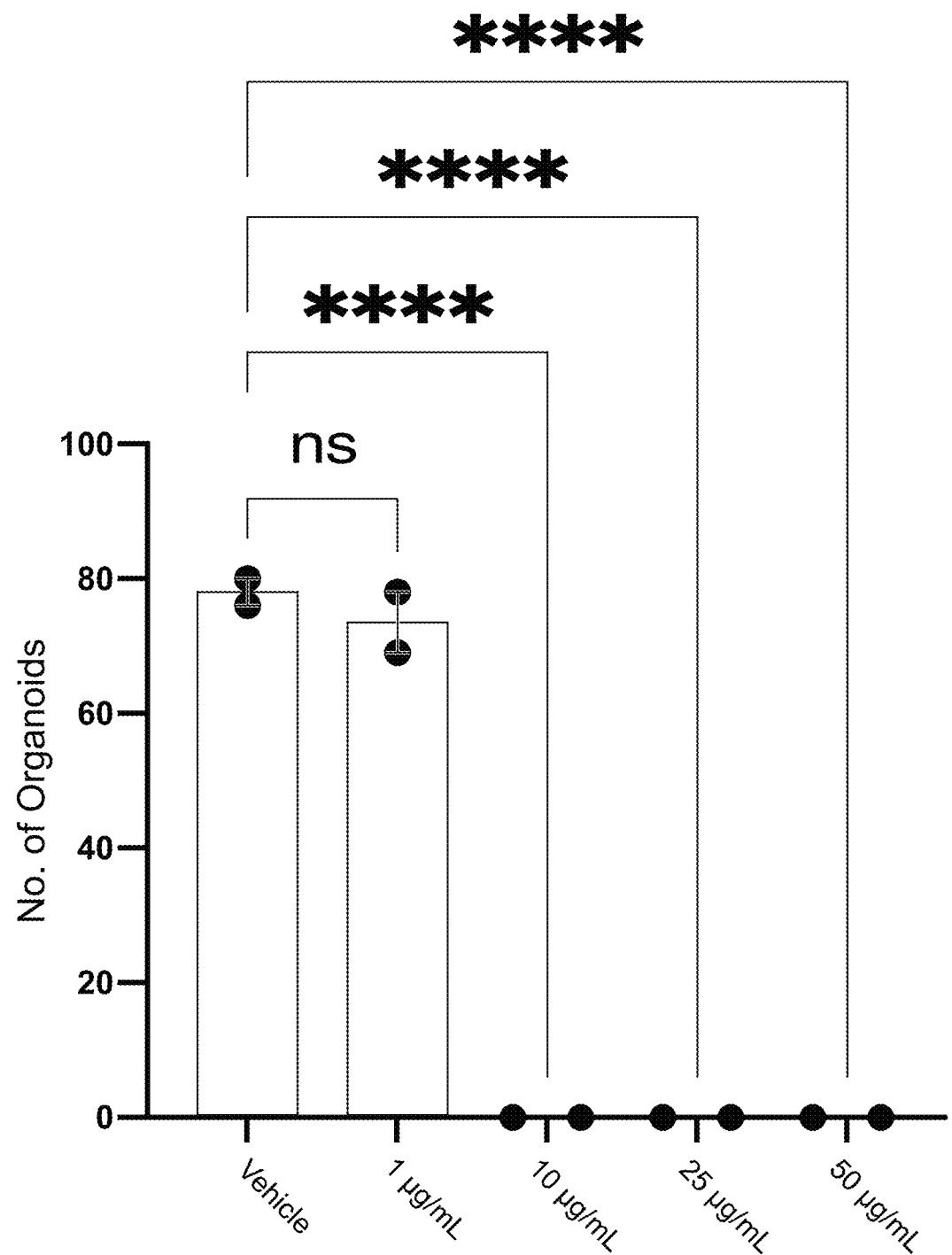

Initial experiments on endometrial cancer organoids derived from grade 1 EC cells used 250 µg/mL of a BSHE comprising CBD as the lowest dose for treatment. This dosage was 100% effective in killing the endometrial cancer organoids, which was certainly unexpected. Subsequent experiments used 100 µg/mL of the BSHE as the lowest dose for treatment. Again, 100 µg/mL was 100% effective in killing the endometrial cancer organoids. Thereafter, endometrial cancer organoids were treated with lower doses of the BSHE, with 50 µg/mL as the highest dose tested. As can be seen in FIG. 2A, the organoids created from grade 1 endometrial cancer were treated with media only, which is the growth media in which the organoids were grown, the vehicle, which is the just the solvent used to deliver the BSHE to the other organoids, and then test dosages of 1 µg/mL, 10 µg/mL, 25 µg/mL, and 50 µg/mL, each concentration being delivered the vehicle. As can be in FIG. 2B (and 2A) the vehicle and the dosage of 1 µg/mL had nearly the same number of organoids. But at a concentration as low as 10 µg/mL BSHE was able to completely kill the EC organoids. The higher doses of BSHE at 25 µg/mL and 50

µg/mL also showed a 100% kill rate of the EC organoids. Each of the tests of FIG. 2 were run at least in triplicate, including the vehicle alone, which was dimethyl sulfoxide (DMSO).

For comparison, the doses in which the organoids were treated convert to human equivalent doses of 0, 20, 200, 500, and 1000 mg a day respectively. Currently prescribed dosages of CBD isolate (in the United States) are between 5 and 50 mg of CBD/kg. An average weight of between 65 and 85 kg (about 143 pounds to about 187 pounds) yields doses of between 325 to 4250 mg a day of CBD. Our actual tests, therefore, range from well below these prescribed doses to about ¼ of the acceptable dose. We believe that the higher end of the human dosing range is fully appropriate in this case (endometrial cancer) as well, which would replicate the experiments performed at 100 µg/mL and higher. Especially as the alternative to such CBD dose is almost always chemotherapy, which has a significantly worse side effect profile at virtually any concentration than the highest doses of CBD.

Figure 3A:
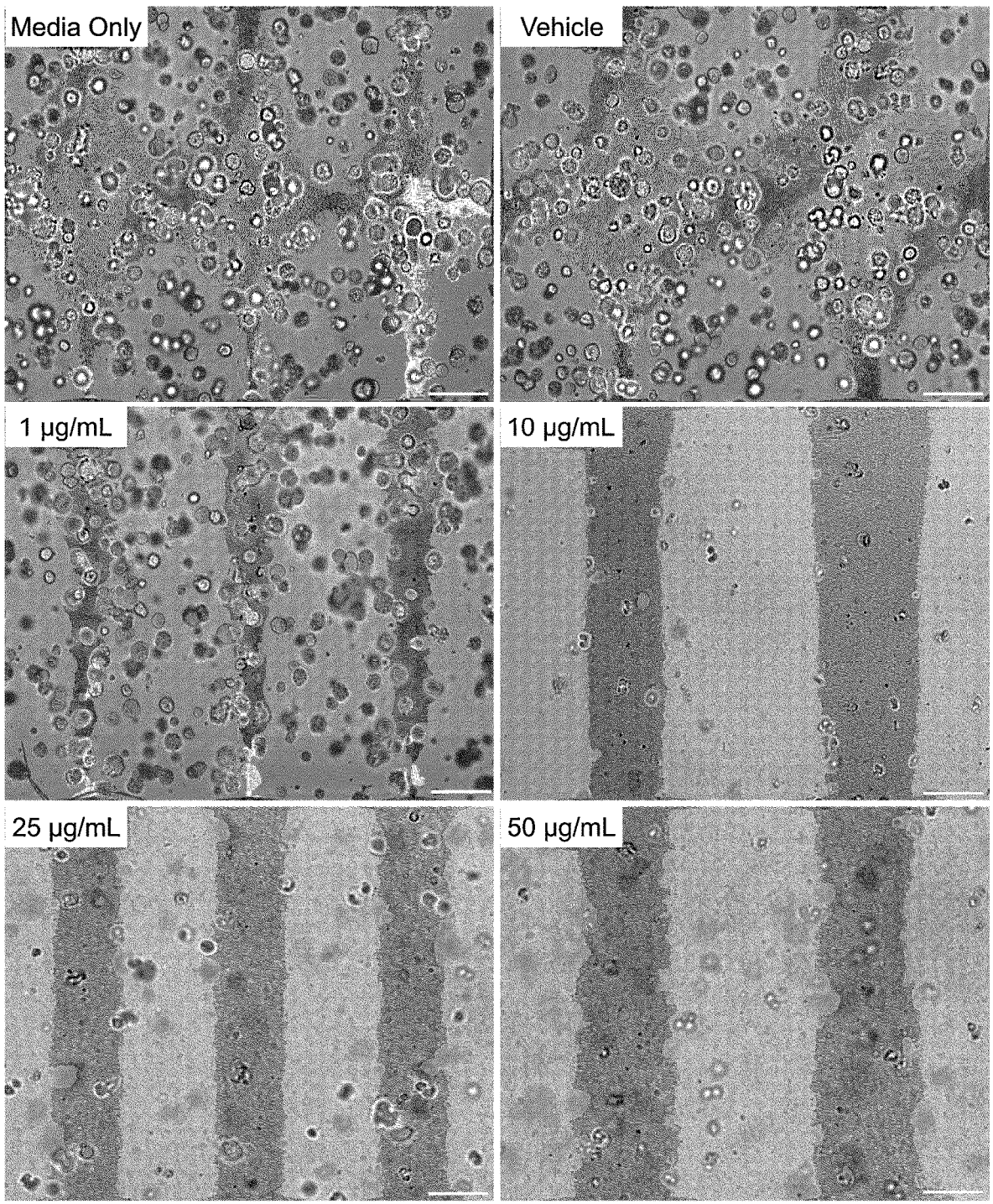
FIGS. 3A and 3B depict high grade endometrial cancer-based organoids treated with a *cannabis* extract, with FIG. 3A depicting cells treated with varying concentrations of *cannabis* extract as delivered through BSHE. Notably, FIG. 3B summarizes the results showing that at 10 µg/mL and higher the organoids are destroyed by the therapeutic treatment.
Figure 3B:
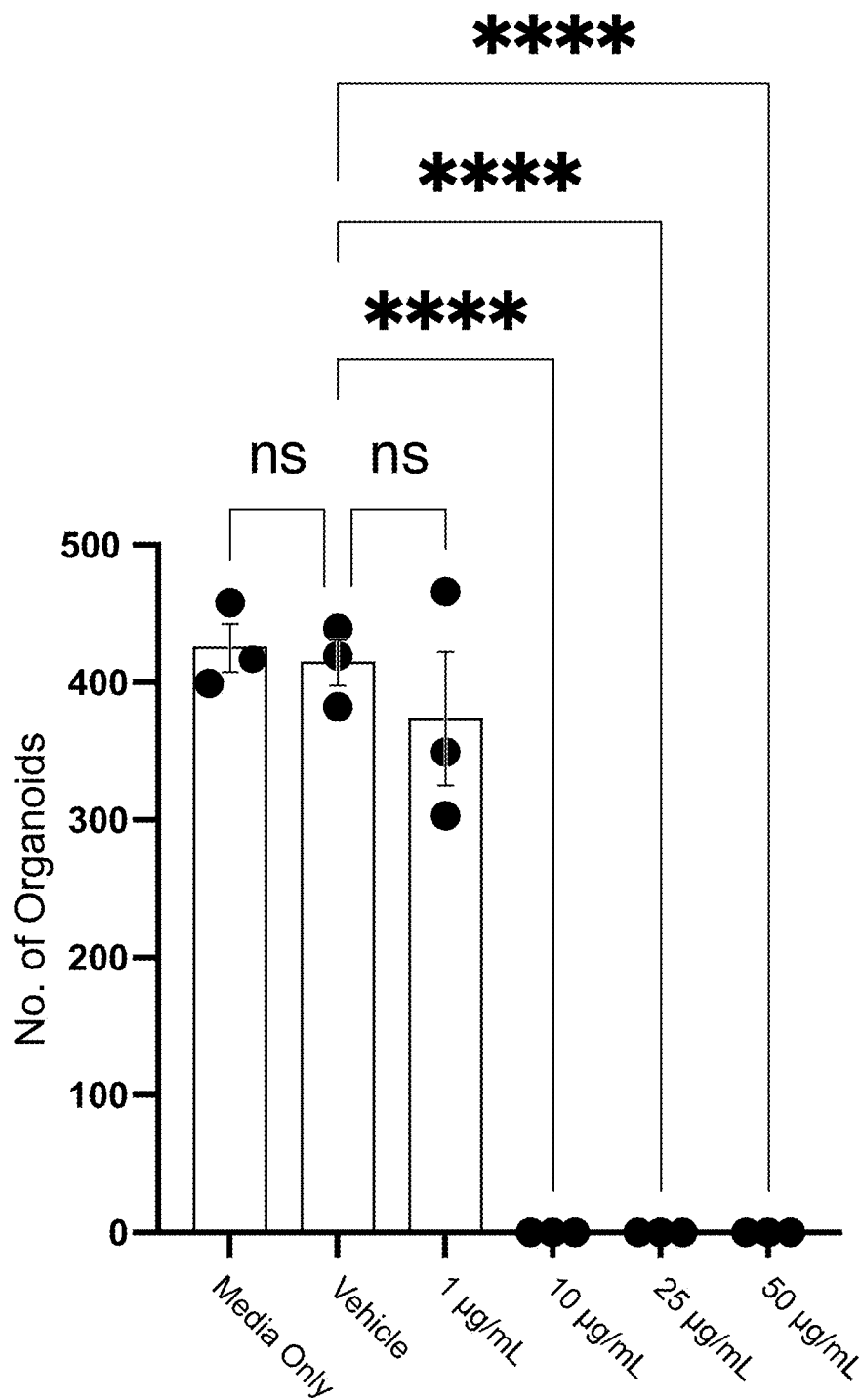

Due to the surprising results of the experiments summarized in FIG. 2, additional experiments were performed on organoids formed from high grade endometrial cancer, the results of which are detailed in FIGS. 3A and 3B. These experiments were essentially the same as the ones previously describe, except for the source of the organoids. Notably, considerably more organoids grew in the media only (showing some of the background material) and DMSO vehicle controls as compared to the controls in lower grade organoid experiments. While 1 µg/mL showed a potential for a small reduction in organoids (evidenced by the data in FIG. 3B), treatment with 10, 25, and 50 µg/mL of the BSHE comprising CBD completely destroyed the growing organoids. In other words, the growth of the organoids from the more aggressive form of endometrial cancer was not simply managed; it was completely reversed. A more surprising result could not have been expected. Thus, the images shown in FIG. 3A and the summary of the data in FIG. 3B paints a complete picture of the successful removal of high grade endometrial cancer organoids by treatment with a *cannabis* extract comprising a quantity of CBD of at least about 10 µg/mL and also with higher concentrations thereof.

Patient with Endometrial Cancer

Soon after the experiments detailed above a 31-year-old Caucasian female came to us. She was diagnosed with endometrial cancer after presenting with significant pain and discomfort. She had already undergone a total hysterectomy and bilateral salpingo-oophorectomy followed by five rounds of chemotherapy. Each of the first five rounds of chemotherapy was a combined chemotherapy with Paclitaxil/Carboplatin. The treatments were ultimately ineffective, and she did not proceed with a sixth round of chemotherapy with these agents due to the ineffectiveness of the prior rounds. Thereafter she was treated with Abemaciclib followed by Atezolizumab, which also failed and resulted in severe adverse effects. As a result of her lack of response to chemotherapy, she was deemed to have chemoresistant endometrial cancer.

When she came to us her endometrial cancer was stage IV and due to the chemoresistance and aggressive nature of the cancer she also had extensive metastatic disease throughout her body. Affected areas included her brain, breasts, heart, stomach, lungs, peritoneum, and lymphatic system. PET scans and other techniques were used to determine the size of metastatic nodes, which ranged from 11×7 mm to 29×10 mm. See, Tables 3 and 4, below. In view of the experiments detailed above, organoids were crafted from the patient's endometrial cancer to assess her response to alternative chemotherapies (after failing seven chemotherapy rounds) in view of her chemoresistance and to the BSHE that was being tested. Her organoids demonstrated a partial response to gemcitabine/capecitabine (GemCap), a combination chemotherapy she had not yet been offered, and a significant response to the BSHE. As such, she began standard protocol GemCap treatment in combination with a regime of 30 mg of BSHE twice daily via oral mucosal delivery and 75 mg of FSHE once daily via intravaginal delivery. Thus, her total daily dose of *cannabis* extract including CBD was 135 mg. After 12 weeks of treatment, a follow up PET scan reported astounding results, which are detailed in Tables 3 and 4.

TABLE 3

A COMPARISON OF THE METABOLIC RESPONSE IN THE PATIENT'S LYMPH NODES BEFORE AND AFTER TREATMENT

| | Before Treatment | | After Treatment | |
|---|---|---|---|---|
| Area | Size | SUV max | Size | SUV |
| Left Supraclavicular | 25 × 16 mm | 18.1 | 7 × 4 mm | No longer measurable on PET |
| Subcarinal | 21 × 14 mm | 16.1 | 9 × 5 mm | No longer measurable on PET |
| Left Hilar | 18 × 10 mm | 10.5 | 8 × 5 mm | No longer measurable on PET |
| Left External Iliac | 15 × 12 mm | 17.8 | 8 × 5 mm | No longer measurable on PET |
| Aorticopulmonary | 29 × 10 mm | 15.1 | No longer measurable on CT or FDG PET | |
| Left internal Mammary | 10 × 8 mm | 9.2 | No longer measurable on CT or FDG PET | |
| Right internal Mammary | 11 × 7 mm | 3.9 | 5 × 3 mm | No longer measurable on PET |
| Left Gastric | 23 × 15 mm | 13.2 | 12 × 7 mm | No longer measurable on PET |
| Left of SMA | 20 × 19 mm | 10.4 | 7 × 4 mm | No longer measurable on PET |

TABLE 4

COMPARISON OF THE METABOLIC RESPONSE IN THE PATIENT'S PULMONARY METASTASES AND PERITONEUM BEFORE AND AFTER TREATMENT

| Area | Before Treatment Size | SUV Max | After Treatment Size | SUV |
|---|---|---|---|---|
| Left Lower lobe Lateral | 18 × 13 mm | 17.9 | 6 × 3 mm | No longer measurable on PET |
| Right Upper lobe Central | 19 × 14 mm | 17.9 | No longer measurable on CT or FDG PET | |
| Peritoneal | 22 × 10 mm | 7.2 | No longer measurable on PET | |

Amazingly, radiology concluded a complete metabolic response to treatment. Notably, significant reductions in the size of metastases were documented. Furthermore, there were no new enlarged or hyper metabolic nodes within the neck, chest, abdomen, pelvis, or inguinal regions to suggest new sites of metastatic adenopathy. And there were no new hypermetabolic pulmonary metastases, no lymphangitis, no pleural or pericardial effusion, no abnormal metabolism in the solid abdominal organs, and no evidence of solid abdominal visceral or metastatic disease on diagnostic CT. Previously demonstrated malignancy ascites in the pelvic region were near completely resolved and there was complete metabolic response in peritoneal deposits. For example, the peritoneum had one of the largest deposits before treatment of 22×10 mm with a SUV max of 7.2 and after treatment was no longer measurable via PET, with no new hypermetabolic peritoneal deposits. Additionally, there were no abnormal metabolism in the brain, no suspicious lesions on the low dose, non-contrast CT, and no abnormal metabolism in bone to suggest osseous metastasis.

Additional results from testing agents on organoids derived from the patent described above are shown in Table 5. The IC50 values were calculated from such tests. This value indicates the dosage at which 50% of the organoids were killed due to treatment. The $C_{max}$ values As can be seen in the table, only a few IC50 values were able to be calculated as the remaining agents did not have enough of an inhibitory effect to be able to determine an IC50 value. In other words, they were not effective at killing the patient's organoids.

TABLE 5

EFFECTS OF VARIOUS AGENTS ON PATIENT DERIVED ORGANOIDS

| Drug | $C_{max}^2$ | Calculated IC$_{50}$ PD3D Cell Culture |
|---|---|---|
| Cisplatin | 3.62 µM | 5.05 µM |
| Samotolisib | 0.6 µM | 0.87 µM |
| Panobinostat | 0.06 µM | 0.11 µM |
| Niclosamide | 0.31 µM | 0.6 µM |
| Etoposide | 33.8939875 | 87.30551 |
| Temozolomide | 37.6 µM | 105.7 µM |
| Artesunate | 8.58 µM | 38.4 µM |
| Metformin | 10.84 µM | Not Reached |
| Colchicine | 0.006 µM | Not Reached |
| Glutathione | 150 µM | Not Reached |
| Ascorbic Acid | 436.2 µM | Not Reached |
| Hydroxychloroquine | 0.12 µM | Not Reached |
| Pomalidomide | 0.27 µM | Not Reached |
| Sunitnib | 0.09 µM | Not Reached |
| Dichloracetate | 330 µM | Not Reached |

TABLE 5-continued

EFFECTS OF VARIOUS AGENTS ON PATIENT DERIVED ORGANOIDS

| Drug | $C_{max}^2$ | Calculated IC$_{50}$ PD3D Cell Culture |
|---|---|---|
| Bevacizumab | 0.92 µM | Not Reached |
| Kadcyla | 0.53 µM | Not Reached |
| Cetuximab | 1.4 µM | Not Reached |
| Crizotinib | 0.23 µM | Not Reached |
| Propranolol | 0.102 | Not Reached |
| Ruxolitinib | 0.587 | Not Reached |
| Capecitabine (5-FU) | 2.22174388 | Not Reached |
| Cobimetinib | 0.51383399 | Not Reached |
| Ponatinib | 0.13707376 | Not Reached |
| Pemetrexed | 290.623674 | Not Reached |
| Lenvatinib | 0.99987584 | Not Reached |
| Olaparib | 17.4680519 | Not Reached |

A few of the tested agents were slightly effective on organoid samples, but the IC50 number remained below the Cmax, identifying them as poor choices for therapeutic use. Notably, none of the agents listed in Table 5 were as effective as the *cannabis* extract used to treat the patient.

In addition to the agents listed above, several other drugs were tested to see if they influenced organoid growth. The results of which are shown in Table 6. In this case, results are shown as the % of cells that died compared to control. Notably, paclitaxel was shown to be wholly ineffective, and thus the 39% cell death is indicative of the need to greatly increase the dosage for successful treatment. This is consistent with the patient's actual lack of response to treatment with paclitaxel.

TABLE 6

EFFECTS OF VARIOUS AGENTS ON THE DEATH OF PATIENT DERIVED ORGANOIDS

| Drug Name | % Cell Death |
|---|---|
| 5-Fluorouaracil/Capecitabine | 61 |
| Gemcitabine | 56 |
| Bleomycin | 53 |
| Irinotecan | 51 |
| Mitoxantrone | 50 |
| Vinorelbine | 45 |
| Melphalan | 40 |
| Temozolomide | 40 |
| Doxorubicin | 39 |
| Paclitaxel | 39 |
| Vinblastine | 38 |
| Cabazitaxel | 37 |
| Cisplatin | 36 |
| Etoposide | 33 |

TABLE 6-continued

EFFECTS OF VARIOUS AGENTS ON THE DEATH OF PATIENT DERIVED ORGANOIDS

| Drug Name | % Cell Death |
| --- | --- |
| Trabectedine | 32 |
| Dacarbazine | 32 |
| Cyclophosphamide | 32 |
| Carboplatin | 30 |
| Docetaxel, epirubicin, eribulin, ifosfamide, methotrexate, mitomycin, oxaliplatin, pemetrexed, vincristine | No Response |

Although the patient achieved remission after being treated with the combination of GemCap and BSHE at 130 mg/day, she had extensive organ damage due to the numerous rounds of chemotherapy. She eventually died from complications due to organ damage, but it is estimated that her life was extended by about 1 year. At her death, she was free of cancerous growths. Accordingly, even though the combined therapy of chemotherapy and *cannabis* extract comprising CBD proved to be highly effective in reducing tumor growth, the pre-existing damage from chemotherapy proved to be fatal. There is no telling whether she could have achieved earlier remission had she been treated with the *cannabis* extract with CBD during earlier rounds of chemotherapy. If it were so, she would not have been subjected to the several rounds of unsuccessful chemotherapy. We can, however, confirm that her last treatment proved to be effective with a combined therapy of chemotherapy and *cannabis* extract having CBD.

Due to the success of our initial experiments and the results achieved when the live patient was treated with a *cannabis* extract with CBD, we pursued additional research with great vigor. Since our initial experiments showed a complete drop off of organoid numbers at a BSHE dosage of about 10 µg/mL, we were interested to see how organoids responded to concentrations of the BSHE at doses between 1 µg/mL where we saw little, if any response, and 10 µg/mL, where we saw 100% response.

We were able to obtain tissue samples from numerous patients having different grades of endometrial cancer. Grade 1 tumors were described as having less than 5% solid non-glandular, non-squamous growth. In other words, most of the grade 1 tumors presented as having glandular and/or squamous cell likeness. In contrast, grade 2 tumors showed between 6% and 50% of solid, non-glandular, non-squamous growth, while grade 3 tumors exhibit greater than 50% of solid, non-glandular, non-squamous growth. With the number of participants and different grades of tumors, we were able to test the growth of numerous organoids at various doses of BSHE. The methods for creating organoids and experimental protocols are described below in the methods section.

Figure 4A:
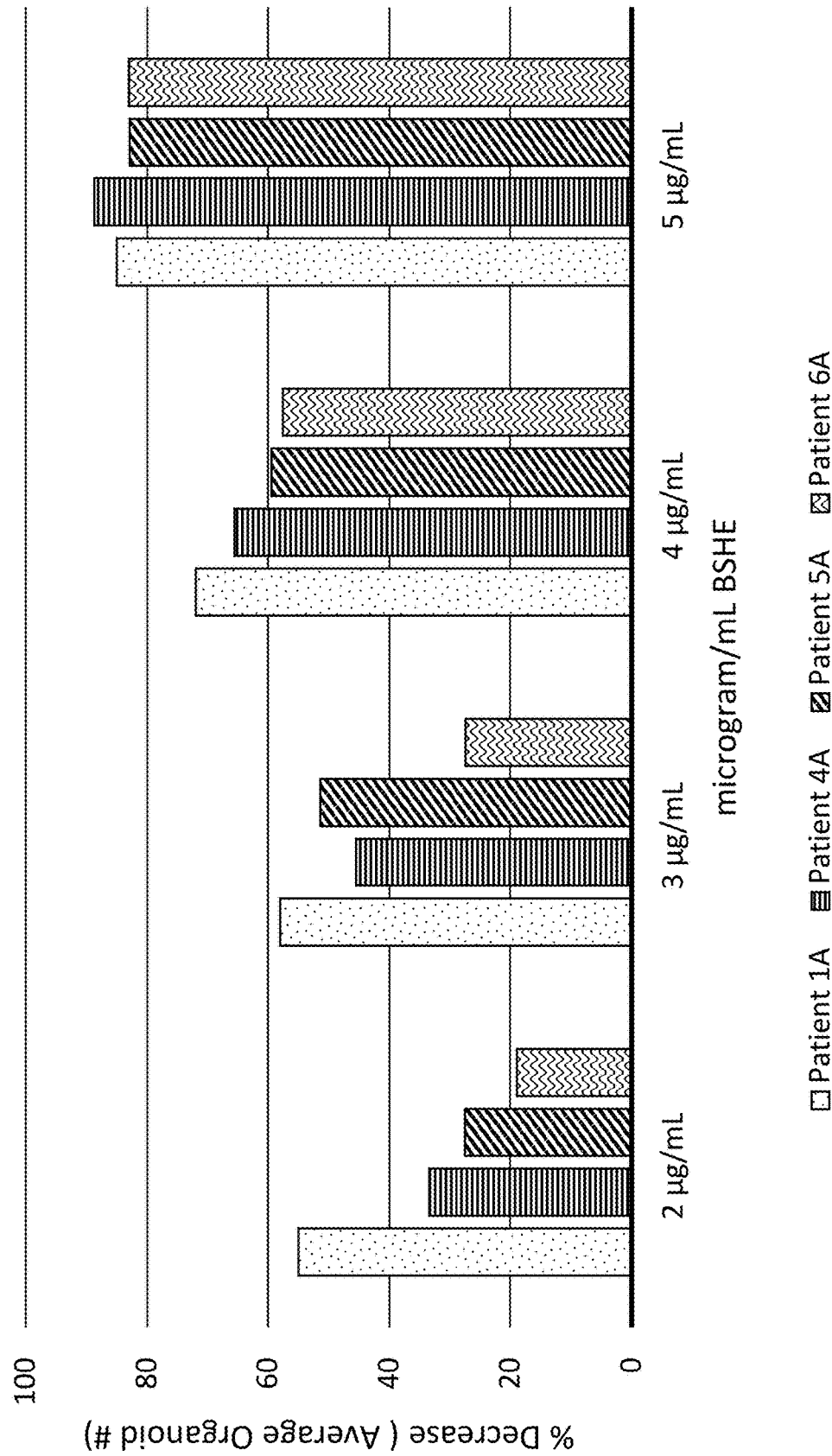
FIGS. 4A and 4B depict the decrease in in organoid number compared to the vehicle for endometrial cancer organoids treated with different concentrations of *cannabis* extract delivered as BSHE including 2, 3, 4, and 5 µg/mL.
Figure 4B:
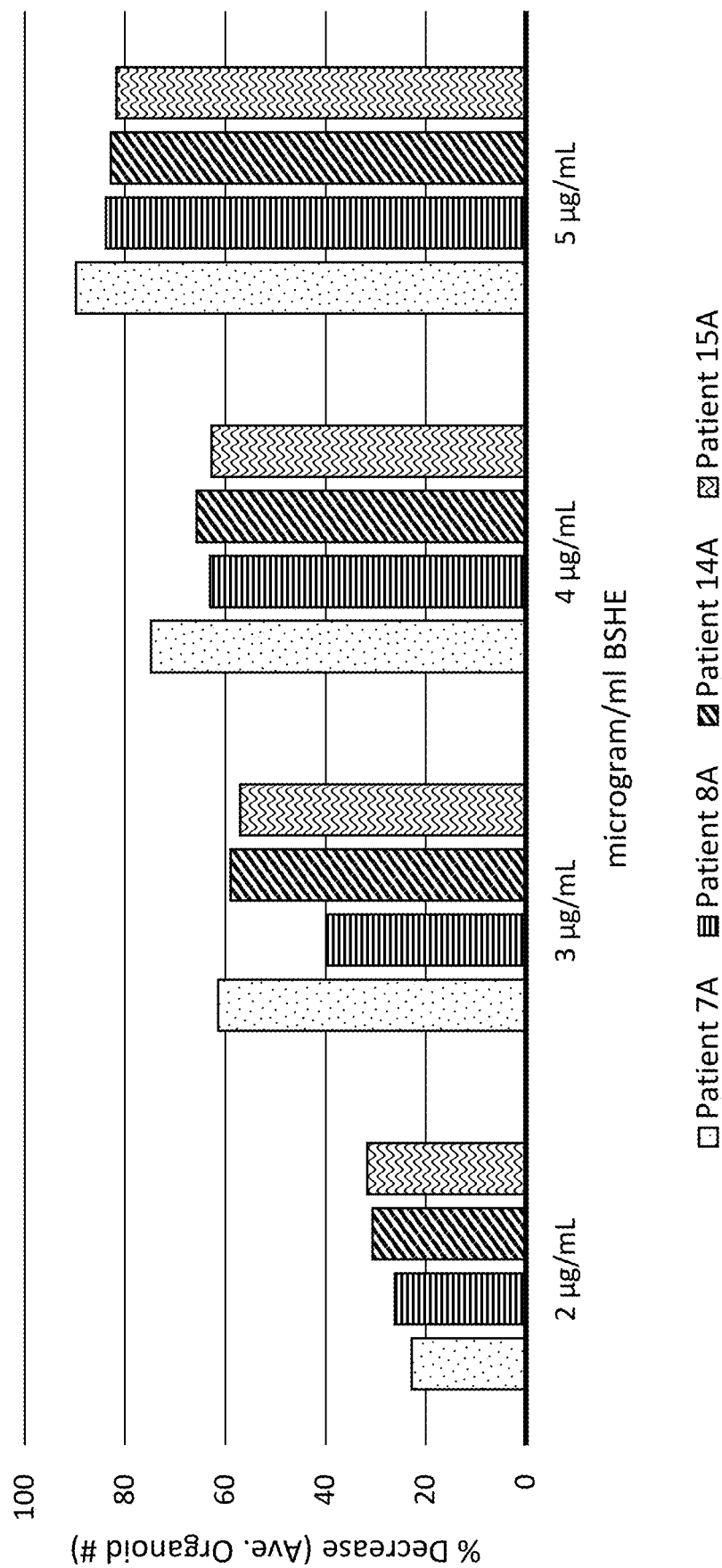
Figure 6A:
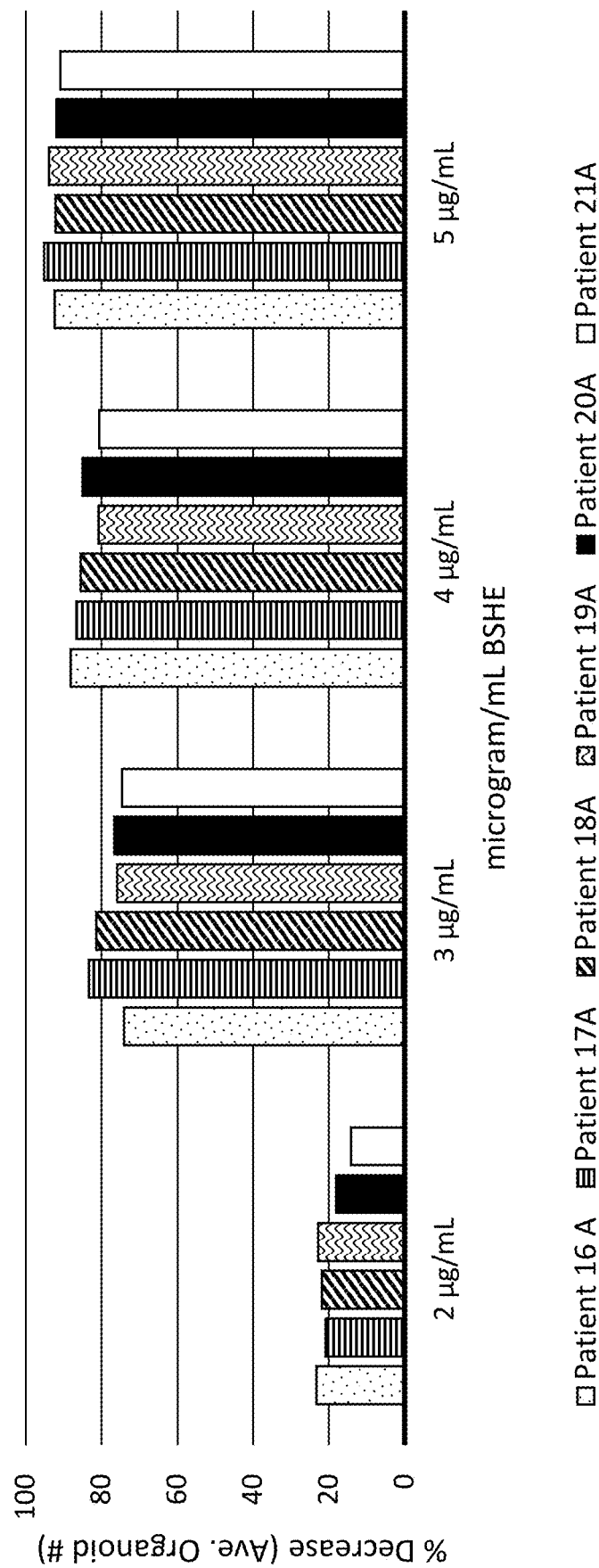
FIGS. 6A and 6B depict the results of grade 3 endometrial cancer organoids treated with BSHE in two trials with concentrations ranging between 2 µg/mL and 10 µg/mL.

For this set of experiments there were 6 different sets of each of grade 1 and grade 3 patient-derived samples, at least 9 different sets of grade 2 patient-derived samples prepared for testing BSHE at 2, 3, 4, and 5 µg/mL. Representative results were selected for graphing in FIGS. 4A, 4B, and 6A. Referring to FIG. 4A, results for experiments with grade 1 endometrial cancer samples are shown as a percent decrease in average organoid number as compared to the average organoid number observed in the vehicle. Data for patient 1A, 4A, 5A, and 6A are shown. In each case, organoid growth was inhibited at doses as low as 2 µg/mL, with cells from patient 1 being the most sensitive at this low dose such that there was a greater than 50% decrease in organoid number. For the remaining patients, a 50% decrease occurred at about 3 µg/mL to about 4 µg/mL. At 5 µg/mL, organoid formation was inhibited at least about 80%. Referring to FIG. 4B, grade 2 organoid numbers followed a similar pattern except that most grade 2 tissues showed a 50% decrease in average organoid number at about 3 µg/mL to 4 µg/mL. All samples showed about an 80% decrease in average organoid number at 5 µg/mL. Turning to FIG. 6A, surprisingly all 6 sets of samples derived from grade 3 endometrial cancer tumors showed a greater than 50% decrease in average organoid number at as low as 3 µg/mL and approached 100% decreases at 5 µg/mL. Within each grade of tumor samples individual responses to treatment with BSHE varied. Nevertheless, they all responded at the lower end of the dosing spectrum, and in most cases quite well.

Figure 5A:
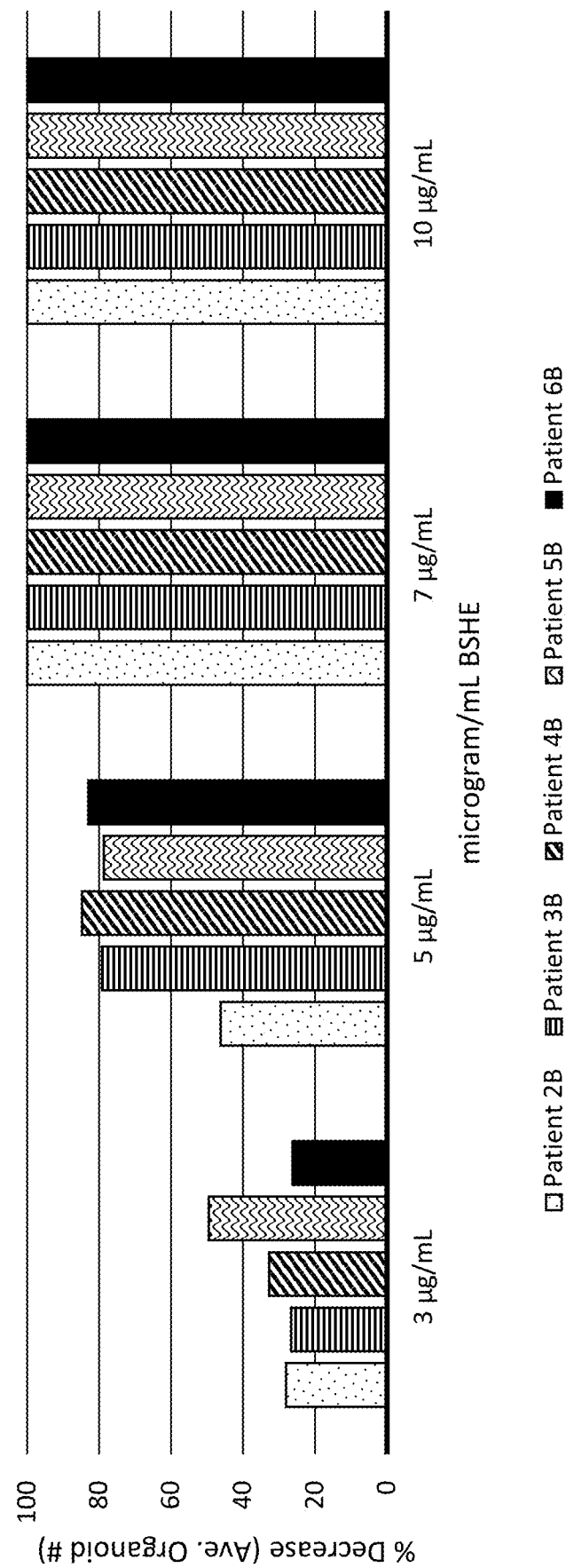
FIGS. 5A and 5B depict the decrease in in organoid number compared to the vehicle for endometrial cancer organoids treated with different concentrations of *cannabis* extract delivered as BSHE including 3, 5, 7, and 10 µg/mL with FIG. 5A depicting results for grade 1 and FIG. 5B depicting results for grade 2 endometrial cancer-based organoids.
Figure 5B:
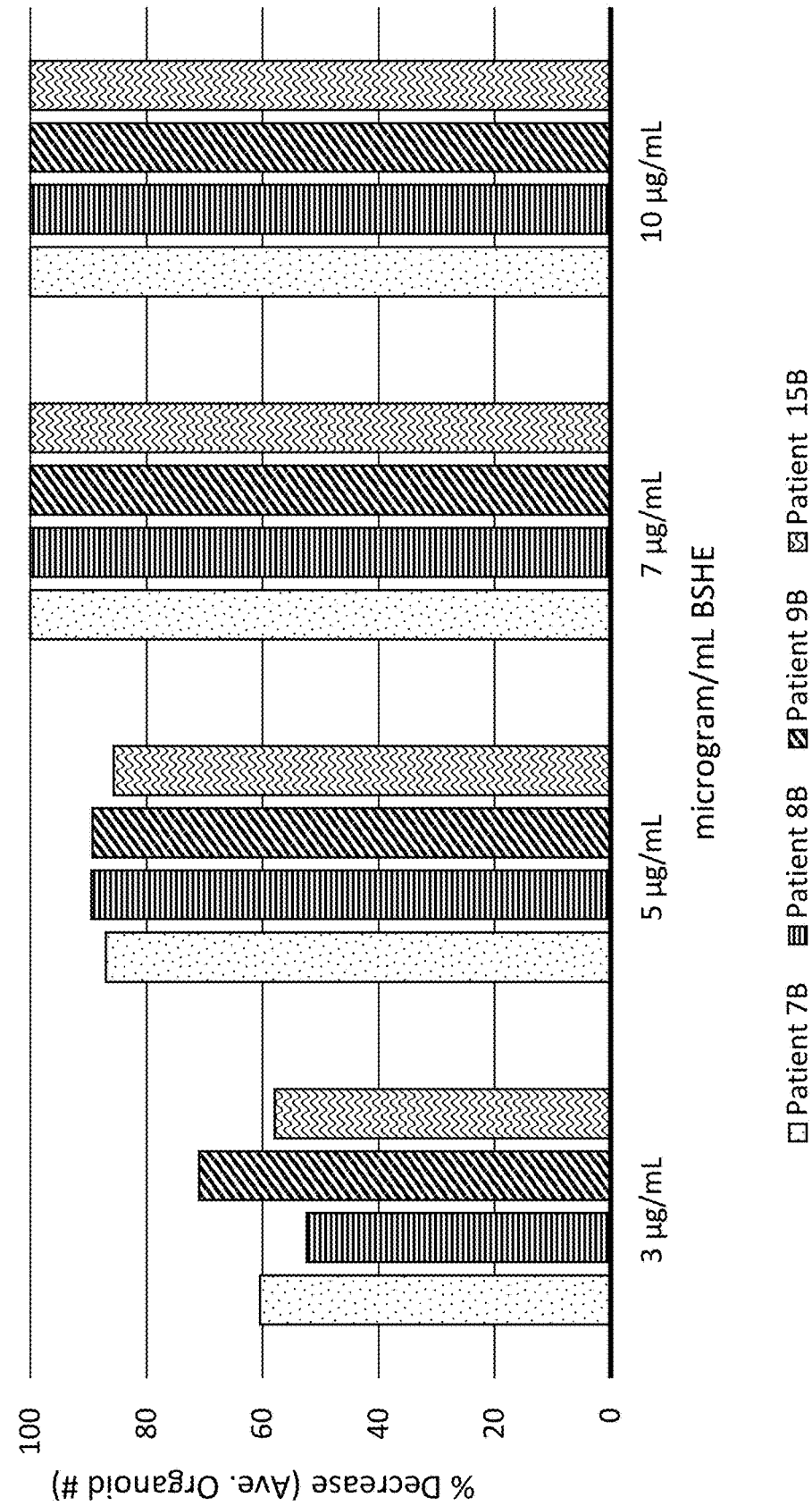
Figure 6B:
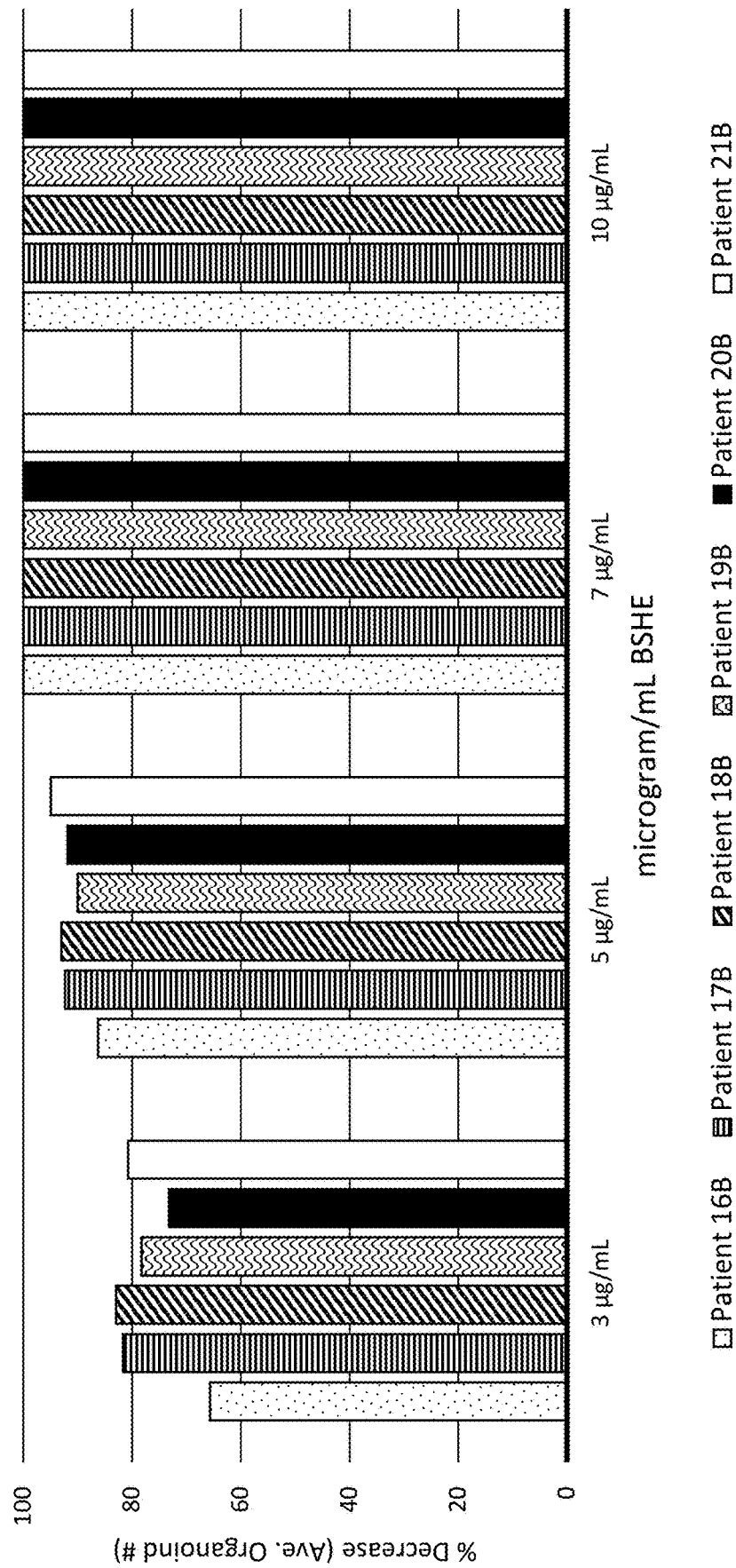

At the same time, patient-derived samples were also tested for response to 3, 5, 7, and 10 µg/mL of BSHE. Referring to FIG. 5A, representative samples of grade 1 tissues again mostly showed about a 50% decrease to the average number of organoids between 3 µg/mL and 5 µg/mL, except for cells from patient 2B. By 7 µg/mL of BSHE, however, all grade 1 patient-derived samples showed complete inhibition of organoid number, even patient 2B. Referring to FIG. 5B, surprisingly, grade 2 samples in this set were affected by 3 µg/mL BSHE such that, of the representative samples shown, all four had about a 50% or greater decrease in average organoid number. Again, at 5 µg/mL the response was a greater than 80% decrease, with 100% inhibition of organoid formation at 7 µg/mL BSHE. Referring to FIG. 6B, the grade 3 patient-derived samples in this set also were surprisingly sensitive to low doses of BSHE with a 50% decrease in average organoid number for all patient samples being less than 3 µg/mL. A 5 µg/mL dosage of BSHE again showed a greater than 80% decrease in the average organoid number and at 7 µg/mL there were no organoids.

Accordingly, based on FIGS. 4A, 4B, 5A, 5B, 6A, and 6B, organoids from grade 1, 2, and 3 EC were able to show a dramatic reduction in the average number of organoids as compared to the vehicle at concentrations as low as 2 µg/mL, and in each case, as low as 7 µg/mL. Therefore, application of *cannabis* extracts comprising CBD at the defined concentrations of CBD are effective decreasing the number of viable patient derived organoids from EC. The data is clear that the given doses of *cannabis* extracts, with a known quantity of CBD are effective in reducing endometrial cancer organoid growth.

After narrowing down the range in which 50% of endometrial cancer organoids were inhibited from forming in the presence of BSHE, we then turned to other *cannabis* extracts comprising CBE to determine their efficacy in inhibiting cancerous organoid formation. Thus, in addition to retesting broad spectrum hemp extract (BSHE), which was the basis for all prior studies, we also tested a full spectrum hemp extract (FSHE), which typically contains less than 0.3% of $\Delta^9$-THC, an isolated CBD, which is a naturally derived and isolated CBD, and finally an isolated CBDA, which is a precursor to CBD.

For this set of experiments, we obtained tissue samples from a new set of 12 patients, each having grade 1, grade 2, or grade 3 endometrial cancer. Cells from these patients were prepared as described in the Methods section below. Generally, cells were prepared from each patient to test the efficacy of BSHE (FIG. 7A), FSHE (FIG. 7B), CBD isolate (FIG. 7C), at 1, 2, 3, 4, 5, 7, and 10 µg/mL and CBDA (FIG.

7D) at 1, 5, 10, 15, 20, 25, 35, and 50 µg/mL. CBDA was tested at higher concentrations due to a general lack of sensitivity at lower doses.

Referring to FIG. 7A, representative samples from grade1, grade 2, and grade 3 endometrial cancer organoids are shown. In these graphs, dosages are plotted against the % of viable organoids as compared to the respective vehicle, which is set at 100% for each set of patient-derived samples. Interestingly, the organoids from the grade 2 tissues were the most sensitive to the BSHE and the organoids from the grade 1 tissues were the least sensitive to BSHE with a percent viability of 50% obtained roughly at 1 µg/mL and 4 µg/mL BSHE, respectively. The grade 3 EC were at 50% viability at roughly 3 µg/mL. Thus, even though there was variation in responses observed in these samples, the dosages at which a 50% response was observed was still in line with what was previously observed. Furthermore, there was virtually no growth at 10 µg/mL for each of the representative samples. That is, although there was a minimal amount of growth at 10 µg/mL for the grade 1 samples, it was only about 4%, which is negligible due to background noise. Less than 10% viability is considered 95-100% cell death in these experiments due to residual signaling from dead cells and Matrigel.

Figure 7B:
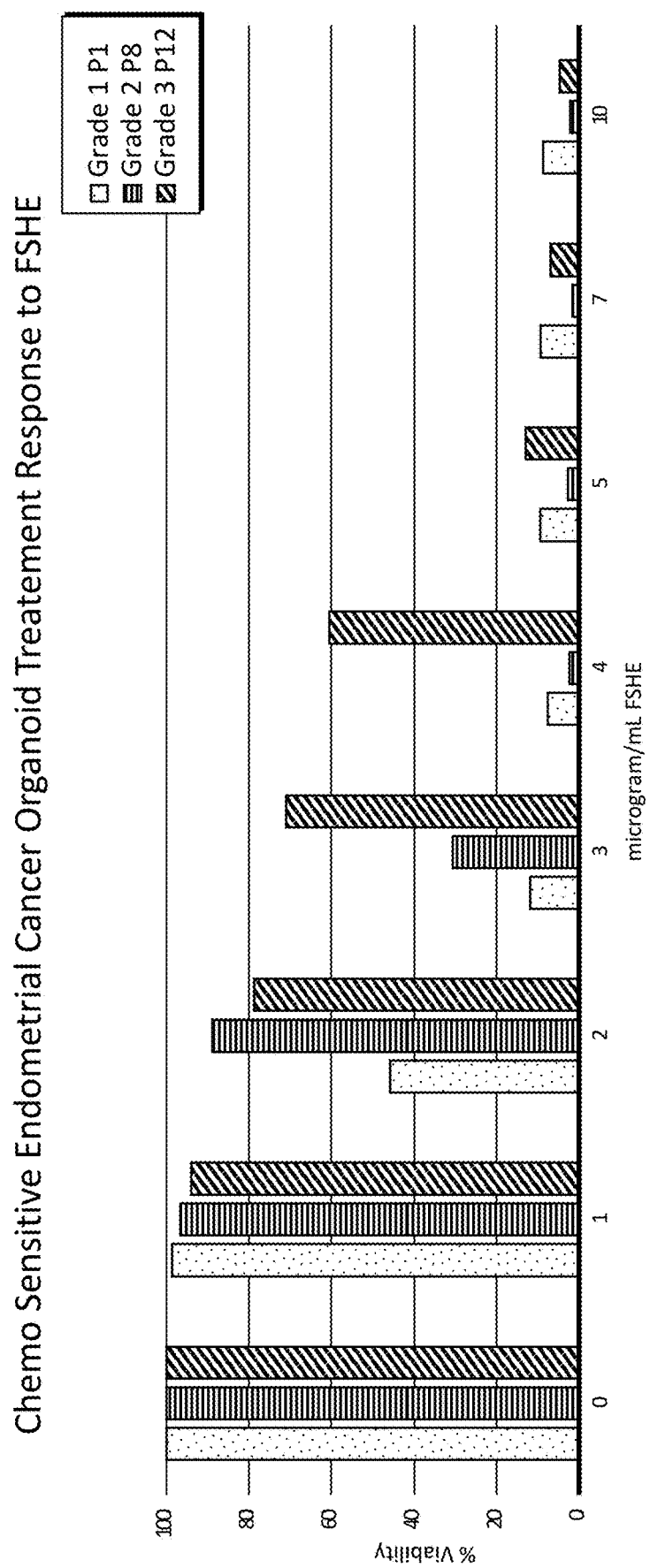

Turning to FIG. 7B, the response to organoid viability to dosages of FSHE are shown for representative samples of grade 1, grade 2, and grade 3 endometrial cancer. Interestingly, the grade 1 cells, coming from the same patient shown in FIG. 7A, were more sensitive to FSHE than the BSHE having a 50% viability at roughly 2 µg/mL FSHE as compared to the 4 µg/mL. BSHE. Nonetheless, a small percentage of organoids were still viable at 10 µg/mL FSHE. The data shown for the grade 2 EC cells showed a 50% decrease at between 2 and 3 µg/mL of FSHE, with nearly zero viable organoids observed at both 7 and 10 µg/mL FSHE. The grade 3 samples showed 50% viable organoids at a dosage between 4 and 5 µg/mL FSHE, and again a negligible % of viable organoids at both 7 and 10 µg/mL FSHE. Thus, for all three grades of endometrial cancers 50% organoid viability was observed at low doses of FSHE.

Figure 7C:
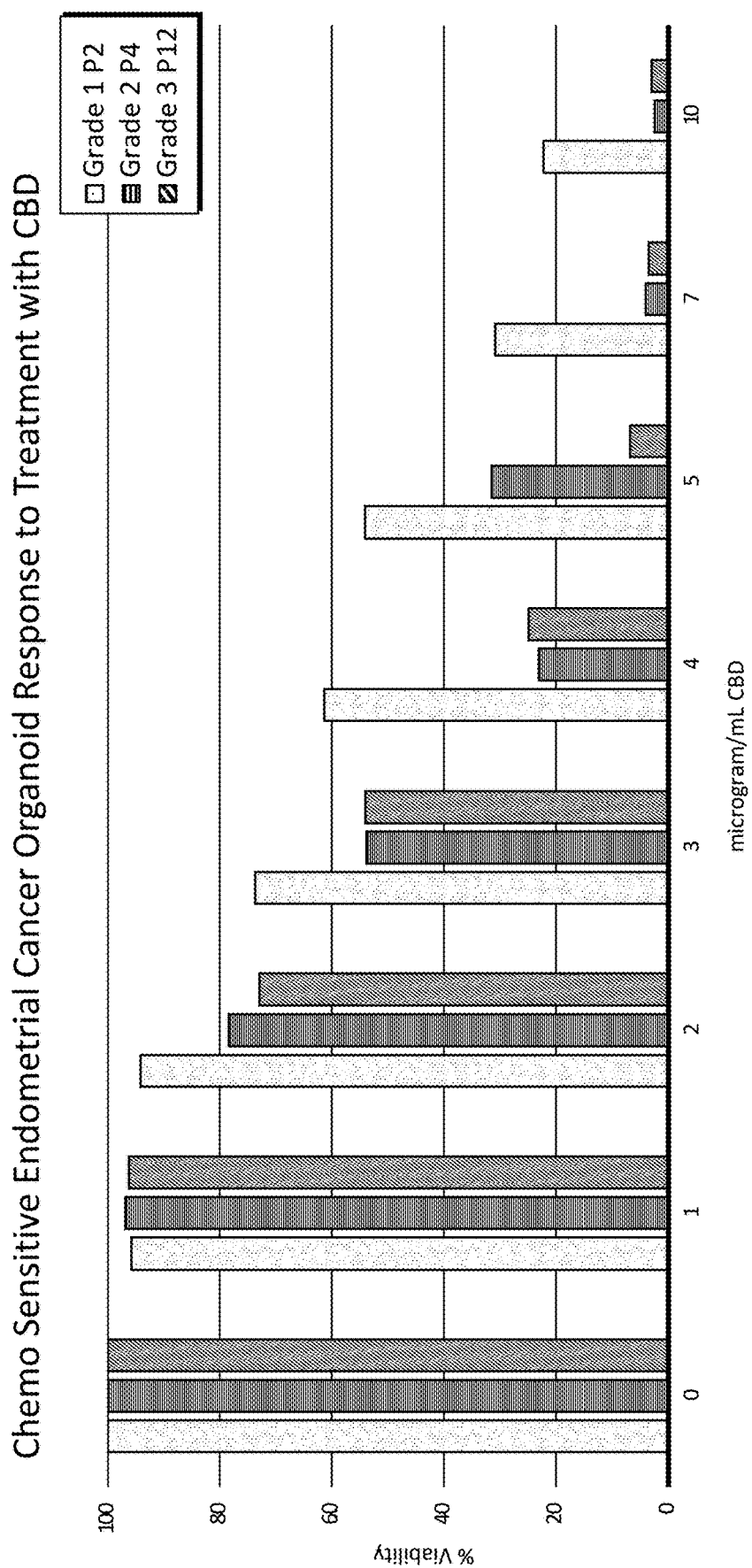

FIG. 7C shows the % viability of organoids from grade 1, grade 2, and grade 3 endometrial cancer in response to treatment with CBD isolate. Interestingly, the grade 2 and grade 3 representative samples seem to be somewhat more sensitive to CBD isolate as the 50% viability for cells from the same grade 2 patient was observed at about 3 µg/mL CBD isolate compared to about 4 µg/mL for FSHE and from the same grade 3 patient was about 3 µg/mL for CBD and between 4 and 5 µg/mL for FSHE. Nonetheless, organoids from both grade 2 and 3 EC tumors were virtually zero at both 7 and 10 µg/mL of CBD isolate. Interestingly, tissues from the grade 1 patient, who is later identified as a lower responder, does not show complete response even at 10 µg/mL. However, tissues for this patient were then exposed to 15 and 20 µg/mL CBD isolate, which showed a complete response, consistent with the other trials.

Figure 7D:
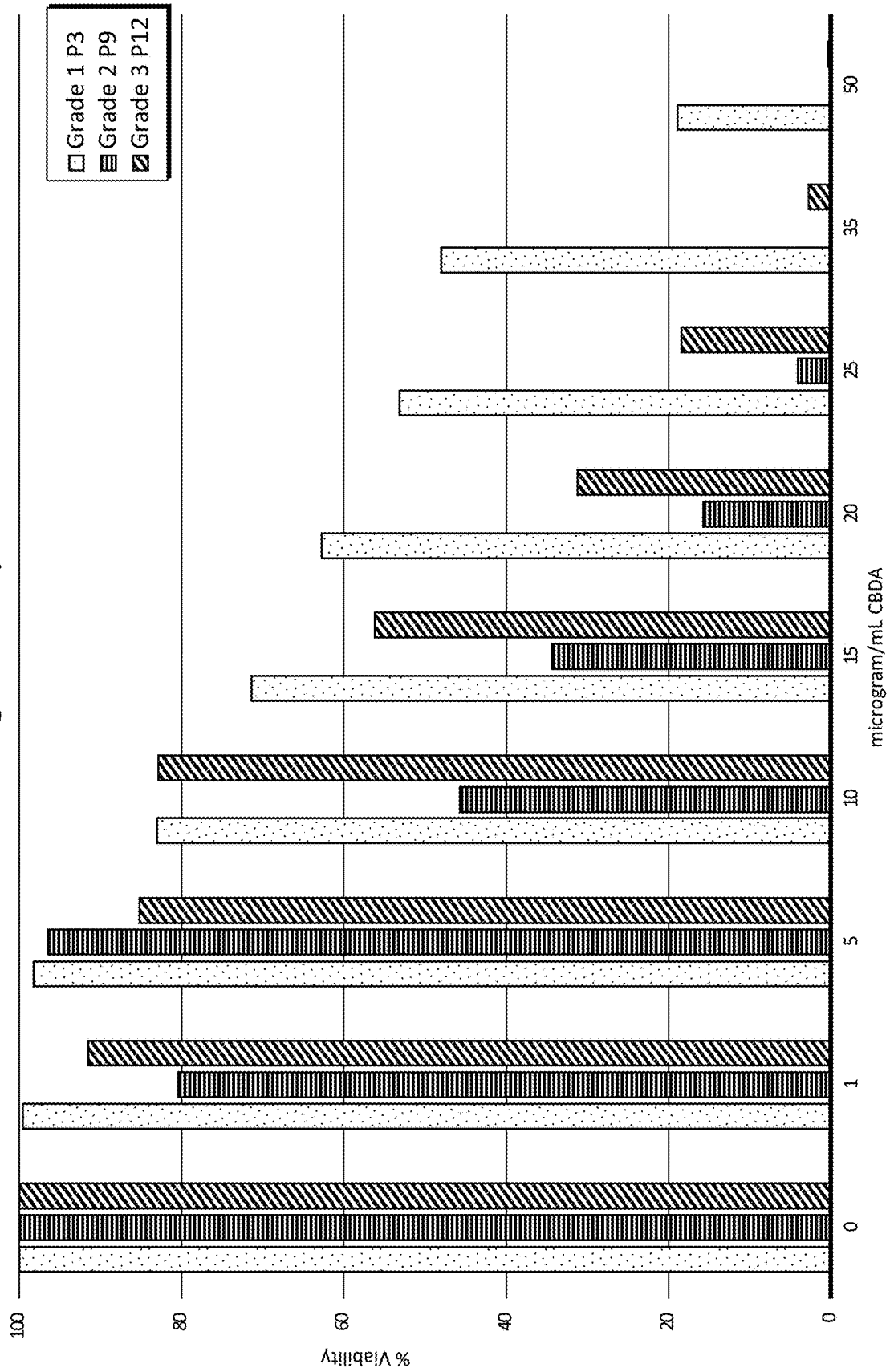

FIG. 7D uses CBDA as the treatment drug. As lower doses of CBDA did not affect organoid viability across the board, higher doses of CBDA were used showing an even stronger patient differentiation—even at doses of 10 and 15 µg/mL, a strong response was not seen in all patient derived organoids. Accordingly, additional dosing up to 50 µg/mL was completed before all patients showed nearly 0% formation of viable organoids. CBDA is the raw form of CBD, abundant in the plant itself but rarely consumed. CBDA is readily converted to CBD via exposure to heat causing decarboxylation. Even sunlight can provide sufficient heat to instigate CBDA decarboxylation to CBD. Nevertheless, CBDA remains of pique scientific interest due to its potent therapeutic effects and benign nature as a non-intoxicant with little to zero known side effects. Moreover, recent pharmacokinetic trials have demonstrated that the serum bioavailability of orally delivered CBD and other cannabinoids increase substantially when the compounds are consumed with CBDA. Additionally, CBDA demonstrated increased bioavailability when consumed along with other cannabinoids in FSHE as compared to administering an equivalent dose of isolated CBDA. These data support the "entourage effect" and suggest that CBDA plays a primary role in optimizing otherwise poor bioavailability of orally ingested cannabinoids.

To further out studies on the effects of *cannabis* extracts comprising CBD, we looked at endometrial cancer tumor volume in mice. Generally, EC stem cells from the same patients that participated in the organoid studies of FIG. 7, were injected into the mice, and allowed to grow. After tumors reached a certain size, the mice were either injected (3 times/week) with the extract-delivery vehicle or with the particular *cannabis* extract. After a certain amount of time elapsed, tumor size was measured. The details regarding patient-derived xenograft methodology and experimental protocol are provided in the Methods section.

Referring to FIG. 8, the number of days of treatment is plotted against an % change in tumor volume for each of the vehicle, BSHE, FSHE, CBD isolate, and CBDA. The % change is an average number taken from tumor volumes of three mice compared to the starting average tumor volume on day 0 of treatment. Change can either be positive (tumor increases in size) or negative (tumor decreases in size). As expected, the vehicle (no treatment control) continuously increased in size over 21 days with almost a 150% increase from the day treatment started. In contrast, tumors in mice treated with a *cannabis* extract comprising CBD decreased in size. Thus, at the very least we have shown that systemic delivery of *cannabis* extracts comprising CBD is can be used to treat endometrial cancer. This is an important verification as it confirms bioavailability of the various *cannabis* extracts comprising CBD.

Successful delivery of the various *cannabis* extracts comprising CBD, however, is validated by the observed changes in tumor volume. For example, after one week of treatment (i.e., 3 doses of about 30 mg/kg extract) all tumor averages indicate an initial increase in size. By day 10, however, most average tumor volumes began to decrease with the tumors in mice treated with CBDA showing the greatest decrease over the three days of from a little over a 30% increase to a greater than 30% decrease; an overall decrease that is greater than 60% in just three days. Mice treated with BSHE and FSHE showed a similar switch from an increase in average tumor volume to a decrease average tumor volume, but not as dramatic as that observed with CBDA. Interestingly, the tumors in mice treated with CBD isolate were not as responsive as the tumors in mice treated with the other *cannabis* extracts, which is especially surprising as CBDA is a precursor to CBD. Within 2 weeks (14 days-6 doses total), most tumors were at least 50% decreased in volume compared to their starting size, except for those in the mice treated with CBD, which was less than 50%, but still a decrease in average tumor volumes. In contrast, mice treated with CBDA showed an average decrease in tumor volume of 70% compared to starting tumor volume averages. By day 21, only three weeks of treatment, 9 doses total, average tumor volume in each of the treatment groups were decreased by at least 50%, with those treated with CBDA approaching 100% resolution. What is even more amazing is that when left untreated, the average tumor volume was slightly less than a 150% increase. Thus, the *cannabis* extracts comprising CBD not only prevented endometrial tumor volume from increasing, but they also reversed tumor volume, in some cases almost completely. These results confirm what was observed in the organoid experiments and what was observed in the human patient that was treated with BSHE.

Notably, the concentrations of *cannabis* extracts comprising CBD used in the mouse model experiments is on the low end of what would be considered a therapeutic dose for administering to a human patient or a mouse. For example, the 30 mg/kg given to the mice translates to about 170 mg for a human of average size. Recall that a CBD isolate is currently prescribed in the US at a concentration of 5-50 mg/kg daily. We intentionally used low doses to treat mice to show the impact of various *cannabis* extracts comprising CBD at these low doses on tumor volume over time rather than forcing the data to zero, by using double, triple, or higher of the dose as administered to the mice, each of which would be appropriate human equivalent doses. Furthermore, even with the lower dosing, within 3 weeks of treatment, virtually all of the samples had tumor volumes progressing toward zero, especially those treated with CBDA. Therefore, when comparing dosages used in the mice to those applied to the organoids, we saw that each sample in the mice retained the efficacy from the organoid data. In other words, endometrial cancer cells obtained from the same patient were responsive to *cannabis* extracts comprising CBD in both an organoid form and patient-derived xenograft form. As such, administering higher doses of *cannabis* extracts comprising CBD, will yield a greater reduction in tumor volume in the mouse model. From all of these experiments taken in total, it is quite clear that, administering *cannabis* extracts comprising CBD is effective in greatly decreasing the volume of endometrial cancer tumors, which not only slows the growth of endometrial cancer tumors, but may eradication of tumor cells together, as is demonstrated in our mouse models.

Figure 1F:

Moreover, we have shown that gynecological tissues can be targeted by certain applications of *cannabis* extract comprising CBD, whether through oral, oral mucosal, vaginal mucosal, or other administration to treat EC and reduce tumor size. Because of the targeted approach toward gynecological tissues, those of ordinary skill in the art will recognize that certain therapeutics are able to pass through the vaginal mucosa and contact tissues both on the vaginal wall, but also tissues adjacent to the vaginal wall, including the entirety of the gynecological tract, including the uterus, cervix, ovaries, etc., as non-limiting tissues. Indeed, while these tissues are generally connected, application into the vagina does not always ensure that a therapeutic will also travel to and impact the uterus or ovaries. However, there is an abundance of endocannabinoid receptors in the female reproductive tract to allow for possible therapeutic impact of administered cannabinoids to such tissues, as is depicted in FIGS. 1E and 1F. Furthermore, intervaginal delivery of cannabinoids may result in uptake via the inguinal lymph nodes, leading to addition systemic uptake from the reproductive tract.

Encouraged by the results obtained with *cannabis* extracts comprising CBD alone, we were thoroughly encouraged to see how a combined therapy with *cannabis* extracts comprising CBD and chemotherapeutic agents would work. Chemotherapy can be exceedingly harmful to healthy tissues as well as cancerous ones. High doses of chemotherapy, prolonged treatment with chemotherapy, or both can lead to high morbidity among those treated. The side effects of chemotherapy are often chronic and include damage to major organs/organ systems (e.g., nervous system, circulatory system, digestive system, reproductive tract, etc.). Chemotherapies can also result in secondary cancers over time, and in the worst cases lead to premature death, especially when chemotherapy is given at high doses. Being able to reduce the duration and/or strength of chemotherapy may significantly improve both short term and long term adverse effects of such treatment with a goal of improving both the quality and duration of a patient's life.

Again, we returned to our organoid experiments to test our belief that a patient would benefit from taking a chemotherapeutic agent in combination with *cannabis* extract comprising CBD therapy. To perform these experiments, we used cells from patient 4 (see, e.g., FIGS. 7A and 7C) to test grade 2 endometrial cancer and cells from patient 12 (see, e.g., FIGS. 7B-7D) to test grade 3 endometrial cancer. We calculated the IC50 doses for both patients for each *cannabis* extract comprising CBD using the data from our prior organoid studies. The results of which are shown below in Table 7. The organoids were treated with either the chemotherapeutic agent alone or the chemotherapeutic agent together with the IC50 concentration of the particular *cannabis* extract comprising CBD. Methods concerning producing organoids from human tissue samples are provided in the Methods section at the end of this document.

TABLE 7

CALCULATED IC50 DOSES OF CANNABIS EXTRACTS COMPRISING CBD FOR PATIENTS 4 AND 12

|  | IC50s for Patient 4 Organoids (Grade 2 Endometrial Cancer) | IC50s for Patient 12 Organoids (Grade 3 Endometrial Cancer) |
| --- | --- | --- |
| Broad Spectrum Hemp Extract | 1.004 µg/mL | 2.458 µg/mL |
| Full Spectrum Hemp Extract | 4.634 µg/mL | 3.791 µg/mL |
| CBD Isolate | 3.090 µg/mL | 2.92 µg/mL |
| CBDA | 12.05 µg/mL | 15.82 µg/mL |

Figure 9A:
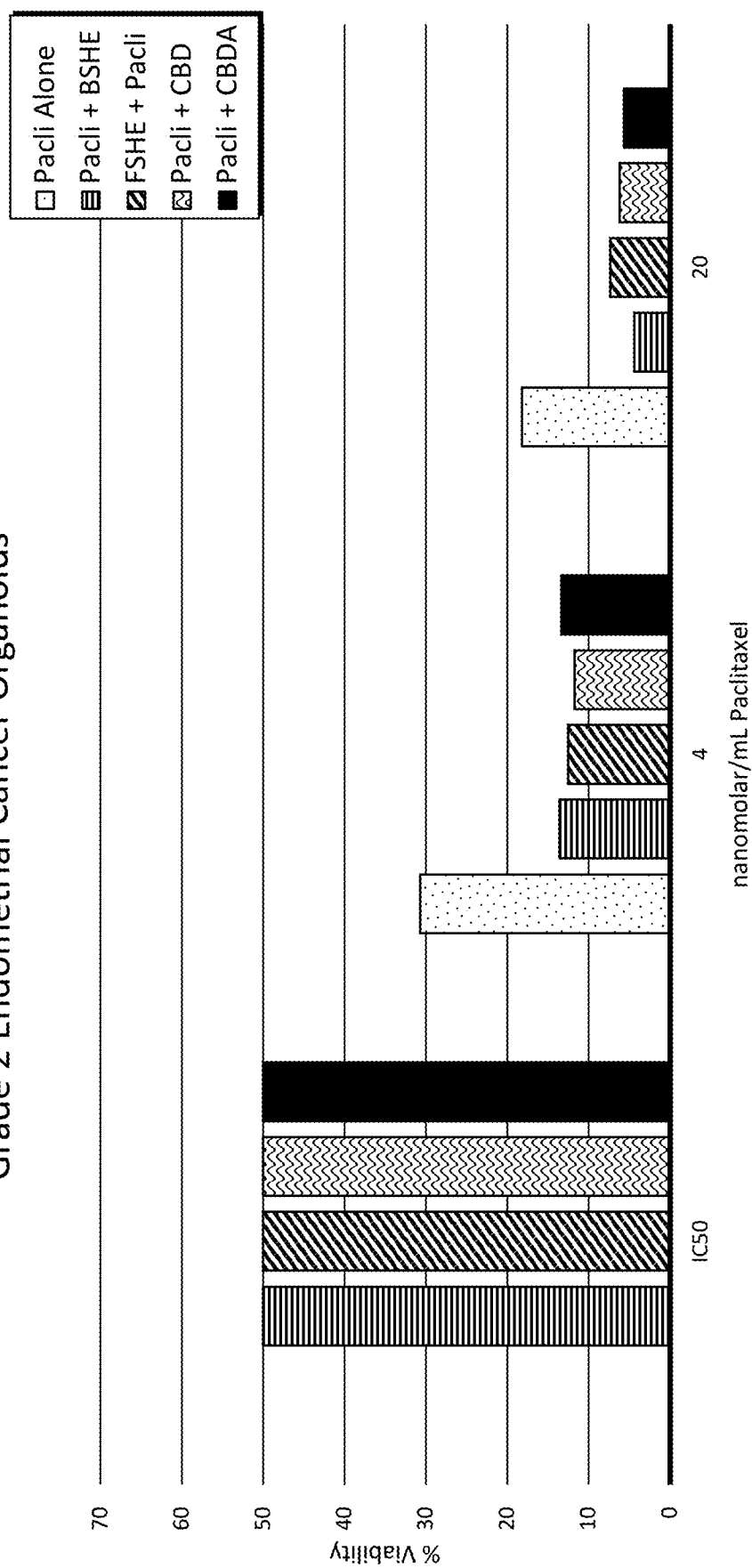
FIGS. 9A and 9B depict a combined therapy treatment tested on patient derived endometrial cancer organoids, wherein the chemotherapy agent is paclitaxel and is administered with a *cannabis* extract.

Referring to FIG. 9A, responses to organoid viability in the presence of paclitaxel or paclitaxel with the indicated *cannabis* extracts are shown. The columns to the far left of the graph indicate the theoretical 50% reduction in organoid viability that is expected from providing the IC50 dosage of the particular *cannabis* extract. The columns in the middle of the graph indicate the percentage of viable organoids as compared to a control when treated with the IC50 dose of a given *cannabis* extract together with 4 nM/mL paclitaxel or 4 nM/mL paclitaxel alone and the columns to the far right of the graph are the same as the center columns except the dosage of paclitaxel is 20 nM/mL. Paclitaxel was also tested at 8, 12, and 16 nM/mL, with only moderate changes in a linear fashion, and are thus not depicted in the drawing. In other words, we chose to highlight the profound effect the tested *cannabis* extracts had on organoid viability.

Four nanomolar paclitaxel alone decreases organoid viability to about 30% (as compared to 100%), which on its own seems fairly substantial. In combination with the given *cannabis* extracts, however, the percentage of organoid viability was reduced to between about 12 and 14%. That is, each *cannabis* extract at an IC50 dosage in combination with 4 nM/mL paclitaxel was able to prevent roughly 90% of endometrial cancer organoids from forming as compared to the control, and between about 17% and 19% more than paclitaxel alone at the same concentration. Thus, in combination with the 4 nM/mL paclitaxel the IC50 concentration of each tested *cannabis* extract was able to achieve a greater than 50% inhibitory effect. Furthermore, the higher dosage of paclitaxel (20 nM/mL) showed only about a 12% improvement over the lower dose of paclitaxel even though the amount given is five times greater. And comparing the result of 20 nM/mL paclitaxel alone to that of paclitaxel at 4 nM/mL plus any of the tested *cannabis* extracts, the combined inhibitory effect is between 4% and 6% better than the higher dose of paclitaxel alone. Stated another way, administering 5 times more paclitaxel only improved the inhibitory response by 12% whereas administering 4 nM/mL paclitaxel in combination with an IC50 dose of a given *cannabis* extract improved the inhibitory response by between 17% and 19%. Which begs the question, why administer more of a toxic agent, and get a worse result than administering less of the toxic agent in combination with a *cannabis* extract comprising CBD? Not to ignore the results of 20 nM/mL paclitaxel in combination with provided *cannabis* extracts—the results were amazing, showing a percentage of viable organoids of only between about 4% and about 6%, an almost complete inhibition of cancerous organoid production. Consequently, by taking an IC50 dose of any of the *cannabis* extracts and administering it concurrently with the paclitaxel, a surprising synergy was identified, which could dramatically reduce the amount of paclitaxel needed to achieve low to no viability for the endometrial cancer organoids, or to provide greater efficacy, yielding a more effective treatment.

Figure 9B:
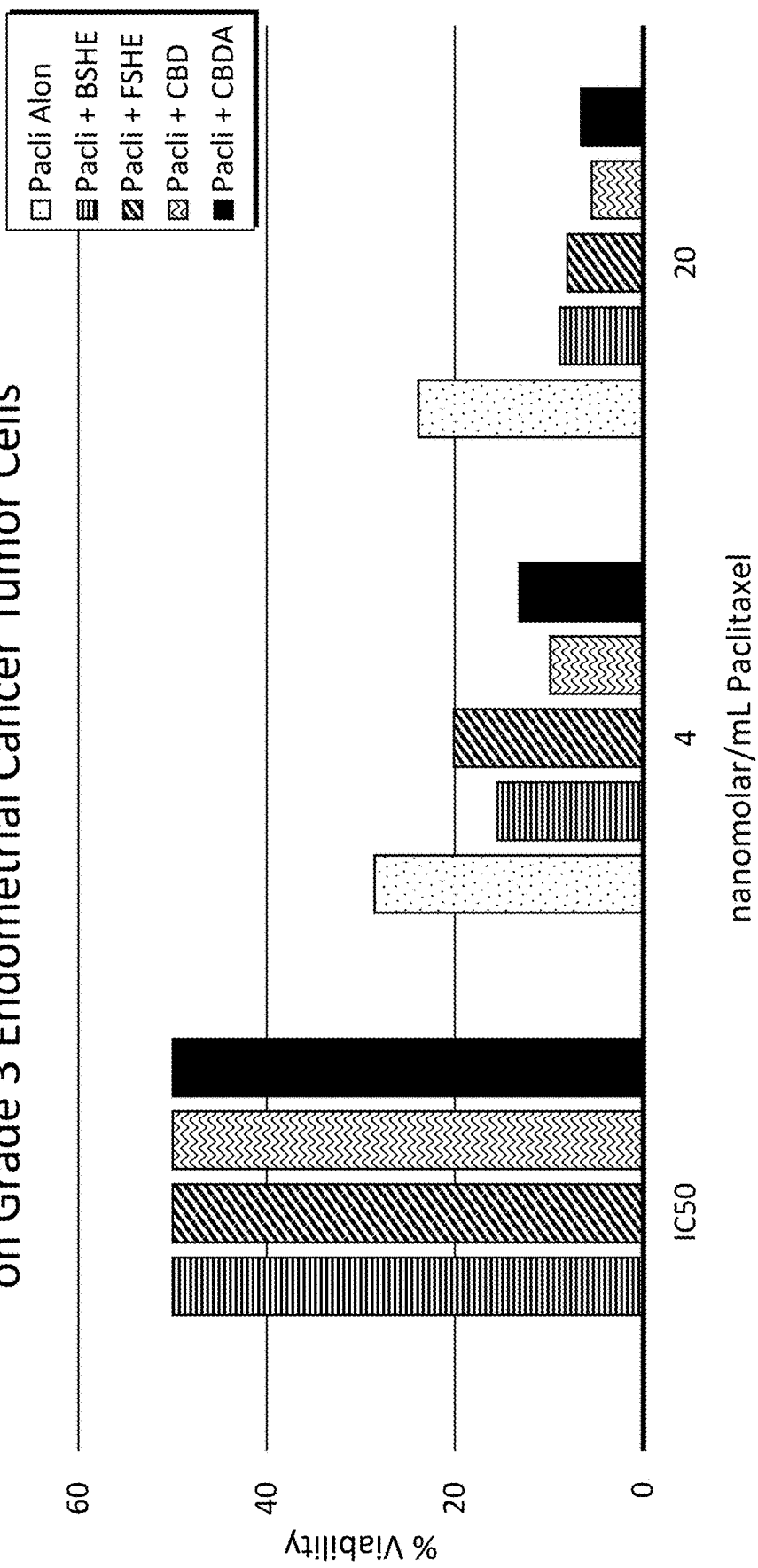

Referring to FIG. 9B, a similar but more dramatic result was observed. In this case, cells were taken from grade 3 endometrial cancer tissue and were subjected to the same treatment as the cells from grade 3 endometrial cancer. Namely, there was only about a 5% improvement in reducing the percentage of viable organoids when administering 4 nM/mL and 20 nM/mL paclitaxel. In contrast, if 4 nM/mL paclitaxel is combined with a *cannabis* extract, there is a decrease in the % of viable organoids of at least 9% with FSHE and up to 19% with CBD isolate. Thus, again a lower dose of paclitaxel in the presence of one of the tested *cannabis* extracts provides a better result than a 5× increase in the dose of paclitaxel. Furthermore, the effect of the tested *cannabis* extracts in the presence of paclitaxel is substantially more than either one alone. That is, the IC50 doses of the tested *cannabis* extracts in the presence of both 4 nM/mL and 20 nM/mL paclitaxel inhibited organoid viability more than 50%. In fact, in the presence of 20 nM/mL paclitaxel, between only about 8% and 5% viable organoids were observed.

Viability of endometrial cancer cells from patient 4 was also tested in the presence of carboplatin alone and in combination with the IC50 of each of BSHE, FSHE, CBD isolate, and CBDA. Referring to FIG. 10, the results are graphically depicted in much the same way as the results with paclitaxel. In this case, however, three doses of carboplatin are shown in the graph: 50, 100, and 250 µM/mL. Looking at the % viability of organoids in the presence of carboplatin alone, at 50 µM/mL there is reduction of viable organoids of about 50% whereas at 100 µM/mL there is a 2% decrease as compared to 50 µM/mL and at 250 µM/mL, 5 times more than 50 µM/mL, organoid viability is at about 32%, only a 17% decrease from that achieved at 50 µM/mL. When 50 µM/mL carboplatin is combined with an IC50 dose of BSHE and FSHE there is a 26% and 36% reduction as compared to 50 µM/mL carboplatin alone. At double the dose of carboplatin, 100 µM/mL, the decrease in the percentage of viable organoids is even more impressive. Namely, in combination with an IC50 dose of BSHE, there was a 26% decrease compared to carboplatin alone and with the IC50 dose of FSHE there was a 40% decrease over carboplatin alone. Furthermore, carboplatin in the presence of the IC50 dose of CBD isolate was also improved, and by about 32%. Thus, at 100 µM/mL of carboplatin in the presence of the IC50 doses of BSHE, FSHE, and CBD isolate, the resultant decrease in the % of viable organoids is more than that achieved by more than double the dose of carboplatin alone. And IC50 doses of either BSHE or FSHE with 50 µM/mL of carboplatin still produced a better result than with 250 µM/mL carboplatin alone. And so the trend continues where a lower dose of a chemotherapeutic agent in the presence of a *cannabis* extract comprising CBD produces a better result than a higher dose of chemotherapeutic agent alone. It should be noted that the best results were obtained with the highest dose of carboplatin in combination with each of BSHE, FSHE and CBD isolate, where the percent of viable cells was as low as 1.3. Clearly the synergistic effect of the *cannabis* extracts comprising CBD and chemotherapeutic agent produces a better result than either agent alone. That is, the combined therapeutic is surprisingly much more effective than either alone.

Thus, when looking at organoid examples, the addition of the *cannabis* extract with a chemotherapy agent provides for a dramatic reduction in the number of organoids when combined with the paclitaxel or the carboplatin. Accordingly, based on this result, a patient could take a greatly reduced amount of either of the chemotherapy drugs, combined with an effective amount of the *cannabis* extract comprising CBD to obtain a similar destruction of EC cells, and even shows a much greater impact and higher rate of kill than taking the chemotherapy agent alone, even at the highest effective doses. Furthermore, by testing the most common chemotherapy drugs utilized for EC, one being a plant-based alkaloid and the other a platinum-based, we know that the results are translatable across different chemotherapeutic agents that function in different ways from one another.

To confirm the efficacy of organoid model, we again turned to patient-derived xenografts in mice, the methods of which are essentially the same as before except in these experiments we also used paclitaxel at 10 mg/kg body weight alone or in combination with *cannabis* extract comprising CBD at 30 mg/kg body weight, which is about 170 mg/day for a human dose. The dosage of paclitaxel given to the mice relates to a clinical dose of only 30 mg/m$^2$, which is dramatically lower than the 175 mg/m$^2$ that is given to human patients to achieve an effective therapeutic treatment.

FIG. 11 details the results of mice tumor volume comparing paclitaxel alone to those treated with a combined paclitaxel and a *cannabis* extract. The control, or no treatment is not shown in FIG. 11, but results in more than 100% growth over the 21 days, as compared to the initial tumor volume. See, e.g., FIG. 8. What is striking, is what was seen in the organoid data and then repeated here. Combining a low dose of paclitaxel with an effective dose of any of the *cannabis* extracts yields dramatically greater reduction in tumor volume as compared to the paclitaxel alone or even the *cannabis* extracts alone at the given dose. As is shown in FIG. 11, paclitaxel is not highly effective at reducing tumor volume; at day 10 there is about a 37% decrease in volume, which does not really change over the next 11 days. In contrast, when combined with BSHE, there is a greater reduction in tumor volume as compared to paclitaxel. Thus, more paclitaxel (e.g., 6 doses more) does not produce a better effect than less paclitaxel (e.g., 6 doses in total) in combination with BSHE. At day 14 of treatment, there was about a 13% decrease in average tumor volume in mice treated with BSHE compared to those treated with paclitaxel alone, and about a 20% decrease in average tumor volume in mice treated with CBDA when compared to those treated with paclitaxel alone. This is quite amazing as a few days before average tumor volumes in mice treated with CBDA had increase by close to 40%. By day 21 of treatment, average tumor volumes for mice receiving the combined therapy were from about 22% to about 39% less than that of treatment with paclitaxel alone, an almost 80% decrease from initial measurements. Thus, coadministration of the *cannabis* extract comprising a known amount of CBD and paclitaxel was surprisingly more effective than their administration alone. Furthermore, this data supports the proposition that the *cannabis* extract comprising CBD provided to the human patient was in fact instrumental in procuring her remission and it was not due to chemotherapy treatment alone.

Figure 12A:
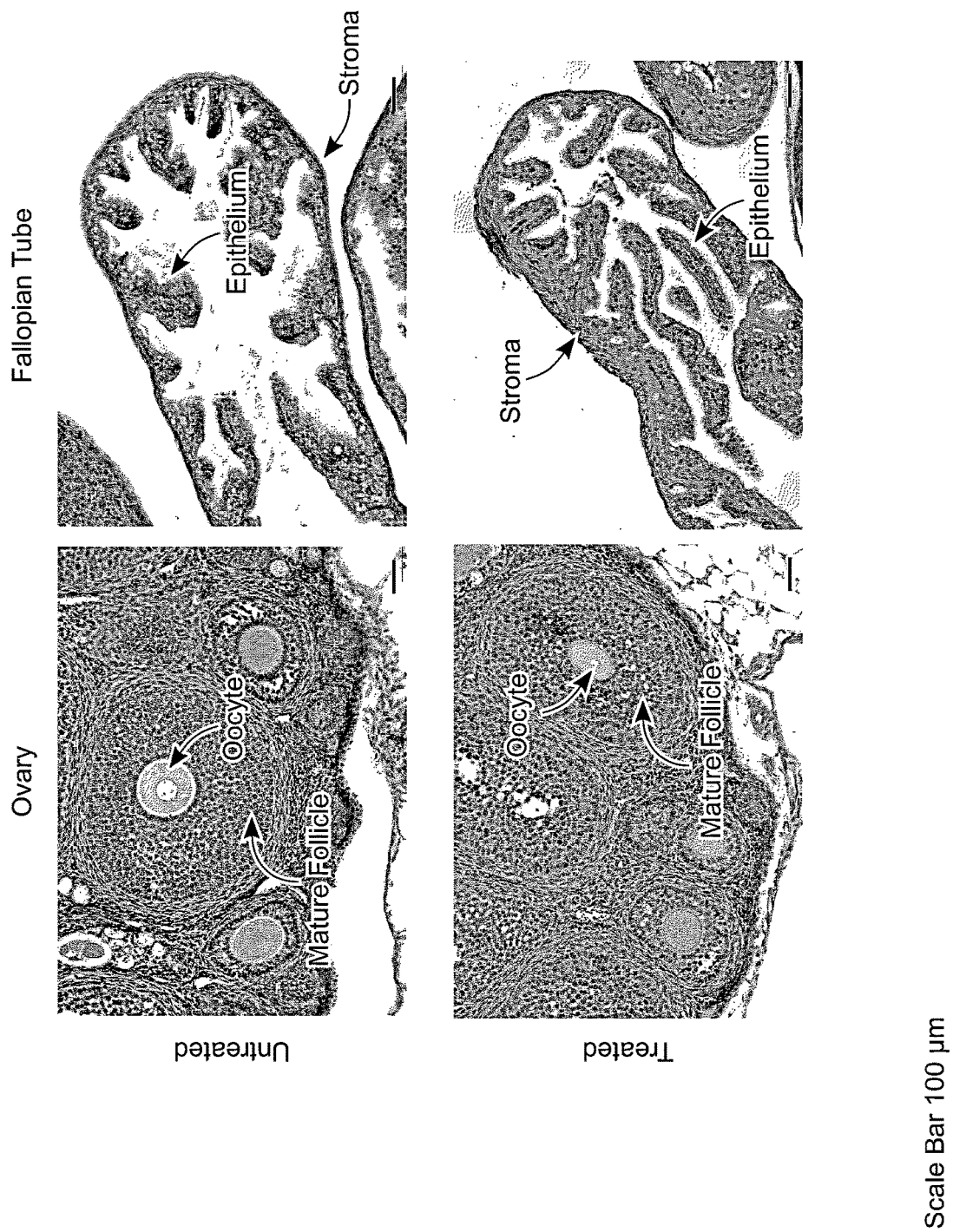
FIGS. 12A and 12B depict histological images of mouse tissues treated with *cannabis* extract comprising CBD showing that therapeutic treatment with the *cannabis* extracts comprising CBD does not damage the normal reproductive tract and liver cells.
Figure 12B:
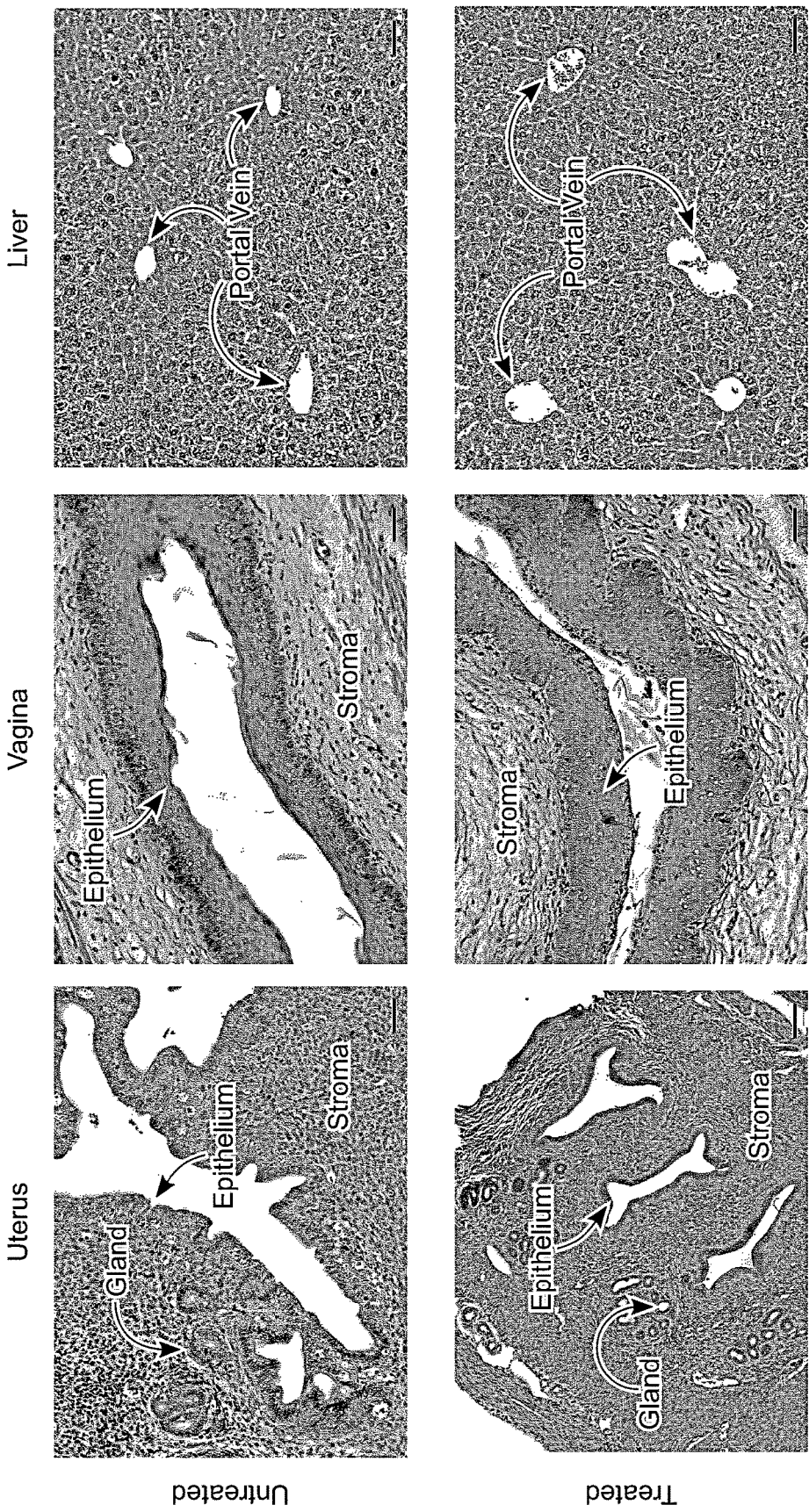

*Cannabis* extracts such as the ones used in our studies did not damage or adversely affect tissues of mice used in the patient-derived xenograft experiments. For example, FIGS. 12A and 12B compare histological tissue samples taken from the mice treated with a *cannabis* extract comprising CBD and healthy mouse tissue. FIG. 12A shows untreated and treated samples from ovaries and fallopian tubes. Chemotherapies are known to adversely affect oocytes and follicles. Here, the treated mice have mature oocytes and follicles that are both healthy. Likewise, healthy epithelial tissue is also known to be damaged by chemotherapy, often leading to severe organ/organ system damage that may be fatal. In comparing the untreated and treated epithelial tissue in mouse fallopian tube, both appear to be healthy. Similarly, tissues from treated and untreated mouse uteri, vaginas, and liver are compared in FIG. 12B. The liver is especially telling when damaged by chemotherapy. As can be seen in FIG. 12B, the liver samples are virtually identical. This is critically important, as treatment with high doses of chemotherapy are indiscriminate and damage these cells, when given over time. Thus, reduction in the quantity of chemotherapy drugs, whether at lower doses or none, in combination with the *cannabis* extract can improve the outcome for patients by decreasing tumor volume at a greater rate, reducing the tumor volume to a greater total percentage than chemotherapy alone, and does not otherwise cause damage to the corresponding, healthy tissues of the reproductive tract and the liver as would occur from chemotherapy use. CBD is non-toxic in non-transformed cells and does not affect physiological parameters (heart rate, blood pressure and body temperature), gastrointestinal transit or psychomotor or psychological functions. Chronic use and doses up to 1,500 mg/day of CBD are established as well tolerated in humans.

Moreover, CBD dominant *cannabis* extracts have no potential for abuse or dependence. This was best highlighted during the World Health Organization's 41$^{st}$ Expert Committee on Drug Dependence held in Geneva, Switzerland in November 2018. Annex 1 from the meeting's report states "cannabidiol should not be scheduled within the International Drug Control Conventions. Cannabidiol is found in *cannabis* and *cannabis* resin but does not have psychoactive properties and has no potential for abuse and no potential to produce dependence. It does not have significant ill-effects."

Figure 13:
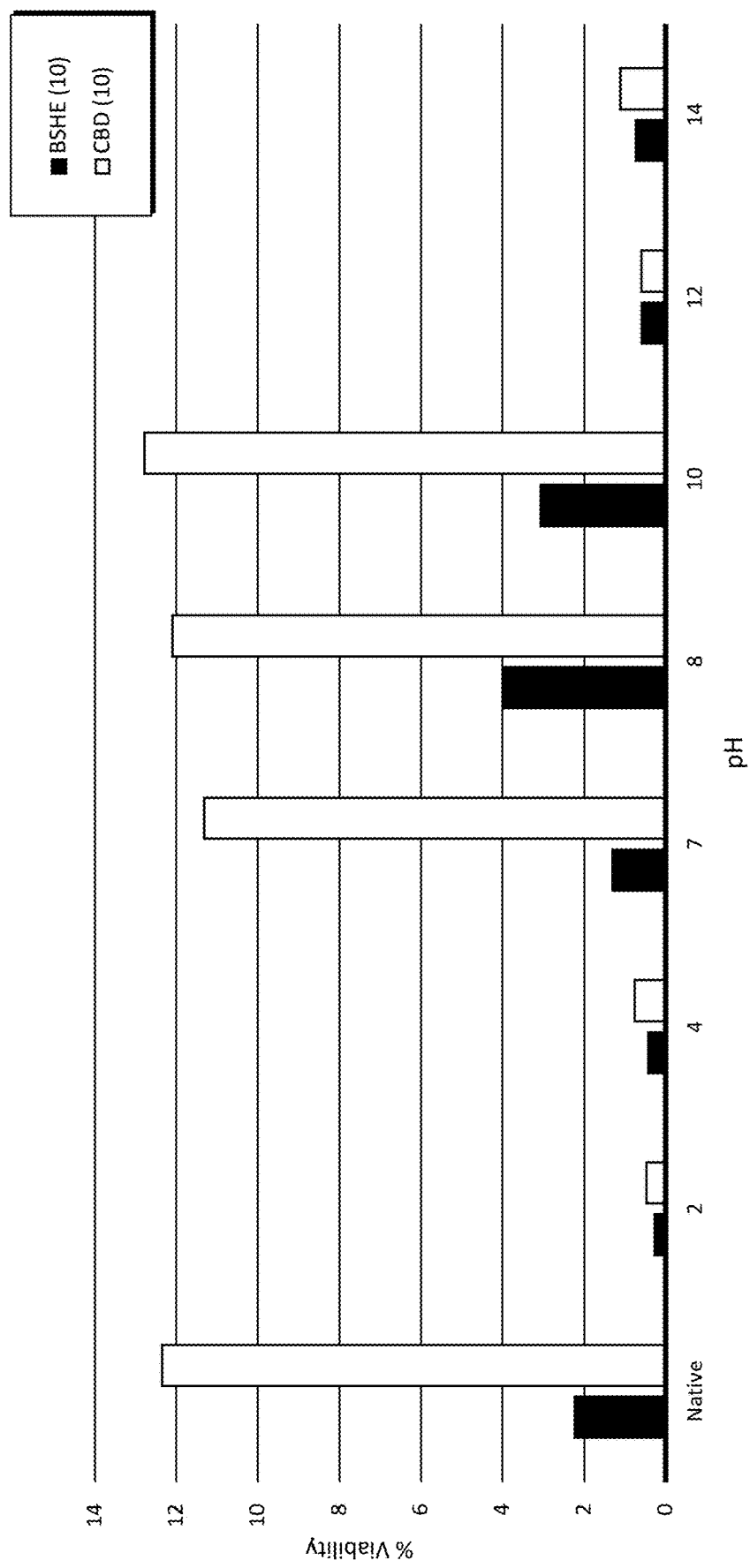
FIG. 13 depicts a chart showing the impacts of pH on therapeutic efficacy of the *cannabis* extracts comprising CBD.

A further interesting observation was made by looking at the impact of pH on the efficacy of *cannabis* extracts comprising CBD on the viability of organoids. Referring to FIG. 13, the % of viable organoids as a function of pH and BSHE and CBD isolate treatment, each at 10 μg/mL is show. In this set of experiments, organoids were derived from ovarian cancer tissue. Interestingly, the carrier alone did not destroy the organoids, and so the data is not depicted. At an extract's native pH, organoid production in the presence of 10 μg/mL BSHE was limited to about 2% and in the presence of the same amount of CBD isolate it was about 12%. However, increasing the pH led to substantial improvements in efficacy as is shown at the pH of 12 and 14. At this end of the pH scale substances tend to be corrosive, and at a pH of 14 are highly corrosive, alkaline concentrations that are not suitable for therapeutic use. Indeed, such a pH would not be isotonic, nor would it be appropriate for intravaginal application. The vagina has an acidic pH, which is necessary to maintain the balance of bacteria. However, strong modifications of the pH may lead to denaturing of the proteins or other problems. What was immediately evident is that the first attempts to buffer, even slightly, the pH to be more acidic, yielded worse results. Indeed, each of the two *cannabis* extracts examined in this test had less efficacy by decreasing pH from 10.5 to pH of about 10. Furthermore, reducing the pH to 8 again made the BSHE almost twice as weak at killing the organoids as the native pH, while the CBD isolate shows virtually no change. Even at pH of 7, a neutral pH, the changes are minimal at best.

In such a situation, decreasing the pH further would not likely lead to any further gains for therapeutic efficacy, as the changes were typically worse or virtually no change as compared to native pH. Instead, by further decreasing the pH to 4, a dramatic improvement in the % viability was seen for each of the BSHE and the CBD isolate, such that each were under a 1% viability, which was unexpected based on the prior data trending toward a worse response or virtually unchanged response. Accordingly, when providing the *cannabis* extract, especially where the *cannabis* extract is provided intravaginally or oromucosally, utilize a buffer to modify pH to between 2 and 6, yields a superior response compared to giving the *cannabis* extract at its native pH. Preferably, the *cannabis* extract is provided in a carrier with a pH of between 3.5 and 5.5, and more preferably at between a pH of between 4 and 5.

Summary of patient samples: The use of organoids to test the therapy is exciting as we can use representative cells to determine response to different therapies, instead of relying on analog models in other species. Accordingly, the results show that upon contact with the BSHE or FSHE comprising CBD, the organoids were destroyed across varying concentrations, but frequently as low as 5, 7, 10, or 20 μg/mL. This was shown in several different patients of varying stages and grades of endometrial cancer, all with the same success rates. Converting these numbers into mouse models, confirmed the same efficacy, wherein tumor growth was arrested and tumor volume was reduced, across the board.

Patients

A total of 12 patients, three with grade 1 endometrial cancer; one with grade 2 endometrial adenosquamous carcinoma; three with grade 2 endometrial adenocarcinoma, three with grade 2 endometrial cancer; one with grade 3 endometrial adenocarcinoma; and one with grade 3 endometrial cancer. One patient with grade 2 cancer is an undifferentiated cancer. All patients are aged between 39 to 80 years of age. The tissue samples were collected at time of surgery (total hysterectomy or total hysterectomy bilateral salpingo-oophorectomy) and disease was confirmed by the pathologist. Patients are consecutively and prospectively included when diagnosed with a pelvic mass of suspected uterine origin and are admitted for surgery for a clinically suspicious malignant endometrial growth. To be eligible for enrolment patients are required to be 18 years of age or older and have a diagnosis of endometrial cancer with a planned surgical intervention. Menopause status, defined as one year of amenorrhea, is checked for women between 47 and 56 years of age. Patients <47 years are considered premenopausal and women >56 years, postmenopausal. The exclusion criteria were: pregnancy, significant concomitant diseases such as chronic heart failure, severe chronic liver or renal disease, a prior bilateral oophorectomy, pelvic endometriosis or adenomyosis or ovarian primary tumors, and serious medical or psychiatric conditions that may prevent compliance with the protocol.

For some of the patients, a study of mutations was determined to ascertain genetic basis for the EC. Five of the EC patients EC were sampled and yielded the following mutations: Patient 1: ARID1A, HRAS, KMT2D, PTEN, TP53; patient 2: KRAS, MSH6, PMS2, TP53; Patient 3: ERBB3, JAK1, PTEN, TP53; patient 4: PIK3R1, POLE, PTEN, TP53; and patient 5: MAPK3, PIK3R1, PTEN, TP53. Each of these are patients have endometrial carcinoma.

Prior to the collection of biological samples and surgery, all patients are required to give full informed written consent. After surgery, the tumors are examined by an experienced gynecology pathologist for diagnosis, histology, grade, and stage (I-IV), according to the international federation of gynecology and obstetrics (FIGO) standards. Staging is also conducted by obtaining pelvic washings and performing bilateral pelvic and para-aortic lymph node dissection. Lymph node counts are not required. Only patients with complete surgical staging and pathologically confirmed endometrial cancers will be included in the study.

Embodiments

Therefore, the therapeutic treatment of metastatic endometrial cancerous growths was treated, by reduction of the tumor size and selective destruction of the endometrial cancer cells. Thus, endometrial cancer can be treated through the application of CBD intravaginally through application of a BSHE or FSHE as an intravaginal application. However, the dose can be repeated several times a day, wherein a total dose may be between 20 and 4250 mg a day. In preferred embodiments, a dose of between 25 and 1250 mg of CBD from a FSHE or BSHE is given at least once a day. In a preferred embodiment, the FSHE or BSHE comprises a fat or oil as a carrier for intravaginal application. And further comprises at least one terpene.

Intravaginal delivery is well studied and considered safe, effective and well tolerated. Intravaginal delivery avoids gastrointestinal absorption and bypasses first pass metabolism, while facilitating a localized effect and a steady, sustained therapeutic response. Absorption and systemic delivery via vaginal epithelium occurs rapidly with similar lipophilic compounds. Variances in thickness of the vaginal epithelium and vagina fluid characteristics, including pH, presence of cervical mucous, and microbiota, may influence absorption rates and bioavailability.

Rectal suppository delivery results in an increased bioavailability (51-60%) versus oral routes for CBD. Data on oromucosal or sublingual delivery, demonstrates that CBD has a maximum plasma concentration of 1.6 hours, but this can be delayed in some individuals. Oral CBD has a maximum plasma concentration of about 2.5-5 hours but can be delayed up to 6 hours for some individuals. Coadministration with high fat food has been shown to increase Cmax by up to 5-fold concentration. Delivery of CBD via highly vascularized nasal mucosa results in rapid uptake and a Tmax of approximately 10 minutes. The vaginal mucosa, however, has not yet been utilized for therapeutic treatments. Accordingly, CBD uptake through intravaginal absorption is remains an opportunistic route for administration as detailed herein.

Accordingly, mucosal dosing, particularly intravaginal dosing has a therapeutic efficacy that can allow for targeted treatment of EC cells, which will treat both localized tumors as well as metastasized tumors. These data were confirmed by further testing within human patients, which showed that treatment with CBD was effective in reducing chemoresistant EC, which had metastasized, in the body.

Therefore, in-patient treatment was effective in reducing the prevalence of endometrial cancer, which had spread throughout the body. Administration via intravaginal and oral mucosal administration showed a complete reduction in the size of the cancer cells via the PET scan. Accordingly, a first method is directed toward a method of treating an endometrial cancer, comprising administering to a patient in need thereof, an effective amount of a *cannabis* extract comprising CBD at a dose of between 5 mg to 5000 mg a day, wherein the dose is given via an oral, mucosal—such as intravaginal oral mucosal or other mucosa, dermally, or another form or combinations thereof.

Therefore, the therapeutic treatment of metastatic endometrial cancerous growths was treated, by reduction of the tumor size and selective destruction of the endometrial cancer cells. Can be treated through the application of CBD intravaginally through application of a BSHE or FSHE as an intravaginal application. However, the dose can be repeated several times a day, wherein a total dose may be between 20 and 500 mg a day. In preferred embodiments, a dose of between 25 and 250 mg of CBD from a FSHE or BSHE is given at least once a day. In a preferred embodiment, the FSHE or BSHE comprises a fat or oil as a carrier for intravaginal application, and further comprises at least one terpene.

Therefore, in-patient treatment was effective in reducing the prevalence of endometrial cancer, which had spread throughout the body. Administration via intravaginal and oral mucosal administration showed a complete reduction in the size of the cancer cells via the PET scan. Accordingly, a first method is directed toward a method of treating an endometrial cancer, comprising administering to a patient in need thereof, an effective amount of a *cannabis* extract comprising CBD at a dose of between 5 mg to 5000 mg a day, wherein the dose is given via an oral, mucosal—such as intravaginal oral mucosal or other mucosa, dermally, or another form or combinations thereof.

In preferred embodiments, the BSHE or FSHE comprise between 50 to 99.9% CBD. Accordingly, a 10 mg dose of BSHE or FSHE comprises between 5 to 9.9 mg of CBD. The remaining components of the BSHE or FSHE comprise additional cannabinoids, terpenes, polyphenols, essential fatty acids, and phytonutrients. When provided in a pharmaceutical composition, the concentration of CBD is typically between 5 and 50 mg/mL of a pharmaceutical composition. Certain compositions comprise additional excipients and ingredients, including but not limited to a fat, an oil, MCT oil, long chain triglyceride oils, very long chain triglyceride oils. Terpene components including but not limited to β-myrcene, β-caryophyllene, linalool, a pinene, citral, D-Limonene, Eucalyptol. Polyphenols may include, but are not limited to catechins, quercetin, cannflavin A/B/C, rutin, and chlorogenic acid. Omega 3, omega 6, and omega 9 fatty acids may be present, as well as additional phytonutrients such as tocopherol, sterols, carotene, aliphatic alcohols, and certain minerals. These components, including the carrier may make up to 90% by weight of the pharmaceutical composition, however, more preferably the CE comprising CBD comprises between 1 and 90% by weight of the pharmaceutical composition.

Therefore, a preferred embodiment is related to a method of treatment of an endometrial cancer comprising, administering to a patient an effective amount of a pharmaceutically acceptable composition comprising CBD, wherein the composition comprises a BSHE or FSHE. In preferred embodiments, an effective amount is one effective to generate a concentration of at least 10 µg/mL of the BSHE or FSHE at the target tissue. In a further preferred embodiment, an effective dose is between 10 and 4250 mg a day of CBD, wherein said CBD is provided in a CE, such as a BSHE or FSHE through mucosal dosing. The methods for treatment herein are effective in eliminating inappropriate lesions, i.e., cells that have migrated from their original location in the body. Furthermore, these methods stop or retard growth of the squamous cells or parent cells outside of their normal location without exerting unacceptable damage to the parent cells.

In a further embodiment, the method of treatment may be to relieve and treat a cancer selected from the group consisting of: adenocarcinomas, secretory carcinoma, ciliated carcinoma, villoglandular adenocarcinoma, squamous cell carcinomas, glandular epithelial cells, adenocarcinoma with squamous differentiation, adenosquamous carcinoma, adenoacanthoma, small cell carcinomas, transitional carcinomas, serous carcinomas, clear-cell carcinoma, mucinous adenocarcinoma, undifferentiated carcinoma, dedifferentiated carcinoma, serous adenocarcinoma, uterine carcinosarcoma, and combinations thereof.

In further embodiments, the method of treatment comprises treating these diseases through application of a pharmaceutically acceptable composition through mucosal administration, selected from one of oral mucosal, nasal mucosa, intravaginal, or rectal administration, said pharmaceutically acceptable composition comprising a CE, and preferably one of a BSHE or FSHE comprising CBD at between 75 and 99% of the total weight of the BSHE or FSHE, or a CBD isolate or CBDA isolate. In preferred embodiments, an effective amount is one effective to generate a concentration of at least 10 µg/mL of CBD at the target tissue. In a further preferred embodiment, an effective dose is between 10 and 4250 mg a day of CBD, wherein said CBD is provided in CE in a pharmaceutically acceptable carrier. In preferred embodiments, a combined therapy comprises an oral or oral mucosal therapeutic in addition to the intravaginal or rectal dose.

In preferred embodiments it is advantageous to modify the osmolality of the composition for therapeutic administration so as to be gentle for intravaginal dosing. In further preferred embodiments, it may be appropriate to modify the PH of the carrier so as to more appropriately match the pH of the vagina, which is typically acidic. Therefore, a preferred embodiment is a composition that has an acidic pH, preferably between 3.5 and 6, within a carrier suitable for intravaginal application.

For oral administration, it may be suitable to add or coadminister with a high-fat component to increase bioavailability, or to modify the pH or osmolality to increase the rate of absorption or the uptake of the CBD into the oral mucosa.

Therefore, the therapeutic treatment of endometrial cancer was treated, by reduction of the tumor size and selective destruction of the endometrial cancer cells. Can be treated through administering a CE comprising CBD. Based on the needs of the patient, the administration is preferably through a mucosal dosing route, such as intravaginally, oromucosally, rectally, or within the nasal passage, or two or more of these dosing routes. A dose can be provided once every three days, every second day, every day, daily, or several times a day, such as two, three, four or more times a day. The therapeutic dose is preferably between 20 and 4250 mg a day. In preferred embodiments, a dose of between 25 and 1250 mg of CBD from a FSHE or BSHE is given at least once a day. In a preferred embodiment, the FSHE or BSHE is part of a composition comprising a carrier to aid in administering the CE. Preferably the carrier is a fat or oil as a carrier for mucosal delivery. In a preferred embodiment, the FSHE or BSHE comprises a fat or oil as a carrier for mucosal application. In another preferred embodiment, the FSHE or BSHE comprises at least one terpene. In a more preferred embodiment, the FSHE or BSHE comprises a fat or oil as a carrier for intravaginal application, and further comprises at least one terpene. Additional excipients or delivery matrix may be further added based on the route of administration. The CE preferably comprises CBD from 50-99.9% of the weight of the CE. However, the CE preferably further includes at least one additional cannabinoid such as, CBC, CBG, CBD, CBDA, CBDV, $\Delta^9$-THC, wherein the total concentration of the one additional cannabinoid is between 0.1 and 49%. In further embodiments, the CE may also comprise at least one of a terpene, a polyphenol, a fatty acid, or a phytonutrient. Each of these are preferably derived from the *cannabis* plant and present due to the extraction process.

In a preferred embodiment, treatment of endometrial cancer comprises treatment with both a chemotherapeutic agent and also a CE comprising CBD. The CE is administered as provided above. The chemotherapeutic agent is administered in its normal route of administration. However, the chemotherapeutic agent is preferably administered at a reduced dose as compared to its normal dose. The reduced dose is possible based upon the determined synergy between the chemotherapeutic agent and the CE. Administration of the CE may be by any suitable route, however, it is preferred for oromucosal treatment to allow for high bioavailability of the CBD adjacent to the lymph nodes in the mouth and throat, as well as reducing the first pass metabolism through mucosal dosing. The CE is preferably a FSHE or a BSHE, wherein the concentration of CBD is preferably at least 50%, and more preferably, at least 60, 65, 70, 75, 80, 85, 90, or 95%, with the remaining portion of the FSHE or the BSHE comprising at least one additional cannabinoid at a concentration of between 0.1 to 40% by weight of the CE. Most preferably, the FSHE or the BSHE comprise at least two cannabinoids, each having a concentration of at least 0.1% by weight of the CE. Most preferably the additional cannabinoid is one or more of: $\Delta^9$-THC, THCA, THCV, $\Delta^8$-THC, CBC, CBCA, CBG, CBGA, CBDA, CBDV, CBN, CBL, and combinations thereof.

In certain embodiments, the treatment is indicated for chemosensitve endometrial cancer. In such an instance, CE with CBD alone may be sufficient, or administered jointly with a chemotherapeutic agent. In certain other embodiments, the treatment is indicated for metastatic chemosensitive endometrial cancer, wherein the endometrial cancer cells have metastasized and spread beyond the uterus. In certain embodiments the endometrial cancer is a chemoresistant cancer.

In certain embodiments, personalized medicine may play a critical role in providing optimized therapeutic treatments. Thus, a patient having endometrial cancer may obtain a tissue sample for creation of organoids. The tissue sample is typically taken from a biopsy or resected cancerous tissues. The organoids can then be grown and tested against a panel of chemotherapeutic agents to identify an optimized treatment plan. The preferred plan is to utilize as low a dose of chemotherapeutic agent as possible, in combination with a CE, in order to eradicate the organoids. Thereafter, treatment of the patient with the optimized chemotherapeutic agent and the CE will provide an optimized therapeutic treatment plan. As noted herein, chemotherapeutic agents are highly toxic and the ability to reduce the quantity and number of chemotherapy rounds provides a significant improvement to the cancer treatment, as the significant side effects from chemotherapy can be reduced.

In preferred methods, the *cannabis* extract is a BSHE. In preferred methods, the BSHE comprises from between 50 and 99% of CBD, and at least one additional cannabinoid. In certain embodiments, the BSHE comprises at least two additional cannabinoids. In further embodiments, the CE comprises at least three additional cannabinoids. In preferred embodiments, the additional cannabinoids are selected from the group consisting of: $\Delta^9$-THC, THCA, THCV, $\Delta^8$-THC, CBC, CBCA, CBG, CBGA, CBDA, CBDV, CBN, CBL, and combinations thereof.

In certain embodiments the *cannabis* extract is a FSHE, comprising at least 0.01 to 5.0% $\Delta^9$-THC. In preferred embodiments, a FSHE comprises between 50 and 99% CBD, and between 0.01 to 0.3% of $\Delta^9$-THC. Preferably, the FSHE comprises a total of 51 to 99.9% total cannabinoids, with a total of THC, including $\Delta^8$-THC, $\Delta^9$-THC, $\Delta^9$-THCV, THCV, and THCVA comprising 0.1 to 10% by weight of the CE.

In further preferred methods, the CE is an isolate of CBD derived from a *cannabis* extract. Thus, the CBD isolate seeks to concentrate the CBD, with the CBD being present at between 70 and 99.9% by weight of the CE. In certain preferred embodiments, the isolate of CBD further comprises at least one additional cannabinoid. In preferred embodiments, the isolated CBD further comprises CBN, CBDA or both at a concentration of between 0.1 and 10%.

THC and CBD are both highly lipophilic and have poor oral bioavailability when swallowed, at between 6 to 10 percent, amounts which may be increased through specific preparations. Oral THC formulations exhibit variable absorption and undergo extensive hepatic first-pass metabolism, resulting in lower peak plasma THC concentration relative to inhalation and a longer onset (~120 min) to reach peak concentration. Following oral administration of CBD, a similar plasma concentration-time profile to that of oral THC has been observed. Based on this profile, oral formulations may be useful for patients requiring symptomatic relief over a longer period, though higher concentrations may be necessary, in order to reach therapeutic plasma concentrations, as compared to alternative delivery methods, such as inhalation. Furthermore, certain liver toxicities may exist because of the extensive first pass metabolism when higher dosage amounts are needed for therapeutic levels.

Transdermal administration of cannabinoids, however, avoids first-pass metabolism but the extremely hydrophobic nature and high molecular weights of cannabinoids limits diffusion across the aqueous layer of the dermis. This rate limiting step may only be modified by permeation enhancement, or by enhancement or manipulation of the molecule, such as in delivery tools, or as a pro-drug. Effective dermal transport is typically only obtained by permeation enhancement. However, mucosal transport, either through the oral mucosa, nasal mucosa, vaginal mucosa, or rectal mucosa have different properties as compared to the dermal layer, and thus allow for greater diffusion over these tissues. Even so, in vitro studies with human skin have determined the permeability potential of CBD to be 10-fold higher than that of $\Delta^9$-THC and $\Delta^8$-THC, consistent with CBD being relatively less lipophilic. This leads to opportunities for CBD for topical administration that are relatively unavailable for $\Delta^9$-THC, and which would be further improved for mucosal administration, which does not contain all of the systemic diffusion challenges of overcoming the barrier function of dermal skin layers.

Oral mucosal preparations undergo rapid absorption via the oral mucosa (and hence are useful for symptoms requiring rapid relief), producing plasma drug concentrations higher relative to oral delivery, but reduced relative to inhaled (smoke) consumption of *cannabis* material. However, even when utilizing oral mucosal preparations, part of the dose will be swallowed and thus ingested via the stomach, thus a portion becoming a standard oral formulation.

Cannabinoids rapidly distribute into well-vascularized organs (e.g., lung, heart, brain, liver), with subsequent equilibration into less vascularized tissue. Distribution may be affected by body size and composition, and disease states influencing the permeability of blood-tissue barriers. Therefore, when targeting less vascularized organs, the distribution and uptake may be reduced, as compared to other organs. This again points to implications for localized administration for EC treatment, instead of simply through the stomach or oral mucosa as with typical applications of therapeutic treatments.

CBD is hepatically metabolized, primarily by isozymes CYP450, CYP2C19 and CYP3A4 and additionally, CYP1A1, CYP1A2, CYP2C9 and CYP2D6. After hydroxylation to 7-hydroxy cannabidiol (7-OH-CBD), there is further hepatic metabolism and subsequent fecal, and, to a lesser extent, urinary, excretion of those metabolites. CBD, like TUC, has also been reported to have a long terminal elimination half-life, with the average half-life following intravenous dosing observed to be 24±6 hours and post-inhalation to be 31±4 hours. An investigation of repeated daily oral administration of CBD elicited an elimination half-life ranging from 2 to 5 days. A relatively longer elimination half-life is observed in heavy users, attributable to slow redistribution from deep compartments such as fatty tissues. Indeed, both THC and CBD are known to accumulate in adipose tissues with recurring administration. Consequently, THC and CBD concentrations 1 µg $l^{-1}$ may be measurable in the blood of heavy users more than 24 h following the last *cannabis* use.

Dose-response and drug-drug interaction information is lacking. Potential exists for pharmacokinetic interactions between both TIC and CBD and other drugs, via inhibition or induction of enzymes or transporters and additionally, pharmacodynamic drug-drug interactions. There is a potential for CBD to compete with drugs metabolized through CYP 450 pathways, specifically those that interact with enzymes CYP3A4, CYP2C19, and CYP2D6. Dose adjustments may be necessary with substrates of CYP2C8, CYP2C9, CYP2C19, CYP1A2 and CYP2B6. Current literature demonstrates clinically significant drug interactions at doses of 20 mg/kg/day. One published case study concluded meaningful interactions with Warfarin at a dose of 10 mg/kg.

An in vitro study reported that CBD significantly inhibits P-glycoprotein-mediated drug transport, suggesting that CBD could potentially influence the absorption and disposition of other coadministered drugs. Coadministration of rifampicin (a CYP3A4 inducer) significantly reduced peak plasma concentrations of CBD, while coadministration of the CYP3A4 inhibitor ketoconazole nearly doubled peak plasma drug concentrations. Accordingly, it may be useful to coadminister a CYP3A4 inhibitor with CBD in order to reach higher blood plasma concentrations, or to reduce the total amount of CBD administered to reach therapeutic levels. Furthermore, In vitro, CBD was observed to be a potent inhibitor of CYP2C19 enzymes.

THC is a partial agonist of CB1 receptors, the mechanism by which intoxication and psychotropic effects of *cannabis* can occur. As CBD does not bind with (CB1 receptors, THC elicited anxiety, dysphoria, sedation, psychotic symptoms, subjective intoxication, and increased heart rate, while CBD demonstrated zero adverse effects in controlled studies of the molecules. Thus, CBD does not possess the risk of intoxication, dependency or withdrawal associated with THC. CBD is a potent antagonist and allosteric modulator of CB1 receptors, therefore inhibiting some of the intoxicating and other adverse effects of THC when coadministered. Thus, coadministration of CBD has been reported to reduce THC-associated adverse psychotropic and cardiovascular effects (tachycardia). CBD has been reportedly associated with fatigue and somnolence, potentially compounded by coadministration with CNS-active medications.

Application of CBD to patients for gynecological cancers is specifically targeted at intravaginal application of the broad spectrum CBD. Notably, patients after surgery were provided with intravaginal broad spectrum CBD, to both target remaining lesions and growths that were not completely removed by resection, but also to specifically to address metastatic disease by preventing the spread of metastatic cells or re eliminate those which have already spread through the body. For dosing and administration of the *cannabis* extracts, the intravaginal application may be superior as it specifically targets the gynecological cancers by uptake at or adjacent to the cancer cells, and then provides for rapid systemic uptake. This provides for direct application to the gynecological organs as well as for the systemic influence to reach both the localized cancers and metastatic cancers. In the human trials, this was effective in reducing the tumor volume in all of the prior identified tumors, in any of the body organs.

In preparing a composition for administration to a patient the CE, in certain embodiments, can be administered without the need for an additional carrier. Thus, a composition suitable for administration to a patient may be the CE without any further carrier or excipient.

However, in preferred embodiments the CE is provided in a composition for treatment of endometrial cancer, wherein the composition comprises a *cannabis* extract (CE), wherein the CE comprises between 1 and 99% by weight of the composition and all percentages therein, and a carrier. In preferred embodiments, the CE comprises between 10 and 90% by weight, or 20 by 90% by weight, and preferably between 40 and 80% by weight of the composition. The CE, as detailed herein, is preferably a BSHE, a FSHE, a CBD isolate, or a CBDA isolate. In each of these different CE, the BSHE, the FSHE, the CBD isolate, or the CBDA isolate, they make up between 50 and 99.9% by weight of the CE, with the remaining being waxes, fats, fatty acids and the like. However, preferred embodiments utilize a carrier at between 1 and 99% by weight of the composition, and preferably, one or more additional excipients depending on the use case of the composition. The composition is typically then administered based upon the dosage in mg of CBD being administered. Wherein the amount of the composition required to meet that mg of CBD depends on the quantity of CBD within each of the CE.

Therefore, methods of treatment of endometrial cancers are effective through an intravaginal application and coadministration with an oral mucosal dose. In preferred embodiments, the *cannabis* extract comprises between 50 to 100% CBD, with the remaining being excipients and may further comprise additional cannabinoids, terpenes, polyphenols, essential fatty acids, and phytonutrients. Accordingly, a 10 mg dose of BSHE or FSHE comprises between 5 to 10 mg of CBD.

Preferably, a composition comprises a CE, wherein the CE is 1-99.9% by weight of the composition, and most preferably between 50 and 99% by weight of the composition. When provided in a pharmaceutical composition, the concentration of CBD is typically between 5 and 50 mg/mL of a pharmaceutical composition. Certain compositions comprise additional excipients and ingredients, including but not limited to a fat, an oil, MCT oil, long chain triglyceride oils, very long chain triglyceride oils. Terpene components including but not limited to β-myrcene, β-caryophyllene, linalool, αpinene, citral, D-Limonene, Eucalyptol. Polyphenols may include, but are not limited to catechins, quercetin, cannflavin A/B/C, rutin, and chlorogenic acid. Omega 3, omega 6, and omega 9 fatty acids may be present, as well as additional phytonutrients such as tocopherol, sterols, carotene, aliphatic alcohols, and certain minerals. These components, including the carrier may make up to 90% by weight of the pharmaceutical composition, however, more preferably the CE, comprising the CBD comprises between 1 and 99.9% of the pharmaceutical composition.

Therefore, a preferred embodiment is related to a method of treatment of endometrial cancer comprising, administering to a patient an effective amount of a pharmaceutically acceptably composition comprising a *cannabis* extract. In preferred embodiments, an effective amount is one effective to generate a concentration of at least 10 µg/mL of the BSHE or FSHE at the target tissue. In a further preferred embodiment, an effective dose is between 10 and 1000 mg a day of CBD, wherein said CBD is provided as a *cannabis* extract. In a preferred embodiment, the *cannabis* extract is selected from the group consisting of: a BSHE, a FSHE, a CBD isolate or CBDA. In preferred embodiments the *cannabis* extract is administered to the patient via an intravaginal application, orally, or through a mucosal substrate.

In a further preferred embodiment, a method of treatment of endometrial cancer comprising, administering to a patient an effective amount of CBD from a BSHE or FSHE. In preferred embodiments, an effective dose is one effective to generate a concentration of at least 10 µg/mL of BSHE or FSHE at the target tissue. In a further preferred embodiment, an effective dose is between 25 and 500 mg of CBD, given once, twice, three, or more times a day to a patient, wherein said CBD is provided in a *cannabis* extract through an intravaginal application, or through an oral or oral mucosal application, or a combination thereof.

In a further preferred embodiment, a method of treatment of chemoresistant endometrial cancer, comprising administering to a patient an effective amount of CBD from a *cannabis* extract. In preferred embodiments, an effective dose is one effective to generate a concentration of at least 10 µg/mL of BSHE or FSHE at the target tissue. In a further preferred embodiment, an effective dose is between 25 and 500 mg of CBD, wherein said CBD is provided in a *cannabis* extract through an intravaginal, oral, or oral mucosal application, or combinations thereof. In certain embodiments, a patient is first tested for chemoresistance to their particular cancer, and upon confirmation of chemoresistance, treating with the effective amount of CBD.

In preferred embodiments, the *cannabis* extract is provided in a pharmaceutically acceptable composition, comprising a suitable carrier and excipients for intravaginal dosing, wherein the active ingredients from the *cannabis* extract pass through the vaginal membrane to target tissues in the female reproductive system as well as obtaining systemic uptake of the active ingredients for systemic distribution.

In certain other applications, it may be suitable to coadminister the *cannabis* extract treatment with an ongoing radiation or chemotherapeutic treatment. Therapeutic coadministration may be suitable for increasing efficacy and/or decreasing the dose and thus toxicity related to chemotherapeutic treatment.

In further preferred embodiments, it may be appropriate to modify the PH of the carrier so as to more appropriately match the pH of the vagina, which is typically acidic. Preferably, the pH of the compositions as administered is between 3.5 and 6, and more preferably between 3.75 and 5.5.

Definitions

As used herein, the term "about" means plus or minus 5% of the numerical value of the number with which it is being used. Therefore, about 50% means in the range of 45%-55%, about 20 mg means the range including 19 mg to 21 mg, and the like "Administering" when used in conjunction with a therapeutic means to administer a therapeutic directly to a subject, whereby the agent positively impacts the target. "Administering" the therapeutic drug or compound may be accomplished by, for example, injection, oral administration, topical administration, mucosal administration and/or in combination with other known techniques. The administering techniques may further include heating, radiation, chemotherapy, ultrasound, and the use of delivery agents. Preferably in the present disclosure the administration is through oral, oral mucosal/sublingual, and/or intravaginal dosage forms. Such intravaginal forms are intended to be inserted into the vagina, typically with a carrier, wherein the active ingredients pass through the vaginal mucosal membrane. The active ingredients may also be provided in an oral form, to be swallowed. Another oral form is an oral mucosal application, which is often provided as a sublingual application, which, while it is ultimately swallowed to enter the stomach, is intended to be held in the mouth, for example under the tongue, and the active ingredients pass through the oral mucosal membrane before being swallowed or passed into the stomach by salivary action or active swallowing of the materials or both.

As used herein, "broad spectrum hemp extract" (BSHE) is a composition derived from the *Cannabis* genus of plants which has undergone at least some purification in order to refine the extract. Typically, BSHE comprises between 60 and 99.9% CBD and least one additional cannabinoid, selected from the group consisting of $\Delta^9$-THC, THCA, THCV, $\Delta^8$-THC, CBC, CBCA, CBG, CBGA, CBDA, CBDV, CBN, CBL, and combinations thereof at between 0.1 and 40%.

As used herein "*cannabis* extract" (CE) and "*cannabis* extract comprising CBD" is a composition derived from the *Cannabis* genus of plants (including hemp). Typically, a *cannabis* extract contains cannabidiol (CBD), and more typically comprises both CBD and at least one additional cannabinoid selected from the group consisting of $\Delta^9$-THC, THCA, THCV, $\Delta^8$-THC, CBC, CBCA, CBG, CBGA, CBDA, CBDV, CBN, CBL, and combinations thereof at between 0.1 and 40%. *Cannabis* extracts according to the present invention are typically enriched in cannabidiol, and may comprise between 1 and 99.9% CBD, preferably between 20 and 99.9% CBD, more preferably between 50 and 99.9% CBD, even more preferably between 70 and 99.9% CBD, and most preferably between 90 and 99.9% CBD. Full spectrum hemp extract, broad spectrum hemp extract, CBD isolate, and CBDA isolate are forms of *cannabis* extract utilized herein, as non-limiting examples of the CE. Throughout the application, the term CBD is often used interchangeably with CE, to mean the CE product containing the particular amount of CBD, while in other instances, which are obvious to the reader, the CBD refers to a CBD isolate, which means the CE was processed to remove and isolate CBD, removing virtually all other components of the CE.

As used herein, "coadministering" means administering a *cannabis* extract and the chemotherapeutic agent no more than 72 hours apart, preferably no more than 48 hours apart, and more preferably no more than 24 hours apart, for example no more than 12 hours apart, no more than 6 hours apart, no more than 4 hours apart, no more than 3 hours apart, no more than 2 hours apart, no more than one hour apart, no more than 30 minutes apart, or simultaneously.

As used herein, "concomitantly" means a first formulation and a second formulation administered to a patient no more than 72 hours apart, preferably no more than 48 hours apart, and more preferably no more than 24 hours apart, for example no more than 12 hours apart, no more than 6 hours apart, no more than 4 hours apart, no more than 3 hours apart, no more than 2 hours apart, no more than one hour apart, no more than 30 minutes apart, or simultaneously.

As used herein, "full spectrum hemp extract" (FSHE) is a composition derived from the *Cannabis* genus of plants which contains CBD, and quantities of $\Delta^9$-THC above 0, preferably, between 0.01 and 5%, most preferably being between 0.01% and 0.3%. The FSHE may comprise additional cannabinoids, yielding a product that comprises at least 50-99% CBD, at least 0.01 to 10% THC ($\Delta^9$-THC, THCA, THCV, $\Delta^8$-THC), and total cannabinoids of between 50% and 99% of the weight of the CE.

For the purposes of the present application, "hemp" is a *cannabis* plant having a $\Delta$-$^9$-THC content of 0.3% or less by dried weight.

By "pharmaceutically acceptable," it is meant that the components including, but not limited to the carrier, diluent, adjuvant, or excipient must be compatible with the other ingredients of the formulation and not deleterious to the recipient thereof.

As used here, the term "composition" is intended to encompass a product comprising the specified ingredients in the specified amounts, as well as any product which results, directly or indirectly, from combination of the specified ingredients in the specified amounts. Such term in relation to "pharmaceutical composition" is intended to encompass a product comprising the active ingredient(s) and the inert ingredient(s) that make up the carrier, as well as any product which results, directly or indirectly, from combination, complexation, or aggregation of any two or more of the ingredients or from dissociation of one or more of the ingredients, or from other types of reactions or interactions of one or more of the ingredients. Accordingly, the pharmaceutical compositions of the present invention encompass any composition made by admixing a compound or compounds of the present invention and a pharmaceutically acceptable carrier.

As used herein, the terms "agent," "active agent," "therapeutic agent," or "therapeutic" mean a compound or composition utilized to treat, combat, ameliorate, prevent, or improve an unwanted condition or disease of a patient. Furthermore, the terms "agent," "active agent," "therapeutic agent," or "therapeutic" encompass a *cannabis* extract and/or additional agents as described in the present disclosure.

A "therapeutically effective amount" or "effective amount" of a composition is a predetermined amount calculated to achieve the desired effect, i.e., to inhibit, block, or reverse the activation, migration, proliferation, alteration of cellular function, and to preserve the normal function of cells. The activity contemplated by the methods described herein includes both medical therapeutic and/or prophylactic treatment, as appropriate, and the compositions of the invention may be used to provide improvement in any of the conditions described. It is also contemplated that the compositions described herein may be administered to healthy subjects or individuals not exhibiting symptoms but who may be at risk of developing a particular disorder. The specific dose of a compound administered according to this invention to obtain therapeutic and/or prophylactic effects will, of course, be determined by the particular circumstances surrounding the case, including, for example, the compound administered, the route of administration, and the condition being treated. However, it will be understood that the chosen dosage ranges are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue to achieve the therapeutic response. Specifically, the therapeutic shall be effective in treating cancerous growths related to endometrial cancer, and metastatic disease relating thereto.

The terms "treat," "treated," or "treating" as used herein refer to both therapeutic treatment and prophylactic or preventative measures wherein the object is to prevent or slow down (lessen) an undesired physiological condition, disorder, or disease, or to obtain beneficial or desired clinical results. For the purposes of this disclosure, beneficial or desired results include, but are not limited to, alleviation of symptoms; diminishment of the extent of the condition, disorder, or disease such as a reduction in the size of a tumor; stabilization (i.e., not worsening) of the state of the condition, disorder, or disease; delay in onset or slowing of the progression of the condition, disorder, or disease; amelioration of the condition, disorder, or disease state; and remission (whether partial or total), whether detectable or undetectable, or enhancement or improvement of the condition, disorder, or disease.

Methods and Calculations
Patient-Derived Organoids

Patient derived organoids were created by collecting endometrial cancer tissue samples after surgery. The collected tissue was bathed, on ice, in Hank's Balanced Salt Solution (HBSS) (Hyclone, SH30031.02) with 1% Penicillin/Streptomycin (P/S) (Life Technologies, 15070-063). The tissue sample was washed three times with Dulbecco's phosphate-buffered saline (DPBS) and 1% P/S on a shaker (70 rpm) for 15 minutes each wash. Thereafter, the tissue sample was finely minced with a sterile blade while in a pre-sterilized cell-culture hood. All minced parts were enzymatically digested (Accumax™—Innovative Cell Technologies Inc., AM105-500) for about 2.5 hours at room temperature. After 2.5-hours, the whole digested tissue mince was transferred for further enzyme digestion with TrypLE™ express, (Gibco, 12604-021) for another 45 minutes in a 37° C. water bath. During this time, the solution was continuously agitated in 5 minutes intervals. Thereafter, the solution of digested tissue was passed through a 70 µm filter on a 50 mL falcon tube. The filter was removed and the flow-through with the cells was collected in 5% FBS AD+++ medium (comprising 1% ITS, 2% B27, 1% N2, 25% WRN, hegf-50 ng/mL, hfgf-10-100 ng/mL, Nicotinamide-1 mM, N-acetyl cysteine-1.25 mM, Primocin-0.2%, Estrogen-2 nm, A8301-0.5 uM, and Y27632). This cell suspension was centrifuged at 1000 rpm for 5 minutes at room temperature to get a cell pellet for counting. Upon checking under hemocytometer cell number was calculated and processed for organoid culture. Final cell suspensions were checked under a microscope for RBC contamination and if found, the RBCs were lysed used Red Blood Cell Lysis Buffer (Roche Diagnostics, 11814389001). The resultant endometrial cancer cells from a human patient were grown and maintained in a humidified chamber at 37° C. with 5% $CO_2$.

Organoids derived from ascites samples were treated somewhat differently; the ascites fluid was centrifuged at 1000 rpm for 10 minutes at room temperature to get a cell suspension. The cell suspension was then treated with Red Blood Cell Lysis Buffer (Roche Diagnostics, 11814389001) to remove the RBC from the final cell suspension.

To culture patient-derived organoids, $2-3\times10^{\wedge}3$ cells were plated in a pre-warmed (37° C.) 96-well plate in 10 µL of Matrigel (5% FBS AD+++ medium) per well. Individual patient cell organoids were cultured separately in different plates. Individual patient cells were handled separately to reduce the chance of cross-contamination. After mixing cells with Matrigel, 10 µL droplets were placed in wells and put in a 37° C. incubator with 5% $CO_2$ for 30 minutes. Upon solidification of the Matrigel droplet with cells inside, the plate was placed inside a sterile hood and immersed the Matrigel droplet in 200 µL of organoid growth media. Cells were allowed to grow into mature organoids for 14 days. Treatment with individual CBD agents (Broad Spectrum, Full Spectrum, CBD Isolate, and CBDA) or in combination with chemotherapeutic agents (Paclitaxel or Carboplatin) was usually started on day 5, where the individual drug or drug combinations were added in the growth medium. All treatments were done in triplicate, including vehicle-only controls (Dimethyl sulfoxide in culture medium at the highest concentration used for drug treatments).

Some human equivalent doses were calculated using a standard formula: (M=m/MW*1/V where m=mass in grams, MW=molecular weight of the substance and V=volume of the diluent in liters). For example, if organoids are dosed with 54.35 µM Drug X, 0.0032 mg of Drug X are needed in 100 µL or 0.0001 L (V) of solute. That is equivalent to 0.00005435 M or 54.35 µM concentration, where the MW of Drug X=588.72 g/mol and m=0.0000032 g.

When using the 96 well plates, the following formula is used for translating the given dose to a human dosage. The surface area of a single well in a 96 well plates is 0.32 $cm^2$. Thus, the clinical dose equivalent (mg/$m^2$) is 100 mg/$m^2$ by following the formula: Clinical Dosage (mg/$m^2$)=(PDO dosage in mg/culture plate surface area $cm^2$)×$100^2$. When comparing the two different methods of translating the organoid dose to the human dose, the two calculations show a similar human equivalent dose, for example of approximately 200 mg/day for the organoid equivalent of 10 µg/mL.

The IC50 is the 50% inhibitory concentration which is conventionally used to determine drug potency with cell-based cytotoxicity tests. To determine the IC50 for specific patient-derived organoids, individual patient organoids were treated with each of BSHE, FSHE, CBD Isolate, and CBDA as described above. Results of such treatment were used to find individual IC50s by using least squares regression (in Graphpad Prism 9) on inhibitor (i.e., a particular *cannabis* extract) vs normalized response-variable slopes. Thus, an IC50 was determined for each cannabinoid extract and selected patient-derived organoids. Thereafter, for each of the patient-derived organoids selected for testing a *cannabis* extract with CBD in combination with a chemotherapeutic agent, the organoids were treated with either the chemotherapeutic agent alone, or the chemotherapeutic agent in combination with a dosage of the cannabinoid extract equivalent to the calculated IC50 for the particular extract/organoid combination. The same IC50 dose was given with each incremental dose of chemotherapeutic agent. Notably, the doses given for each chemotherapeutic agent in the organoids are below an equivalent of a maximal doses suitable for human administration. In this way, we could determine if a specific IC50 of a given *cannabis* extract comprising CBD and a reduced amount of chemotherapeutic agent (Paclitaxel, Doxorubicin or Carboplatin) could be used to obtain the same amount of cancer cell death as of a standard human dose of a chemotherapeutic agent.

Cell Viability Assay

To assess the cell viability in organoids after treatment, CellTiter-Glo® Luminescent Assay (Promega #G7572) was used. In brief, on day 14 of organoid culture, the Matrigel droplet in each well with organoid inside was immersed in 100 µL of fresh growth media and 100 µL of CellTiter-Glo® reagent following the manufacturer's guideline. Blank wells containing only media and CellTiter Glo® reagent (no cells) were also included in each plate. Then the plates were put on a shaker @ 110 rpm at room temperature for 5 minutes to induce cell lysis, followed by 25 minutes at room temperature to stabilize the luminescent signal. Each step after adding the CellTiter Glo® reagent was performed in the dark. Luminescence was measured on a FLUOstar OPTIMA plate reader (BMG Lab technologies, Offenburg, Germany). Analysis was performed by normalizing treatment values to the vehicle control and plotting them as a percentage of the vehicle control. Drug IC50 values were determined by inhibitor vs normalized response-variable slope using least squares regression in Graphpad Prism 9.

Patient-Derived Xenograft (PDX) Mouse Generation

Human patient cells from endometrial cancer were injected subcutaneously into female NOD/SCID gamma mice after resuspending in 100 µL solution. Once the tumor grew to a visible size all mice were intraperitoneally injected with single *cannabis* extract comprising CBD agent using the extract alone at 10-30 mg/kg body weight or the *cannabis* extract comprising CBD agent together with a given chemotherapeutics where the given *cannabis* extract was given at 10-30 mg/kg body weight, Paclitaxel was given at up to 20 mg/kg body weight or the vehicle thrice per week for up to 5 weeks. Tumor size was measured before treatment, followed by twice a week measurements. All treatment group mice were kept alive for up to 10 weeks after drug injection or until the tumor volume grows bigger than 2500 mm³.

Tumor size was measured along with body weight at the time of tissue collection. All tumor tissues were removed carefully from the euthanized mouse body. Tumor tissue samples were kept for histology, proteomics, genomics, and other downstream processing. All downstream processing was completed following NCI Patient-Derived Models Repository SOPs.

Mouse PDX to Human Dose Conversion

The Food and Drug Administration (FDA) has suggested that the extrapolation of animal dose to human dose is correctly performed only through normalization to body surface area (BSA), which often is represented in mg/m². The human equivalent doses (HEDs) can be more appropriately calculated by using the formula: Human Equivalent Dosage in mg/kg=Mice Dosage (mg/kg)×(Mice $K_m$/Human $K_m$). The correction factor ($K_m$) is estimated by dividing the average body weight (kg) of species to its body surface area (m²). For example, the average human body weight is 60 kg, and the body surface area is 1.62 m². Therefore, the $K_m$ factor for human is calculated by dividing 60 by 1.62, which is 37 and same way the mouse $K_m$ factor was calculated, which is 3. Now to interchange of unit (mg/kg to mg/m²) of dose of animals or human is carried out using the $K_m$ factor as per BSA: Dosage for mg/m²=$K_m$×dosage in mg/kg.

It will be appreciated that the embodiments and illustrations described herein are provided by way of example and that the present invention is not limited to what has been particularly disclosed. Rather, the scope of the present invention includes both combinations and sub combinations of the various features described above, as well as variations and modifications thereof that would occur to persons skilled in the art upon reading the forgoing description and that are not disclosed in the prior art. Therefore, the various compositions and methods may include one or all of the limitations of an embodiment, be performed in any order, or may combine limitations from different embodiments, as would be understood by those implementing the various methods and systems detailed herein.

What is claimed is:

1. A method for treating endometrial cancer comprising:
  a. administering to a patient an effective amount of a composition comprising a *cannabis* extract (CE) wherein the CE comprises between 50% and 99.9% cannabidiol (CBD) and wherein said composition has a pH of between 3.5 and 6;
  b. wherein the CE is administered via an intravaginal form; and
  c. wherein the effective amount of the CE comprises between 10 mg and 4,250 mg of CBD per day.

2. The method of claim 1 wherein the endometrial cancer is a grade 1, grade 2, grade 3, or chemoresistant endometrial cancer.

3. The method of claim 1 wherein the CE comprises cannabidiolic acid (CBDA) at a concentration of between 0.1% and 10%.

4. The method of claim 1 wherein the composition further comprises a carrier and wherein the CE is 50% to 99% of a total weight of the composition.

5. The method of claim 1 wherein the CE is a broad spectrum hemp extract (BSHE) or a full spectrum hemp extract (FSHE) and wherein each of the BSHE or FSHE comprises between 60% and 99% by weight of CBD and at least one other cannabinoid at a concentration of 0.1% to 10% by weight wherein the at least one other cannabinoid is selected from the group consisting of:
  Δ-9-tetrahydrocannabinol ($\Delta^9$-THC), tetrahydrocannabinolic acid (THCA), tetrahydrocannabivarin (THCV), Δ-8-tetrahydrocannabinol ($\Delta^8$-THC), cannabichromene (CBC), cannabichromene acid (CBCA), cannabigerol (CBG), cannabigerol acid (CBGA), cannabidiolic acid (CBDA), cannabidivarin (CBDV), cannabinol (CBN), cannabicyclol (CBL), and combinations thereof.

6. The method of claim 1 wherein the CE comprises cannabidiol (CBD) at a concentration of between 60% and 99% and at least one other cannabinoid at a concentration of 0.1% to 10% wherein the at least one other cannabinoid is selected from the group consisting of: Δ-9-tetrahydrocannabinol (Δ$^9$-THC), tetrahydrocannabinolic acid (THCA), tetrahydrocannabivarin (THCV), Δ-8-tetrahydrocannabinol (Δ$^8$-THC), cannabichromene (CBC), cannabichromene acid (CBCA), cannabigerol (CBG), cannabigerol acid (CBGA), cannabidiolic acid (CBDA), cannabidivarin (CBDV), cannabinol (CBN), cannabicyclol (CBL), and combinations thereof.

7. The method of claim 6 wherein a total concentration of cannabinoids in the CE is between 65% and 99%.

8. The method of claim 1 wherein the composition further comprises at least one additional compound selected from the group consisting of: a terpene, a polyphenol, an essential fatty acid, a phytonutrient, and combinations thereof; and
wherein the at least one additional compound makes up between 0.1% and 50% of a total weight of the composition.

9. The method of claim 1 wherein the composition comprises an oil or a fat as a carrier.

10. The method of claim 7 wherein the total concentration of the CE within the composition is at least 60% by weight.

11. The method of claim 5 comprising at least two or more of the at least one other cannabinoid.

12. A method of treating endometrial cancer comprising:
a. taking a cancerous cell from a patient and forming an organoid from the cancerous cell;
b. performing a screen on the organoid to determine a chemotherapeutic drug capable of reducing the percent of viable organoids by 50%;
c. administering to the patient the chemotherapeutic drug with an effective amount of a composition comprising a *cannabis* extract (CE) having between 50% and 99.9% cannabidiol (CBD) wherein the composition comprises a pH of between 3.5 and 6; and
d. wherein the CE is administered to the patient as an intravaginal form.

13. The method of claim 12 wherein a total concentration of cannabinoids in the CE is between 65% and 99%.

14. The method of claim 12 wherein the composition further comprises at least one additional compound selected from the group consisting of: a terpene, a polyphenol, an essential fatty acid, a phytonutrient, and combinations thereof; and wherein the at least one additional compound makes up between 0.1% and 50% of a total weight of the composition.

15. The method of claim 12 wherein the composition comprises an oil or a fat as a carrier.

16. The method of claim 12 wherein the CE is a broad spectrum hemp extract (BSHE) or a full spectrum hemp extract (FSHE) and wherein each of the BSHE or FSHE comprises between 60% and 99% by weight of CBD and at least one other cannabinoid at a concentration of 0.1% to 10% by weight wherein the at least one other cannabinoid is selected from the group consisting of:
Δ-9-tetrahydrocannabinol (Δ$^9$-THC), tetrahydrocannabinolic acid (THCA), tetrahydrocannabivarin (THCV), Δ-8-tetrahydrocannabinol (Δ$^8$-THC), cannabichromene (CBC), cannabichromene acid (CBCA), cannabigerol (CBG), cannabigerol acid (CBGA), cannabidiolic acid (CBDA), cannabidivarin (CBDV), cannabinol (CBN), cannabicyclol (CBL), and combinations thereof.

17. The method of claim 12 wherein the CE comprises cannabidiol (CBD) at a concentration of between 60% and 99% and at least one other cannabinoid at a concentration of 0.1% to 10% wherein the at least one other cannabinoid is selected from the group consisting of:
Δ-9-tetrahydrocannabinol (Δ$^9$-THC), tetrahydrocannabinolic acid (THCA), tetrahydrocannabivarin (THCV), Δ-8-tetrahydrocannabinol (Δ$^8$-THC), cannabichromene (CBC), cannabichromene acid (CBCA), cannabigerol (CBG), cannabigerol acid (CBGA), cannabidiolic acid (CBDA), cannabidivarin (CBDV), cannabinol (CBN), cannabicyclol (CBL), and combinations thereof.

18. The method of claim 12 wherein the composition further comprises a carrier and wherein the CE is 50% to 99% of a total weight of the composition.

* * * * *